US008998831B2

(12) United States Patent
Sankai

(10) Patent No.: US 8,998,831 B2
(45) Date of Patent: Apr. 7, 2015

(54) WEARABLE TYPE MOVEMENT ASSISTING APPARATUS

(75) Inventor: Yoshiyuki Sankai, Ibaraki (JP)

(73) Assignee: University of Tsukuba, Ibaraki (JP)

(*) Notice: Subject to any disclaimer, the term of this patent is extended or adjusted under 35 U.S.C. 154(b) by 519 days.

(21) Appl. No.: 13/263,082

(22) PCT Filed: Apr. 9, 2010

(86) PCT No.: PCT/JP2010/056470
§ 371 (c)(1),
(2), (4) Date: Oct. 6, 2011

(87) PCT Pub. No.: WO2010/117065
PCT Pub. Date: Oct. 14, 2010

(65) Prior Publication Data
US 2012/0029399 A1 Feb. 2, 2012

(30) Foreign Application Priority Data
Apr. 9, 2009 (JP) ................. 2009-094695

(51) Int. Cl.
A61H 1/00 (2006.01)
A61H 1/02 (2006.01)
(Continued)

(52) U.S. Cl.
CPC .......... A61H 1/0285 (2013.01); A61B 5/04888 (2013.01); A61B 5/1121 (2013.01);
(Continued)

(58) Field of Classification Search
CPC . A61H 1/0288; A61H 1/0274; A61H 1/0285; A61H 2201/12; A61H 2201/1201; A61H 2201/1207; A61H 2201/123; A61H 2201/1238; A63B 23/16
USPC ............................. 601/5, 23, 33, 40
See application file for complete search history.

(56) References Cited

U.S. PATENT DOCUMENTS 3,631,542 A 1/1972 Potter et al.
6,037,703 A 3/2000 Kambe et al.
(Continued)

FOREIGN PATENT DOCUMENTS

JP 6-006991 1/1994
JP 10-249768 9/1998
(Continued)

OTHER PUBLICATIONS

Extended European Search Report dated Oct. 1, 2012.
(Continued)

Primary Examiner — Justine Yu
Assistant Examiner — Kathrynn Reilly
(74) Attorney, Agent, or Firm — IPUSA, PLLC

(57) ABSTRACT

A wearable type movement assisting apparatus includes a movement assisting glove including a finger insertion part into which a finger of a wearer is inserted, a driving part arranged on a backhand side of the movement assisting glove and configured to drive the finger insertion part, a linear member arranged along the finger insertion part and configured to transmit a driving force of the driving part to the finger insertion part, a biosignal detection part configured to detect a biosignal that causes the finger of the wearer to move, and a control part configured to output a drive control signal to the driving part based on the biosignal detected by the biosignal detection part. The driving part is configured to move the linear member in an extending direction or a bending direction of the finger insertion part based on the drive control signal from the control part.

17 Claims, 43 Drawing Sheets

(51) Int. Cl.
*A61H 5/00* (2006.01)
*A61B 5/0488* (2006.01)
*A61B 5/11* (2006.01)
*A61B 5/00* (2006.01)
*A61F 5/01* (2006.01)
*A61B 5/04* (2006.01)
*A61B 5/0476* (2006.01)
*A61F 2/72* (2006.01)
*A61F 2/76* (2006.01)

(52) U.S. Cl.
CPC ............. *A61B5/6806* (2013.01); *A61B 5/6812* (2013.01); *A61F 5/013* (2013.01); *A61H 1/0288* (2013.01); *A61B 5/04001* (2013.01); *A61B 5/0476* (2013.01); *A61B 5/1125* (2013.01); *A61F 2/72* (2013.01); *A61F 2002/7625* (2013.01); *A61F 2002/7635* (2013.01); *A61F 2005/0188* (2013.01); *A61H 2201/149* (2013.01); *A61H 2201/165* (2013.01); *A61H 2201/5058* (2013.01); *A61H 2201/5061* (2013.01); *A61H 2201/5069* (2013.01); *A61H 2230/105* (2013.01); *A61H 2230/605* (2013.01)

(56) References Cited

U.S. PATENT DOCUMENTS

| | | | |
|---|---|---|---|
| 8,029,414 B2 * | 10/2011 | Ingvast et al. | 482/47 |
| 8,425,438 B2 * | 4/2013 | Fujimoto et al. | 601/40 |
| 2003/0125781 A1 | 7/2003 | Dohno et al. | |
| 2006/0167564 A1 | 7/2006 | Flaherty et al. | |
| 2006/0211956 A1 | 9/2006 | Sankai | |
| 2008/0234608 A1 | 9/2008 | Sankai | |

FOREIGN PATENT DOCUMENTS

| | | |
|---|---|---|
| JP | 2001-046450 | 2/2001 |
| JP | 2002-345861 | 12/2002 |
| JP | 2003-250842 | 9/2003 |
| JP | 2004-329490 | 11/2004 |
| JP | 2005-095561 | 4/2005 |
| JP | 2005-253650 | 9/2005 |
| JP | 2006-000294 | 1/2006 |
| JP | 2007-313093 | 12/2007 |
| JP | 2009-022577 | 2/2009 |
| WO | WO 2008/027002 A1 | 3/2008 |

OTHER PUBLICATIONS

International Search Report mailed on May 18, 2010.

* cited by examiner

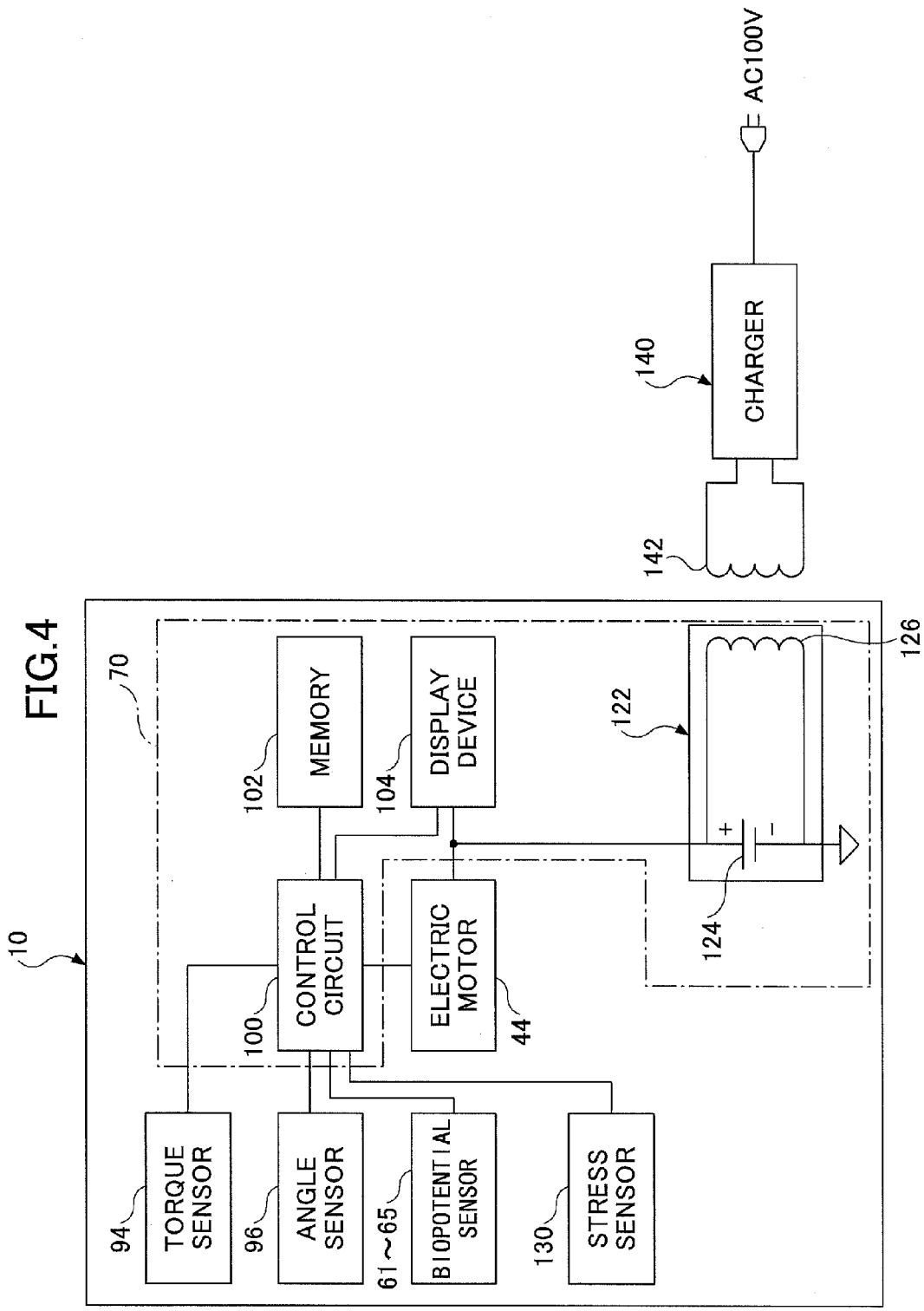

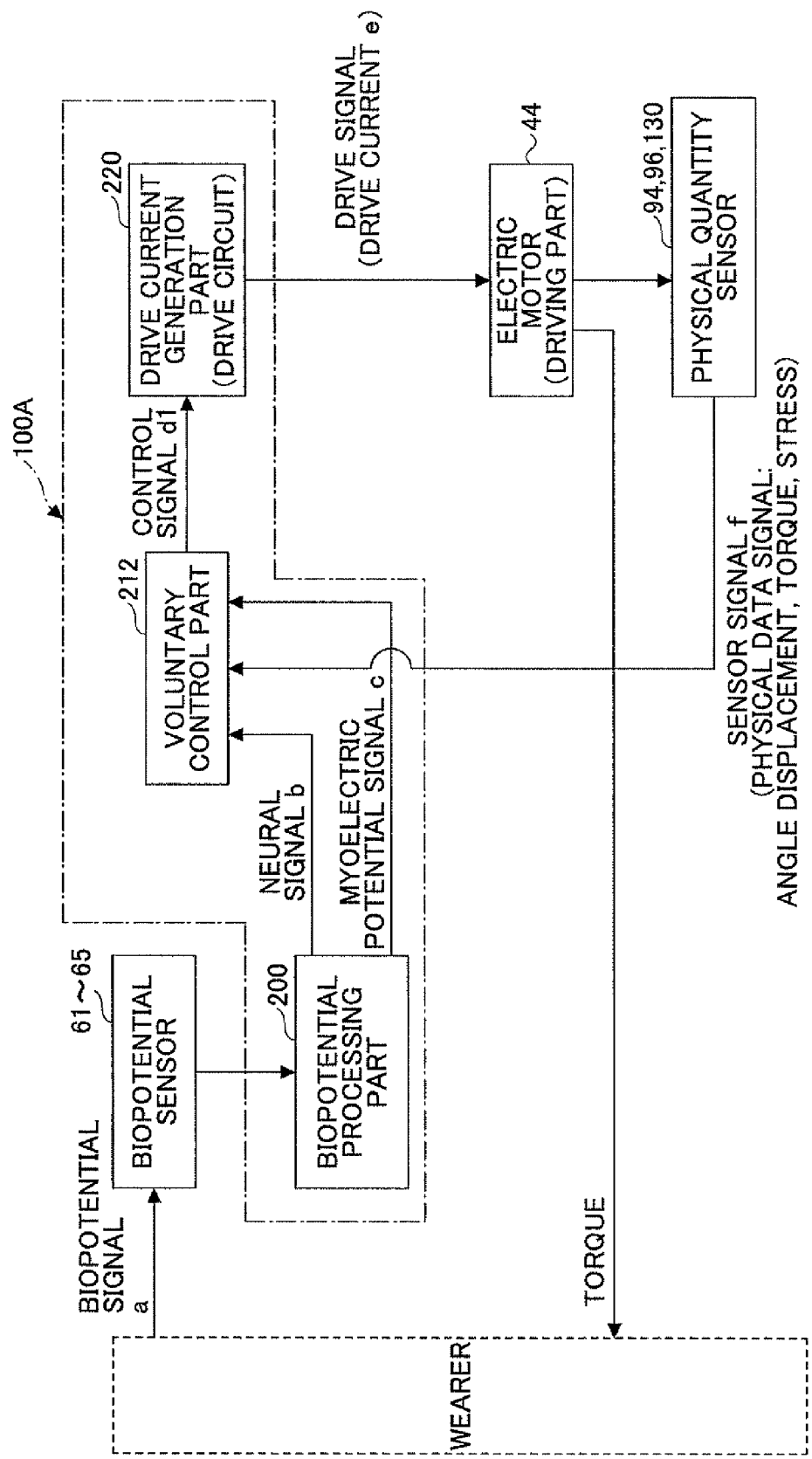

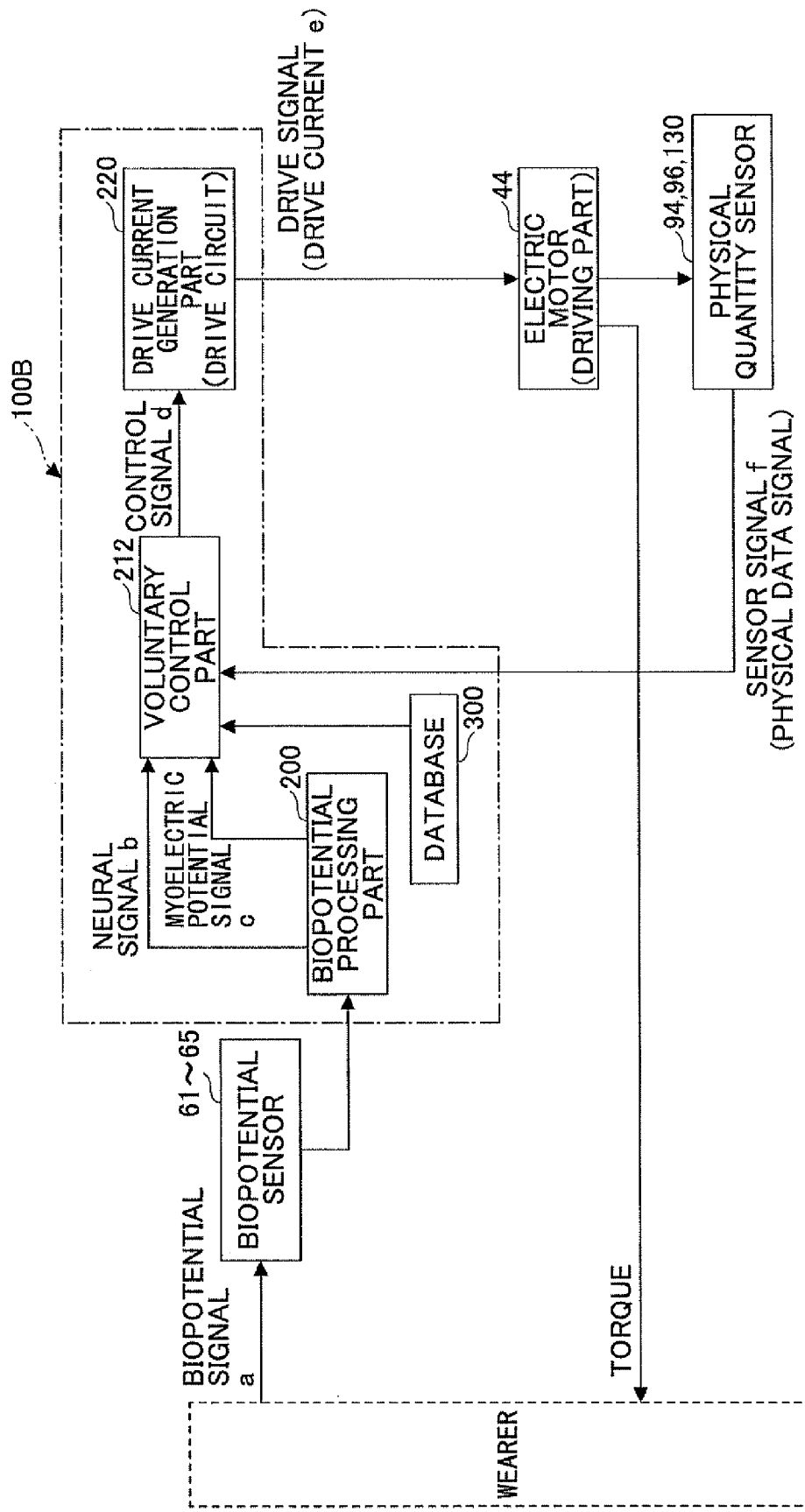

FIG.10A

| DATABASE 300 | | | | |
|---|---|---|---|---|
| TASK A (EXTEND FINGER) | PHASE A1 | PHASE A2 | PHASE A3 | ... |
| TASK B (GRAB OBJECT) | PHASE B1 | PHASE B2 | PHASE B3 | ... |
| TASK C (BEND FINGER) | PHASE C1 | PHASE C2 | PHASE C3 | ... |
| ... | ... | ... | ... | |

(PHASE A1 is circled)

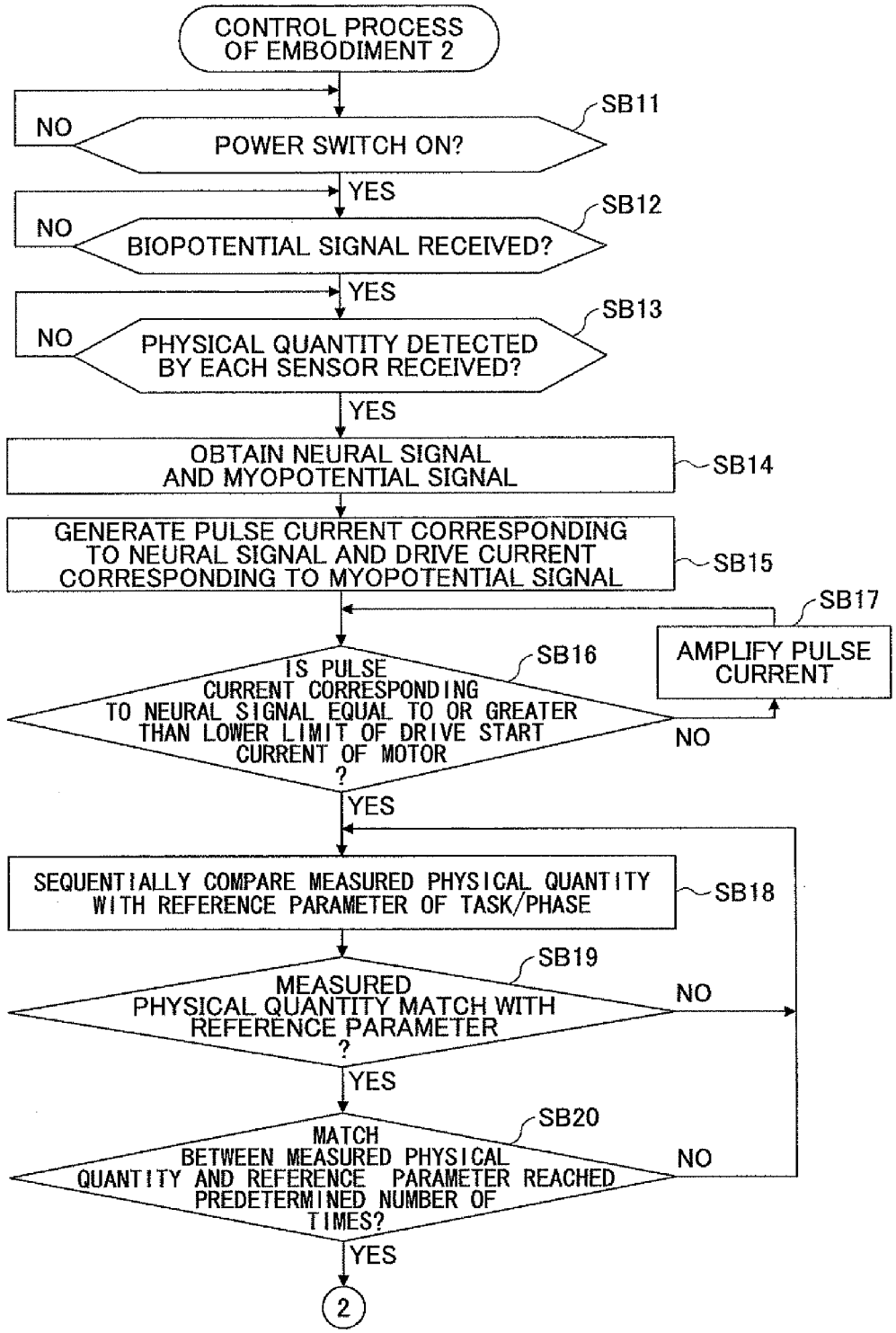

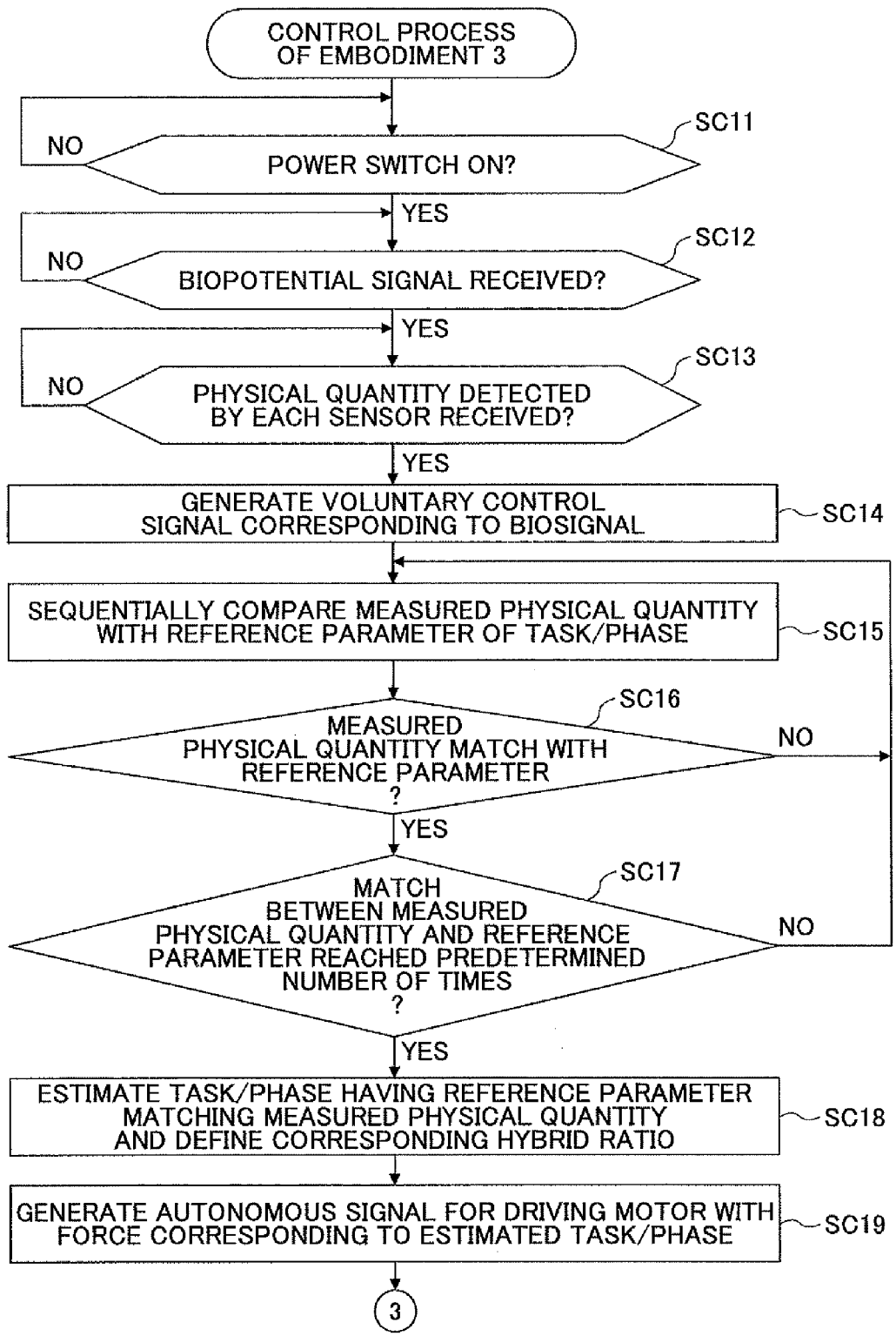

WEARABLE TYPE MOVEMENT ASSISTING APPARATUS

TECHNICAL FIELD

The present invention relates to a wearable type movement assisting apparatus, for example, a wearable type movement assisting apparatus for assisting or substituting movement of finger joints.

BACKGROUND ART

For example, there may be a case where it becomes difficult to transmit neural signals from the brain due to illness or injury or a case where it becomes difficult to move finger joints according to a one's intention due to deterioration of muscles or damage to one's tendons or ligaments provided at one's joints. As a wearable type movement assisting apparatus for assisting movement of such finger joints, there is an apparatus including movable parts attached to each finger and actuators for driving each of the movable parts (see, for example, Patent Document 1).

The conventional wearable type movement assisting apparatus, however, has many components and a sophisticated configuration due to a rotary mechanism being provided in correspondence with each finger joint and a configuration of mechanically transmitting a driving force of the actuators to respective movable parts. Thus, the conventional wearable type movement assisting apparatus has a considerable amount of weight and has a problem of imposing a large load on the wearer.

Although weight-reduction of the conventional wearable type movement assisting apparatus by reducing the size of the actuators is considered, there is a problem where torque cannot suffice for the weight of the movable parts made of many components.

Patent Document 1: Japanese Laid-Open Patent Application No. 2002-345861

DISCLOSURE OF INVENTION

Problem to be Solved by the Invention

In view of the above, it is an object to provide a wearable type movement assisting apparatus that can efficiently transmit a driving force of a driving part to a movement assisting glove.

Means for Solving Problem

According to an aspect of the present invention, there is provided a wearable type movement assisting apparatus including a movement assisting glove including a finger insertion part into which a finger of a wearer is inserted, a driving part arranged on a backhand side of the movement assisting glove and configured to drive the finger insertion part, a linear member arranged along the finger insertion part and configured to transmit a driving force of the driving part to the finger insertion part; a biosignal detection part configured to detect a biosignal that causes the finger of the wearer to move, and a control part configured to output a drive control signal to the driving part based on the biosignal detected by the biosignal detection part, wherein the driving part is configured to move the linear member in a extending direction or a bending direction of the finger insertion part based on the drive control signal from the control part.

Effect of the Invention

According to an aspect of the present invention, a driving force of a driving part allows a finger joint of a wearer to move by expanding or contracting a linear member in a movement direction of the finger joint in accordance with a drive control signal from a control part. Thereby, weight-reduction can be achieved. In addition, the load of the wearer can be reduced by efficiently transmitting the driving force of the driving part to a movement assisting glove.

BRIEF DESCRIPTION OF DRAWINGS

FIG. 4 is a schematic diagram illustrating a configuration of a control unit 70 including a control system and a charging system according to an embodiment of the present invention;

FIG. 5 is a system diagram of a control part 100A according to the first embodiment of the present invention;

FIG. 8 is a schematic diagram for describing a signal process of a control part 100B according to the second embodiment of the present invention;

FIG. 10A is a schematic diagram illustrating the tasks and phases stored in the database 300;

FIG. 11A is a flowchart for describing a first part of the steps performed in a control process executed by a control part 100B according to the second embodiment of the present invention;

FIG. 13A is a flowchart for describing a first part of the steps performed in a control process executed by a control part 1000 according to the third embodiment of the present invention;

Figure 1:
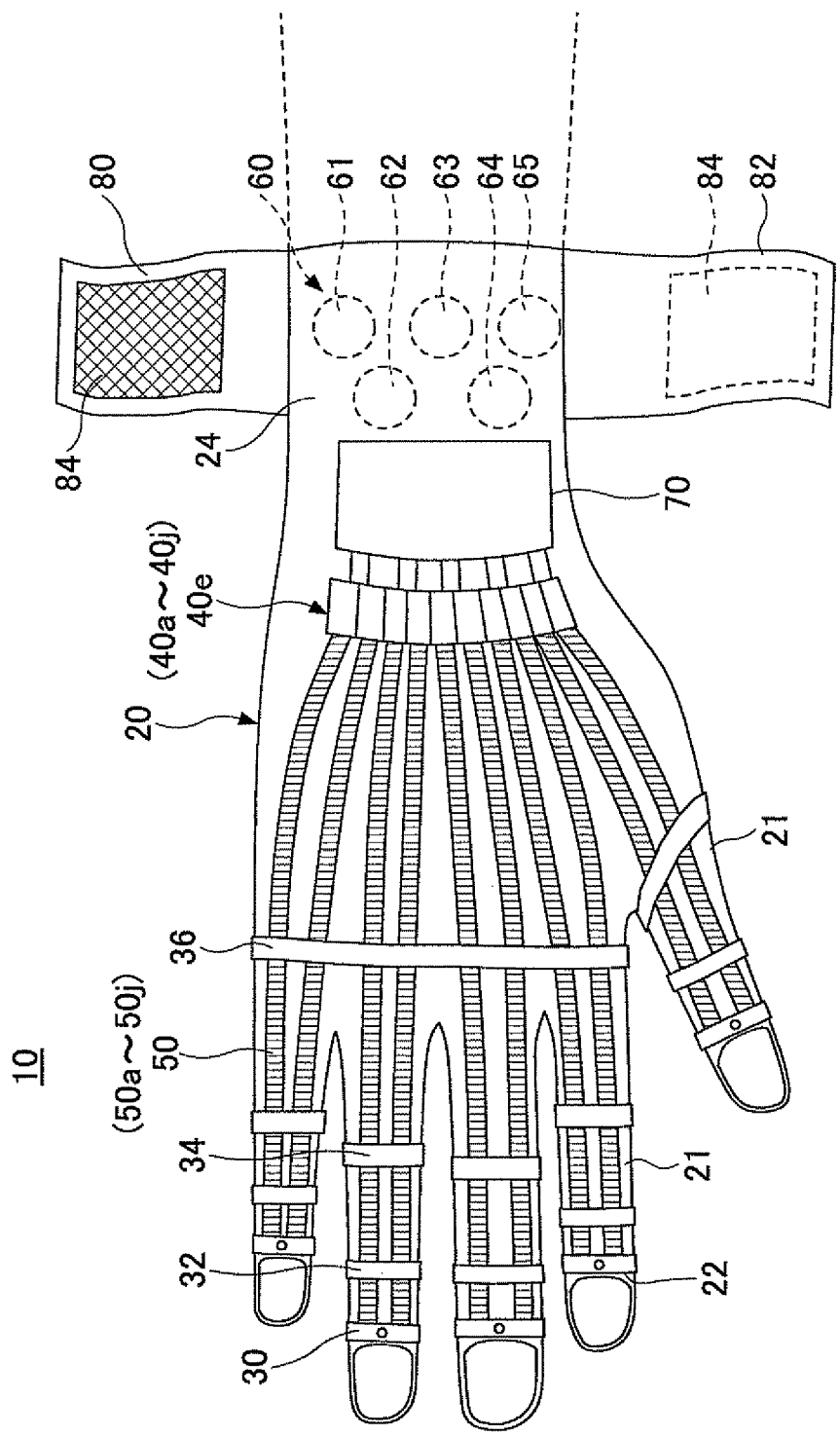
FIG. 1 is a plan view illustrating a wearable type movement assisting apparatus according to a first embodiment of the present invention.

EXPLANATION OF REFERENCE NUMERALS 10, 10A-10D wearable type movement assisting apparatus
20, 20A-20D movement assisting glove
21, 21A-21D finger insertion part
22 opening
24 wrist part
30 driven part
32, 34, 36 fastening ring
40, 510, 710 driving part
40a-40j driving mechanism
42 rotary member
44 electric motor
50, 50a-50j, 500, 700, 800 linear member
51 cylinder body
52, 53 wire
54 cap
55 hollow part
57 upper-section space
58 lower-section space
59 mid-section space
60 biosignal detection part
61-65 biopotential sensor
70, 70A, 70C, 70D control unit
80, 82 belt
84 plane fastener
90 urging member
94 torque sensor
96 angle sensor
100, 100A-100F control part
102 memory
104 display device
124, 610 rechargeable battery
130 stress sensor
140 charger
200 biopotential processing part (biosignal processing part)
202 amplifier
204 high band bandpass filter
206 mid-band bandpass filter
212 voluntary control part
220 drive current generation part
300 database 310 autonomous control part
320 control signal compositing part
400 calibration database
410 phase designating part
420 difference deriving part
430 parameter correction part
440 calibration control part
450 load generation part
502 hollow path
510a-510j actuator
520 fluid
530 housing
540 Peltier device
612 solar battery
600 object detection sensor
710a-710j linear motor
810 applied voltage switching circuit
801, 802 electrode layer
803 drive layer

BEST MODE FOR CARRYING OUT THE INVENTION

Next, embodiments of the present invention are described with reference to the drawings.

Embodiment 1

Figure 2A:
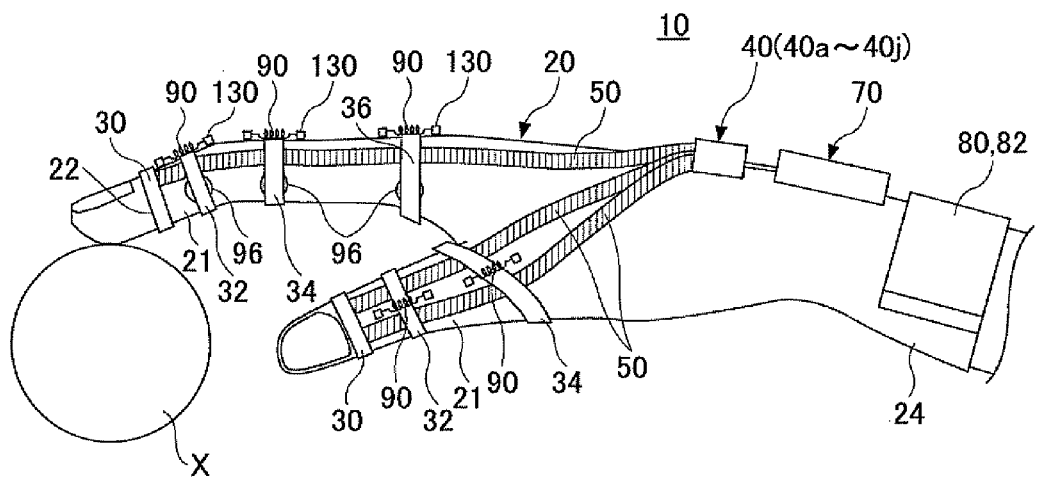
FIG. 2A is a side view of a wearable type movement assisting apparatus 10 according to the first embodiment of the present invention.
Figure 2B:
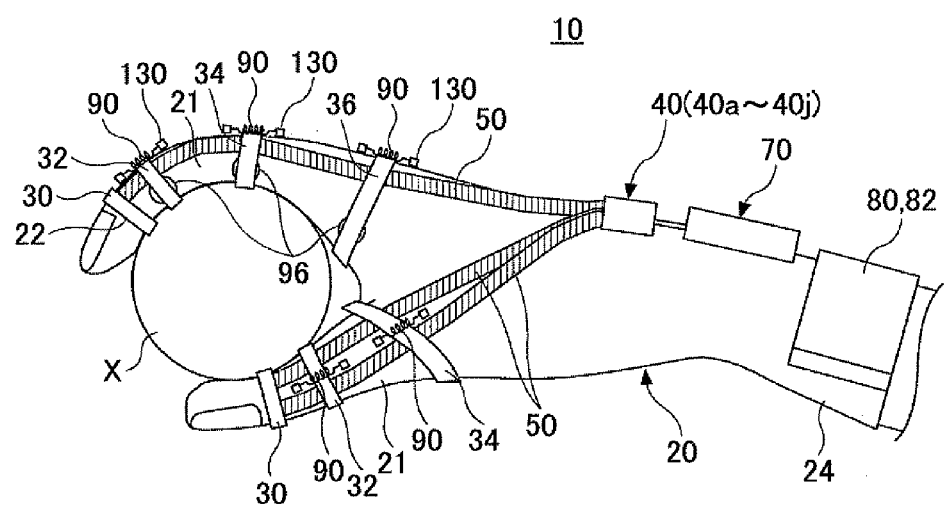
FIG. 2B is a schematic diagram illustrating a movement state where an object is grabbed by using the wearable type movement assisting apparatus 10 according to the first embodiment of the present invention.

FIG. 1 is a plan view illustrating a wearable type movement assisting apparatus according to a first embodiment of the present invention. FIG. 2A is a side view of the wearable type movement assisting apparatus 10 according to the first embodiment of the present invention. FIG. 2B is a schematic diagram illustrating a movement state where an object X is grabbed by using the wearable type movement assisting apparatus 10 according to the first embodiment of the present invention. As illustrated in FIGS. 1 and 2A, the wearable type movement assisting apparatus 10 has a movement assisting glove 20 including finger insertion parts 21 into which each finger of the wearer is inserted. The movement assisting glove 20 is worn in a same manner as a typical glove. The movement assisting glove 20 includes a driven part 30, a driving part 40 (40a-40j), a linear member 50 (50a-50j), a biosignal detection part 60, and a control unit 70.

The wearable type movement assisting apparatus 10 can provide assistance even in a case where, for example, a nervous system for moving a hand of a user is paralyzed because each finger insertion part of the movement assisting glove 20 can be driven in correspondence with a biosignal detected from the biosignal detection part 60, to thereby move the corresponding finger in an extending direction or a bending direction in accordance with a control signal from the control unit. Further, the wearable type movement assisting apparatus 10 can be used in rehabilitation (function recovery training) for training movement of a finger(s) of a hand.

The movement assisting glove 20 is formed in a three-dimensional shape. The movement assisting glove 20 is matched to the size of the hand of the wearer so that the hand can cohesively fit the movement assisting glove 20. Further, the movement assisting glove 20 has a dual structure in which an outer movement assisting glove and an inner movement assisting glove are sewn together to form a united body. For example, the outer movement assisting glove is formed with a material having a flexible and wear-resistant property such as cowhide or synthetic leather whereas the inner movement assisting glove is formed with a thin rubber material that can cohesively attach to the surface (skin) of a hand.

Further, openings 22, which expose the fingertips of the wearer, are provided at the fingertip portions of the finger insertion parts 21 of the movement assisting glove 20. As illustrated in FIG. 2A, the wearer can recognize an object X being grabbed from the feel of the fingertips because the skin of the fingertips directly contacts the object X being grabbed.

Plural of the linear members 50 (50a-50j) are provided on the backhand side of the movement assisting glove 20 along a direction in which each finger insertion part 21 extends. Each of the plural linear members 50 has one end coupled to the driven part 30 provided on a tip of the corresponding finger insertion part 21 of the movement assisting glove 20. Although the plural linear members 50 are formed with a material that transmits a driving force, the material of the plural linear members 50 is formed significantly lighter compared to, for example, a metal material. Thereby, the workload of the wearer can be reduced.

The driven part 30 is formed in a ring shape. The driven part 30 is provided on an outer side of the opening 22 in a manner cohesively attached to an outer periphery of the tip of the finger insertion part 21. Further, the plural linear members 50 are fastened to an outer side of each finger insertion part 21 by fastening rings 32, 34, 36 that wrap around finger joints of the wearer. Each of the fastening rings 32, 34, 36 has an angle sensor 96 for detecting the angle of the corresponding finger joint. In a case where the angle of one of the finger joints changes, the angle sensor 96 outputs a detection signal in correspondence with the angle change to the control unit 70.

Further, the plural linear members 50 are sewn to an outer side of each finger insertion part 21 or to an inner side of the outer movement assisting glove. Therefore, the plural linear members 50 are able to move in the expanding direction or the contracting direction. Further, each finger fitted to the movement assisting glove 20 can move in correspondence with the expansion or the contraction as a united body with the linear members 50.

As illustrated in FIGS. 2A and 2B, an urging member 90 is provided at an outer side of a finger joint portion of each finger insertion part 21. The urging member 90 may be an elastic member such as a coil spring or a rubber member. One end of the urging member 90 is coupled to a wrist side of the finger joint portion whereas the other end of the urging member 90 is coupled to a fingertip side of the finger joint portion. Accordingly, the urging member 90 applies an urging force (urging the finger insertion portion 21 to extend) to the surface covering the finger joint portion of the finger insertion portion 21. The urging force serves as an assisting force that assists the extending movement (movement from a grabbing state of FIG. 2B to a releasing state of FIG. 2A) of the corresponding finger joint.

It is to be noted that the urging member 90 may be attached in a manner that urges the finger joint in a bending direction. In a case where the urging member 90 is attached in such manner, the urging member would be provided on a palm side of the hand. Therefore, it is preferable to use an elastic member made by fabricating a rubber material into a flat shape, so that the feel of the object contacting the palm of the hand can be transmitted.

Further, a stress sensor 130 is provided at a coupling portion of the urging member 90. The stress sensor 130 includes, for example, a strain gauge. The stress sensor 130 outputs a detection signal to the control unit 70 in correspondence with a change of stress when the urging member 90 expands or contracts according to the movement of the finger joint.

The driving part 40 is provided on the backhand side of the movement assisting glove 20. The driving part 40 is for expanding or contracting the linear members 50 in a direction in which a joint of a finger moves. For example, the driving part 40 includes a driving mechanism 40a-40j for moving a wire inserted through the inside of the linear member 50 in the expanding direction or the contracting direction. In this embodiment, two of the linear members 50a-50j are provided on a backhand side of each finger insertion part 21 or on left and right sides of each finger insertion part 21. In addition, each finger insertion part 21 has a pair of driving mechanisms 40a-40j provided in parallel.

The biosignal detection part 60 includes plural biopotential sensors 61-65 provided on an inner side of a wrist part 24 of the movement assisting glove 20. Each of the biopotential sensors 61-65 includes an electrode capable of detecting a biosignal (e.g., a myopotential signal, a neural signal, a brainwave) that causes the finger of a hand to move. Further, belts 80, 82 are provided on both sides of the wrist part 24. The belts 80, 82 wrap around the outer side of the wrist of the wearer and cohesively attach to the hand of the wearer. The belts 80, 82 have plane fasteners 84 that engage with each other at a portion where the belts 80, 82 overlap. Accordingly, after adjusting the length of the portion where the belts 80, 82 overlap at the outer side of the wrist part 24 of the movement assisting glove 20, the plane fasteners 84 are faced against each other, so that the biopotential sensors 61-65 can be cohesively attached to the skin of the wearer. The biopotential sensors 61-65 detect biosignals when the wearer attempts to move the fingers and output detection signals corresponding to the biosignals.

The control unit 70 performs a calculation process (described in detail below) based on biosignals detected from the biopotential sensors 61-65 of the biosignal detection part 60 and outputs drive control signals to the drive mechanisms 40a-40j. Further, the control unit 70 includes a control part for performing the below-described calculation process, a memory, and a rechargeable battery.

Figure 3A:
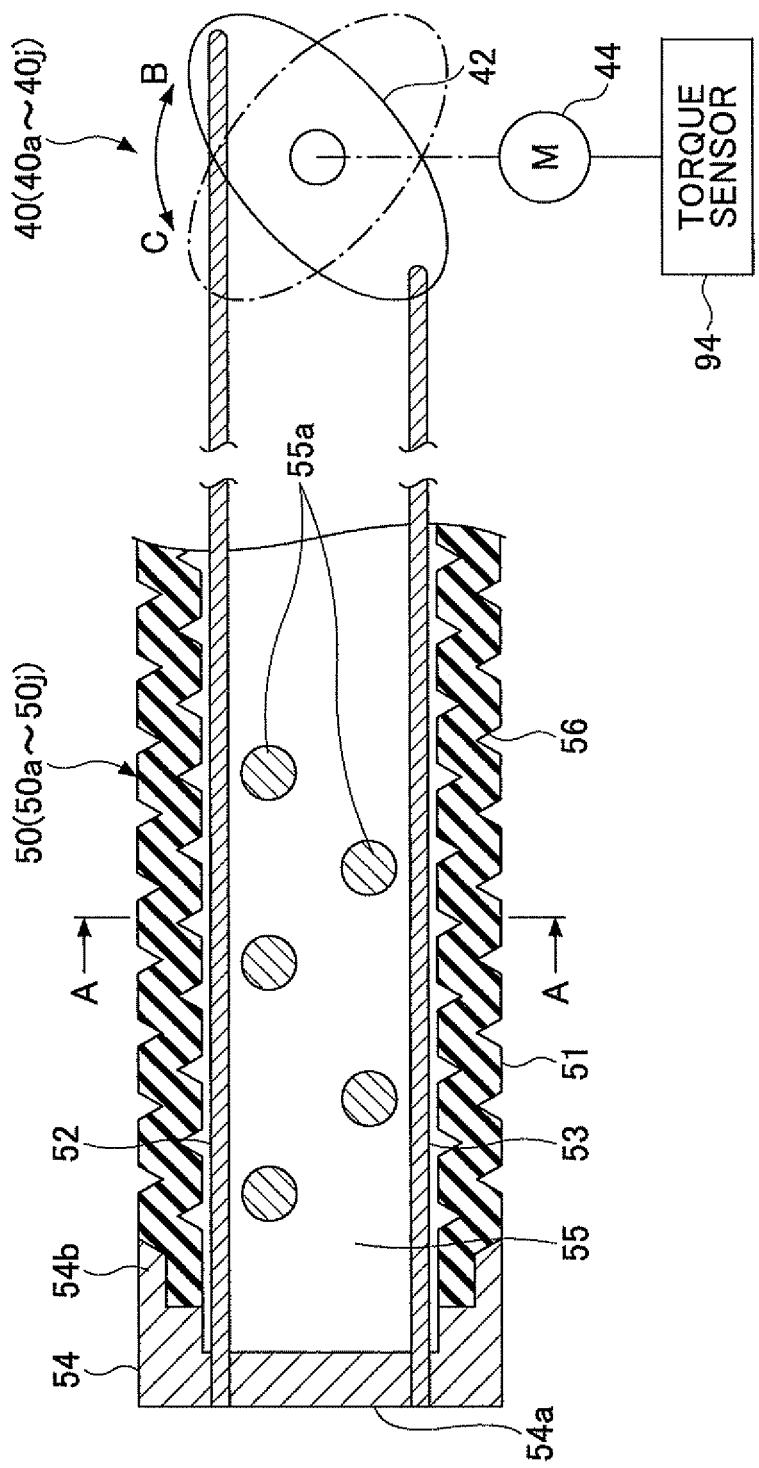
FIG. 3A is a schematic diagram illustrating configurations of a linear member 50 and a driving part 40.

Next, configurations of the linear member 50 and the driving part 40 are described. FIG. 3A is a schematic diagram illustrating the configurations of the linear member 50 and the driving part 40. As illustrated in FIG. 3A, the linear member 50 includes a cylinder body 51, wires 52, 53, and a cap 54. The cylinder body 51 is molded into a cylindrical shape with a resin material having a resilient property. The wires 52, 53 are inserted through a hollow part 55 provided in the inner side of the cylinder body 51. A bellows part 56 is provided at the outer side of the cylinder body 51. The bellows part 56 has concave parts and convex parts alternately arranged in series for expanding and contracting in correspondence with the extending movement or the bending movement of the finger joints.

Further, an opening communicating to the hollow part 55 is provided at a tip of the hollow part. The opening is sealed by the cap 54. The cap 54 is formed of a metal material. One end of each wire 52, 53 is inserted through a wall part 54a of the cap 54 and integrally bonded to the wall part 54a by welding. An end part of the cylinder body 51 is integrated with an periphery part 54b of the cap 54 by using an adhesive or welding.

Figure 3B:
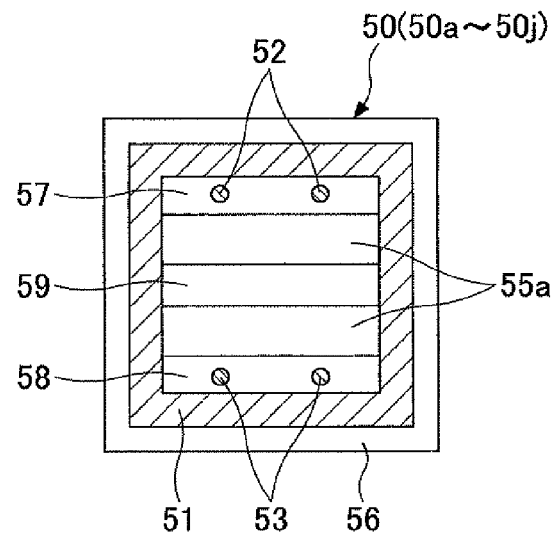
FIG. 3B is a vertical sectional view taken along line A-A of FIG. 3A.

FIG. 3B is a vertical sectional view taken along line A-A of FIG. 3A. As illustrated in FIG. 3B, the cross section of the cylinder body 51 has a quadrangle rectangular shape. Plural horizontal members 55a, which are horizontally provided in the hollow part 55, divide the hollow part 55 into an upper-section space 57, a lower-section space 58, and a mid-section space 59.

Two of the wires 52 span across the upper-section space 57. Two of the wires 53 span across the lower-section space 58. In this embodiment, a total of four wires 52, 53 are provided to be vertically symmetrical to each other in the cylinder body 51. Further, owing to the quadrangular shape of the cylinder body 51 having a quadrangular shape, the cylinder body 51 can be positioned in correspondence with the movement direction of the finger joints by contacting the lower surface of the cylinder body 51 to an outer surface of the movement assisting glove 20.

As illustrated in FIG. 3A, the other end of each wire 52, 53 is coupled to a rotary member 42 of the driving part 40. In this embodiment, the rotary member 42 is shaped as an oval. The other ends of the wires 52, 53 are coupled to a peripheral part of the oval at which the diameter of the oval is longest (i.e. the other ends coupled at a portion furthest from each other). The wires 52, 53 simultaneously move in correspondence with rotation angle of the rotary member 42 because the two wires 52, 53 are coupled one on each side of the rotary member 42. Further, a shaft penetrating through a center part of the rotary member 42 is coupled to an output shaft of an electric motor 44. Thereby, the driving part 40 can rotate the rotary member 42 and switch the rotating direction of the rotary member 42, so that the wire 52 and the wire 53 can be moved in opposite directions. Accordingly, driving force can be efficiently transmitted to each finger insertion part 21 of the movement assisting glove 20. Among the wires 52, 53, the one having a pulling force applied acts as a transmitting member that transmits a driving force for moving the finger insertion part 21. It is to be noted that a torque sensor 94 for detecting motor torque is provided on the other end of the output shaft of the electric motor 44.

For example, in a case where the rotary member 42 rotates in a clockwise direction (direction B), the wire 52 provided on the upper side moves in a pulling direction whereas the wire 53 provided on the lower side moves in a returning direction. Accordingly, the linear member 50 causes the cylinder body 51 to extend linearly. Therefore, the extending movement of the linear member 50 can be transmitted to the corresponding finger insertion part 21 of the movement assisting glove 20 and move the corresponding finger of the wearer to an open state (see FIG. 1 and FIG. 2A).

Figure 3C:
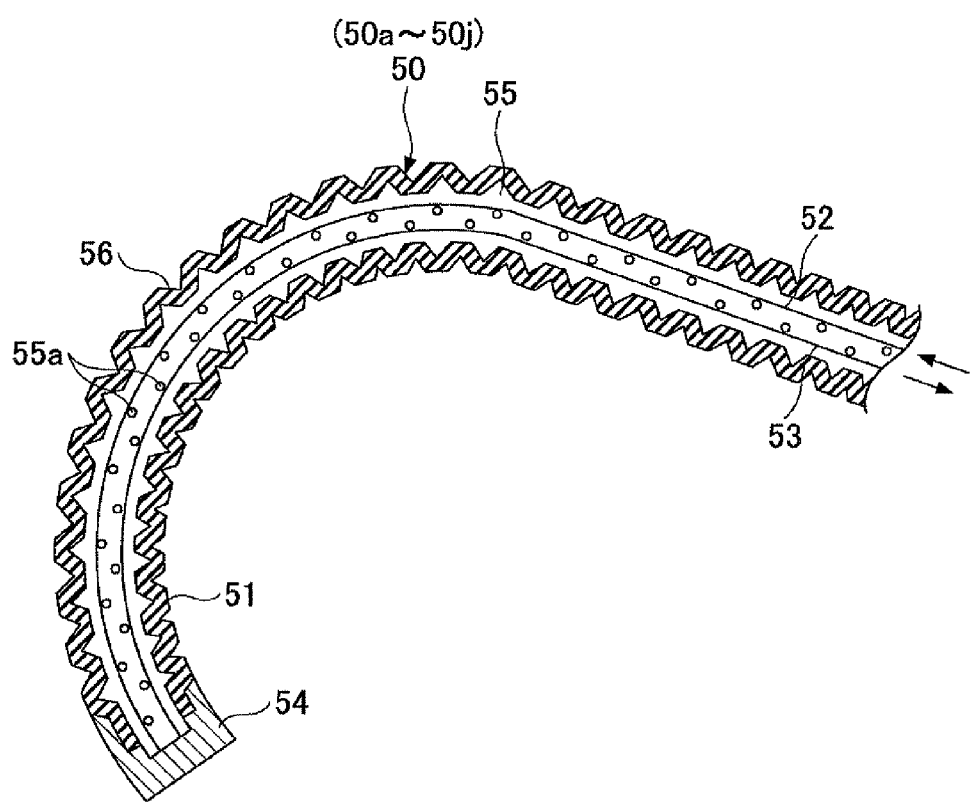
FIG. 3C is a schematic diagram illustrating a state of a contracting movement of a linear member 50.

Further, as illustrated with a dot-dash line in FIG. 3A, in a case where the rotary member 42 is moved in a counterclockwise direction (direction C), the wire 52 provided on the upper side moves in a returning direction whereas the wire 53 provided on the lower side moves in a pulling direction. Accordingly, as illustrated in FIG. 3C, the cylinder body 51 of the linear member 50 is moved to a bent state. Therefore, the contracting movement of the linear member 50 can be transmitted to each finger insertion part 21 of the movement assisting glove 20 and move each finger of the wearer to a gripping state (see FIG. 2B).

In this embodiment, a stroke (moving distance), being generated when the wire 52, 53 is driven in the expanding direction or the contracting direction, is determined in accordance with a longitudinal diameter of the oval-shaped rotary member 42. Thus, by increasing the length of the longitudinal diameter of the rotary member 42, a stroke generated from the contracting movement to the expanding movement of the linear member can be increased. Instead of using the rotary member 42, the stroke of the movement of the linear member 50 can be appropriately adjusted by providing a gear mechanism and a driving mechanism such as a pulley for rewinding the wires 52, 53 and adjusting the rotation amount of the pulley.

Accordingly, the wearable type movement assisting apparatus 10 can transmit a driving force of the driving part 40 to cause the finger joints of the wearer to move by expanding and contracting the linear members 50 in the movement direction of the joints of the finger insertion parts 21 in accordance with drive control signals from the control unit 70. Thereby, weight of the wearable type movement assisting apparatus 10 and the load of the wearer can be reduced.

FIG. 4 is a schematic diagram illustrating a configuration of the control unit 70 including a control system and a charging system according to an embodiment of the present invention. As illustrated in FIG. 4, the control unit 70 includes a control part 100, a memory 102, a display device 104, and a rechargeable battery 124.

Biosignals detected from the biopotential sensors 61-65, torque detection signals of the electric motor 44 detected by the torque sensor 94, and stress detection signals detected by a stress sensor 130 are input to the control part 100. The control part 100 reads each control program and each parameter stored in the memory 102, performs calculation based on the detection signals from the torque sensor 94, the angle sensor 96, and the stress sensor 130, and displays a movement status of the movement assisting glove 20 on the display device 104. The rechargeable battery 124 is connected to a secondary coil 126 of a charging unit 122 and is periodically charged by a charger 140.

The charger 140 includes a primary coil 142 for generating an electromagnetic induction current in the secondary coil 126. Accordingly, the rechargeable battery 124 can be charged in a state where the movement assisting glove 20 is worn. Thus, the rechargeable battery 124 can be charged even where the movement assisting glove 20 is worn by the wearer.

FIG. 5 is a system diagram of the control part according to the first embodiment of the present invention. A control part 100A illustrated in FIG. 5, which is an example of the control part 100 illustrated in FIG. 4, is a computer that executes the below-described control processes by reading a control program from the memory 102.

In this embodiment, the control part 100A includes a biopotential process part (biosignal process part) that obtains command signals from biopotential signals detected by the biopotential sensors 61-65, a voluntary control part 212 that controls the driving of the electric motor based on neural signals b and myopotential signals c, a drive current generation part 220 that supplies a drive current to the electric motor 44 in correspondence with control signals output from the voluntary control part 212.

The voluntary control part 212 outputs controls signals to the drive current generation part 220 based on command signals from a biopotential process part 200 that generates neural signals b and myopotential signals c from biopotential signals "a" that are generated whenever a finger is moved in accordance with the intention of the wearer. The drive current generation part 220 generates a drive current corresponding to the control signal from the voluntary control part 212 and outputs the drive current to the electric motor 44.

The biopotential sensors 61-65 detect biopotential signals "a" generated inside an upper arm and input the biopotential signals "a" to the biopotential process part 200. The biopotential process part 200 extracts neural signals b and myopotential signals c from the biopotential signals "a" and inputs the neural signals b and the myopotential signals c to the voluntary control part 212. The voluntary control part 212 generates a voluntary control signal d1 based on the neural signals b and the myopotential signals c obtained from the biopotential signals "a" generated when the wearer attempts to move one or more fingers of the hand on which the movement assisting glove 20 is worn.

In other words, the voluntary control part 212 uses the neural signals b and the myopotential signals c included in the biopotential signals "a" to generate voluntary control signals d1 for generating motive power in the electric motor 44 in accordance with the intention of the wearer. Proportional control may be applied as the control logic (control rule) used in the voluntary control part 212. In accordance with the proportional control rule, the voluntary control signal d1 and a drive current e have a proportional relationship. Further, in accordance with the characteristic of the electric motor 44, the value of the drive current and the value of the torque generated by the electric motor 44 have a proportional relationship. Alternatively, a combination of proportional control, derivative control, and integral control or a combination of proportional control and integral control may be applied as the control logic used in the voluntary control part 212.

For example, in a case where the wearer attempts to move a joint, the biopotential sensors 61-65 directly detect the biopotential signal that causes a finger to move and output a biopotential signal "a" to the biopotential process part 200 in correspondence with the detected biopotential signal. In such manner, the biopotential sensors 61-65 directly detect the biopotential signals "a" from the wrist part 24 of the movement assisting glove 20 that is cohesively attached to the wrist of the wearer via the belts 80, 82. Therefore, the biopotential signals "a" can be accurately detected such that even a weak signal can be precisely detected.

The voluntary control part 212 receiving command signals including neural signals b and myopotential signals c from the biopotential process part 200, generates the control signals d1 from the neural signals b and the myopotential signals c and outputs the control signals d1 to the drive current generation part 220.

The drive control generation part 220 generates the drive current e based on the control signals d from the voluntary control part 212 and supplies the drive current e to the electric motor 44. Thereby, the electric motor 44 rotates the rotary member 42 in the extending direction or the bending direction in accordance with the supplied drive current e. Accordingly, the wires 52, 53 that span inside the hollow part 55 of the cylinder body 51 are moved to cause the linear member 50 of the movement assisting glove 20 to perform an expanding movement or a contracting movement.

Figure 6:
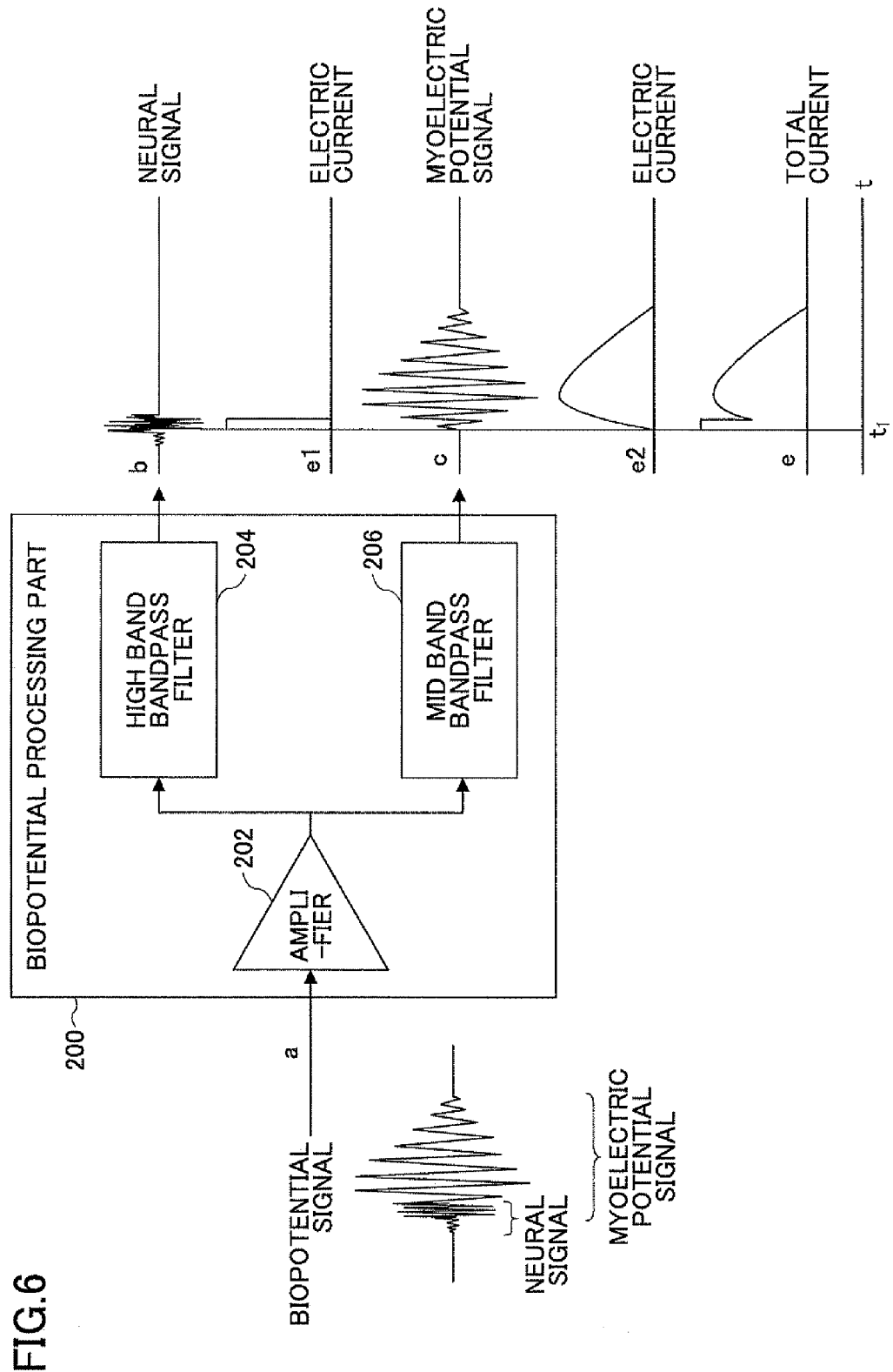
FIG. 6 is a schematic diagram illustrating a process of generating control signals from a biopotential signal according to an embodiment of the present invention.

FIG. 6 is a schematic diagram illustrating a process of generating control signals from a biopotential signal according to an embodiment of the present invention.

As illustrated in FIG. 6, a biopotential signal "a" detected by one of the biopotential sensors 61-65 includes a neural signal b and a myopotential signal c. The neural signal b, which may also be referred to as an intention transmitting signal, overlaps with a front part of the myopotential signal c. Because the frequency of the neural signal b is generally higher than the frequency of the myopotential signal c, the neural signal b and the myopotential signal c can be separated by using different bandpass filters.

After the biopotential signal "a" is amplified by an amplifier 202, the neural signal b can be extracted by using, for example, a high band bandpass filter 204 of 33 Hz to several KHz. Further, after the biopotential signal "a" is amplified by the amplifier 202, the myopotential signal c can be extracted by using, for example, a mid-band bandpass filter 206 of 33 Hz to 500 Hz. Although the filters 204, 206 are connected in parallel in FIG. 6, the filters 204, 206 may be connected in series.

Further, the neural signal b may not only overlap with the myopotential signal c at the front part of the myopotential signal c but also overlap at a part following the front part of the myopotential signal c. In this case, only the neural signal b at the front part may be used for generating the below-described pulse current.

Then, a smoothing process (a process of removing noise) is performed on the neural signal b and the myopotential signal c. Control signals d1, which are obtained by performing the smoothing process on the signals from the biosignal process part 200, are input to the drive current generation part 220. Thereby, the drive current generation part 220 generates electric current e corresponding to the neural and myopotential signals b and c.

Because the neural signal b is narrow with respect to the time axis, the neural signal b is given a pulse shape by merely performing the smoothing process on the neural signal b. Therefore, the drive current generation part 220, which generates a current in accordance with such neural signal b, generates a current having a pulse shape. The current (pulse current) e1 obtained in accordance with the neural signal b has a rectangular wave shape. On the other hand, because the myopotential signal c is wide with respect to the time axis, the myopotential signal c has a arch shape that is substantially proportional to the myopotential by performing the smoothing process on the myopotential signal. Therefore, the drive current generation part 220, which generates a current in accordance with such myopotential signal c, generates a current e2 having an arch shape.

The total current e (voluntary control signal) of the pulse current e1 generated in accordance with the neural signal b and the current e2 generated in accordance with (and proportional to) the myopotential signal c is supplied to the electric motor 44. When the total current e is supplied to the electric motor 44, the electric motor 44 generates a torque having a size proportional to the total current e. The size of each current e, e1, e2 input to the electric motor 44 is adaptively set in accordance with the feel (sense) of the wearer during movement.

In this embodiment, because a sufficiently large amount of current is set as the total current e, the electric motor 44 is driven without delay based on the wearer's intention to move a finger joint. Thereby, the wearer can move the finger joints in accordance with the wearer's intention without a sense of discomfort. Although the pulse current e1 is illustrated as a significantly large current, such illustration is merely for emphasizing the role of the pulse current e1 and is not intended to indicate the relationship between the actual pulse current e1 and the drive current e2 obtained from the myopotential signal.

Next, the steps performed in the control process executed by the control part 100A of the control system illustrated in FIG. 5 are described with reference to the flowcharts of FIGS. 7A and 7B. The control part 100A reads a control program stored in the memory 102 and executes the control process of FIG. 7.

Figure 7A:
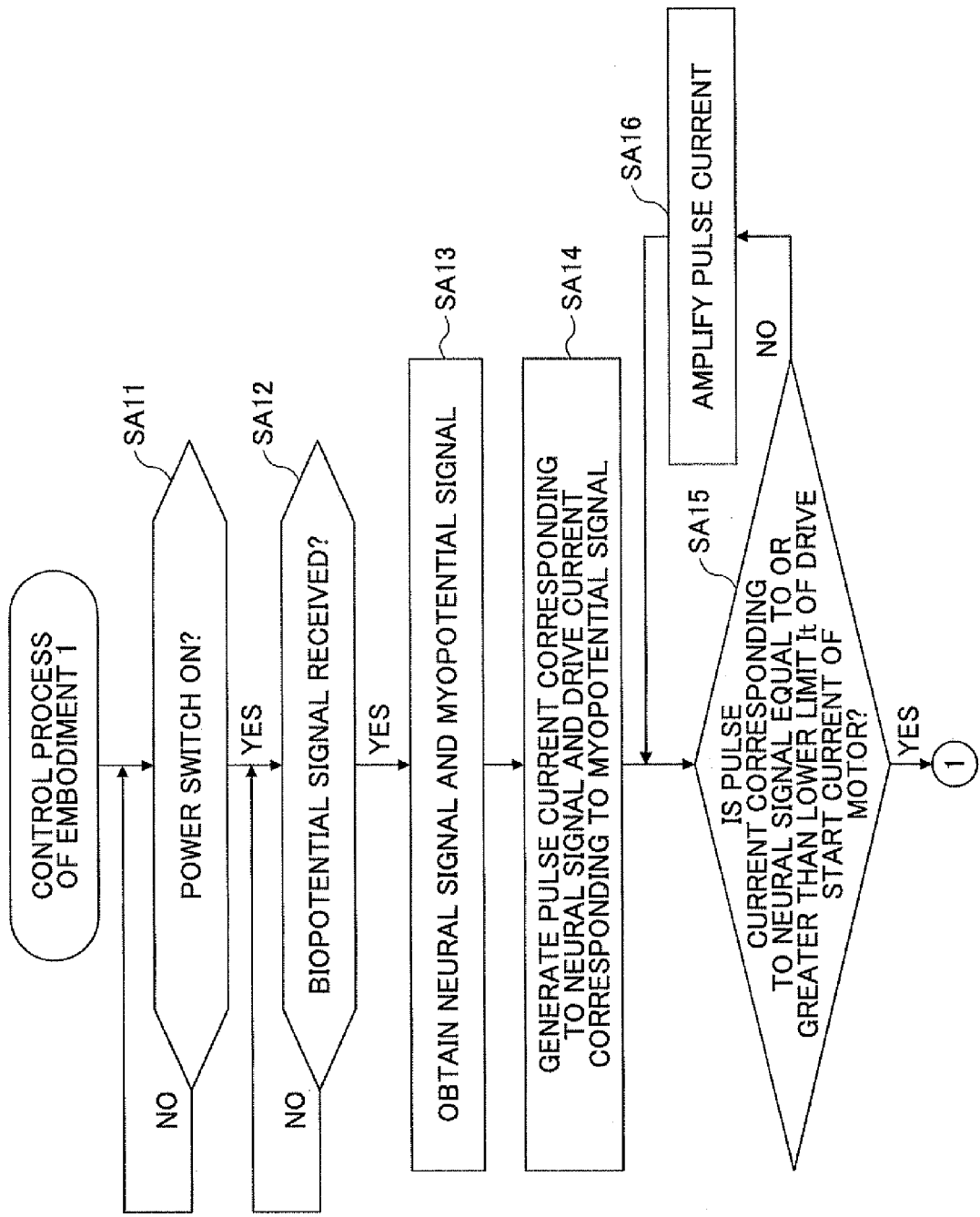
FIG. 7A is a flowchart for describing a first part of the steps performed in a control process executed by a control part 100A.

In step SA11 of FIG. 7A, the process proceeds to step SA12 when the power of the control unit 70 is switched on. Then, in step SA12, it is determined whether a biopotential signal "a" is detected by the biopotential sensors 61-65. In a case where the wearer attempts to move a finger joint, the process proceeds to step SA13 because a biopotential signal "a" is detected by the biopotential sensors 61-65.

In step SA13, a neural signal b and a myopotential signal c are obtained from the biopotential signal "a" detected from the biopotential sensors 61-65 (biopotential process part). Then, in step SA14, a pulse current e1 is generated based on the neural signal b and a current e2 is generated based on the myopotential signal c (drive current generation part).

Then, in step SA15, it is determined whether the pulse current e1 is equal to or greater than a lower limit value It of the drive start current of the electric motor 44. In a case where the pulse current e1 is not equal to or greater than the lower limit value It (No in step SA15), the process proceeds to step SA16. In step SA16, the pulse current e1 is amplified to be equal to or greater than the lower limit value It of the drive start current.

Figure 7B:
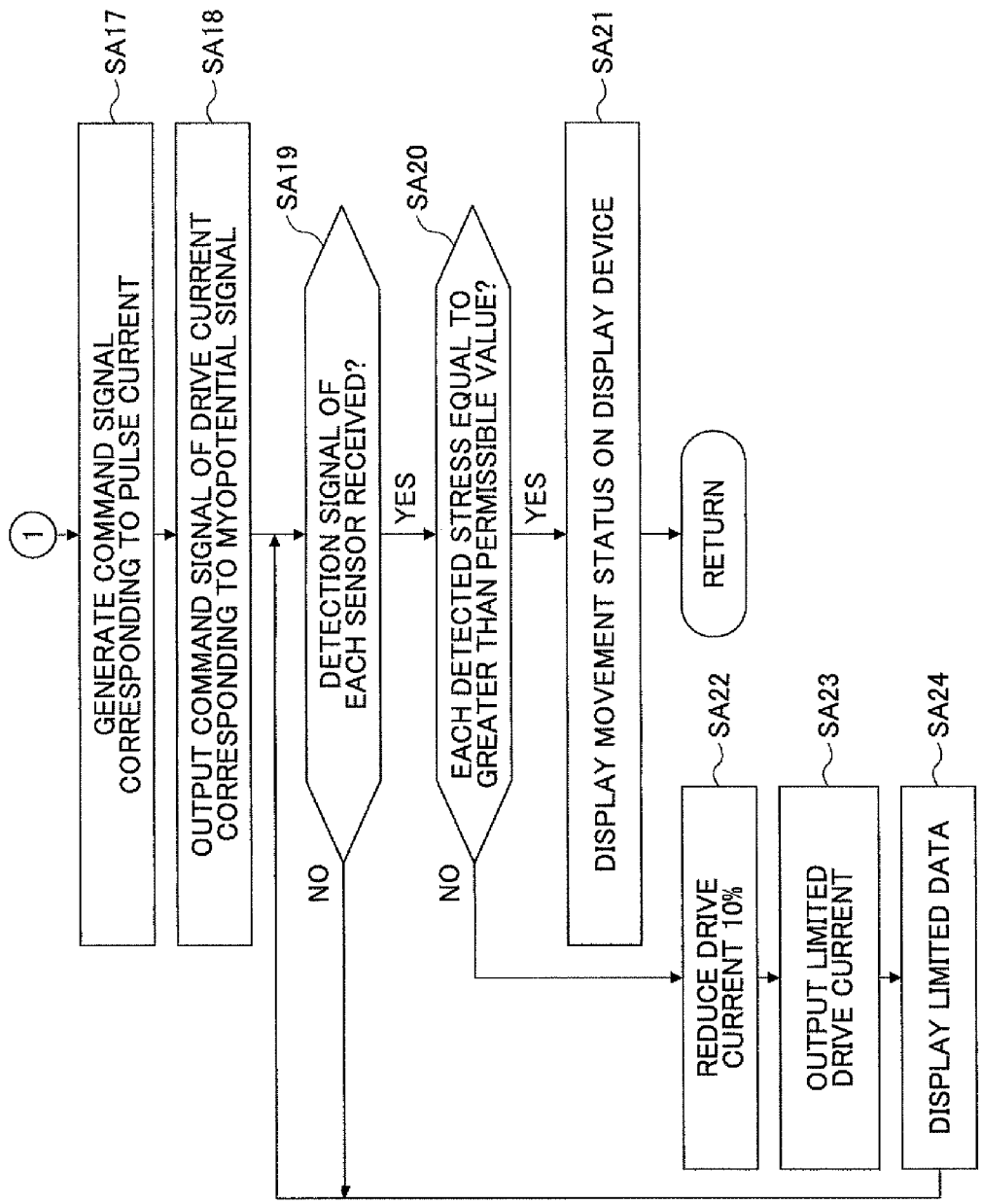
FIG. 7B is a flowchart for describing a second part of the steps performed in a control process executed by a control part 100A.

Further, in a case where the pulse current e1 is equal to or greater than the lower limit value It (Yes in step SA15), the process proceeds to step SA17 of FIG. 7B. In step SA17, a command signal corresponding to the pulse current e1 is generated. Then, in step SA18, the drive current e2 based on the myopotential signal c is output to the electric motor 44. Thereby, the corresponding linear member 50 of the movement assisting glove 20 can perform an expanding movement or a contracting movement.

Then, in step SA19, each finger joint is moved in accordance with the movement of a corresponding linear member 50 of the movement assisting glove 20. In addition, it is determined whether a sensor signal f of the torque sensor 94, the angle sensor 96, and the stress sensor (physical quantity sensor) 130 is received.

Then, in step SA20, it is determined whether the stress (stress generated from the finger joint moved by the driving force of the electric motor 44) detected by the stress sensor 130 is equal to or less than a permissible value that is determined beforehand. The permissible value is selectively set in correspondence with the strength of the urging force of the urging member 90. Thereby, the electric motor 44 can be controlled to prevent the finger joint from being excessively moved. Thus, the finger joint can be prevented from being damaged by the driving force of the electric motor 44.

Therefore, in a case where the stress detected by the stress sensor 130 is equal to or less than the permissible value (Yes in step SA20), the process proceeds to step SA21. In step SA21, the detected values (physical data) of each physical quantity sensor (torque sensor 94, angle sensor 96, stress sensor 130) and the biopotential signal are displayed on the display device 104. Thereby, the wearer can recognize the movement status of each finger joint (driving force and driving direction of each linear member 50) from the display of the display device 104.

Further, in a case where the stress detected by the stress sensor 130 is equal to or greater than the permissible value (Yes in step S20), the process proceeds to step SA 22. In step SA22, the drive current e supplied to the electric motor 44 is lowered to, for example, 10%. The drive current e can be discretionally lowered to a given value. For example, the range of lowering the drive current e may set within a range of 1 to 10%.

Then, in step S23, such limited drive current is output to the electric motor 44. Accordingly, the electric motor 44 is controlled so that the electric motor 44 generates a torque with a rotation angle that does not surpass the strength of the finger joint.

Then, in step SA24, data of the limited drive current is displayed on the display device 104. Then, returning to step SA19, it is determined whether a sensor signal f of the torque sensor 94, the angle sensor 96, and the stress sensor (physical quantity sensor) 130 is received and the processes following step SA19 are performed.

By repeating the processes of steps SA19, SA20, SA22-SA24 of the control process, the driving force of the electric motor 44 is controlled to a value equal to or less than the permissible value. Thereby, torque can be prevented from being excessively transmitted.

The processes of steps SA11-SA24 are repeated until the power of the control unit 70 is switched off. Hence, the driving of the electric motor 44 can be controlled to enable movement corresponding to the intention of the wearer.

Embodiment 2

FIG. 8 is a schematic diagram for describing a signal process of a control part 100B according to the second embodiment of the present invention. In the second embodiment, like components/elements are denoted with like reference numerals as those illustrated in FIG. 4 of the first embodiment and are not further described.

The control part 100B of the second embodiment illustrated in FIG. 8 includes the biopotential process part 200, the voluntary control part 212, a database 300, and the drive current generation part 220. Because the configuration of the movement assisting glove 20 of the second embodiment is the same as that of the first embodiment, the movement assisting glove 20 of the second embodiment is not further described. The control part 100B is an example of the control part 100 of FIG. 3.

The database 300 of the control part 100E obtains, for example, the rotation angles and the angular speed of each finger joint of the wearer corresponding to all phases of all tasks from past experience and stores reference parameters corresponding to the obtained information (e.g., reference parameter of rotation angle and angular speed). Then, in a case of performing voluntary control on the electric motor 44 of the movement assisting glove 20 (as illustrated in FIGS. 1 to 3), the voluntary control part 212 estimates a task and a phase from the physical quantity pertaining to the movement of each finger joint of the wearer by referring to the database 300. Then, the voluntary control part 212 causes the electric motor 44 to generate a driving force to match a power assist rate corresponding to the estimated phase.

Next, the task and the phase are described. A "task" is a movement pattern obtained by categorizing movement patterns of finger joints of the wearer. A "phase" is a smallest unit of a series of movements that constitute a task.

Figure 9:
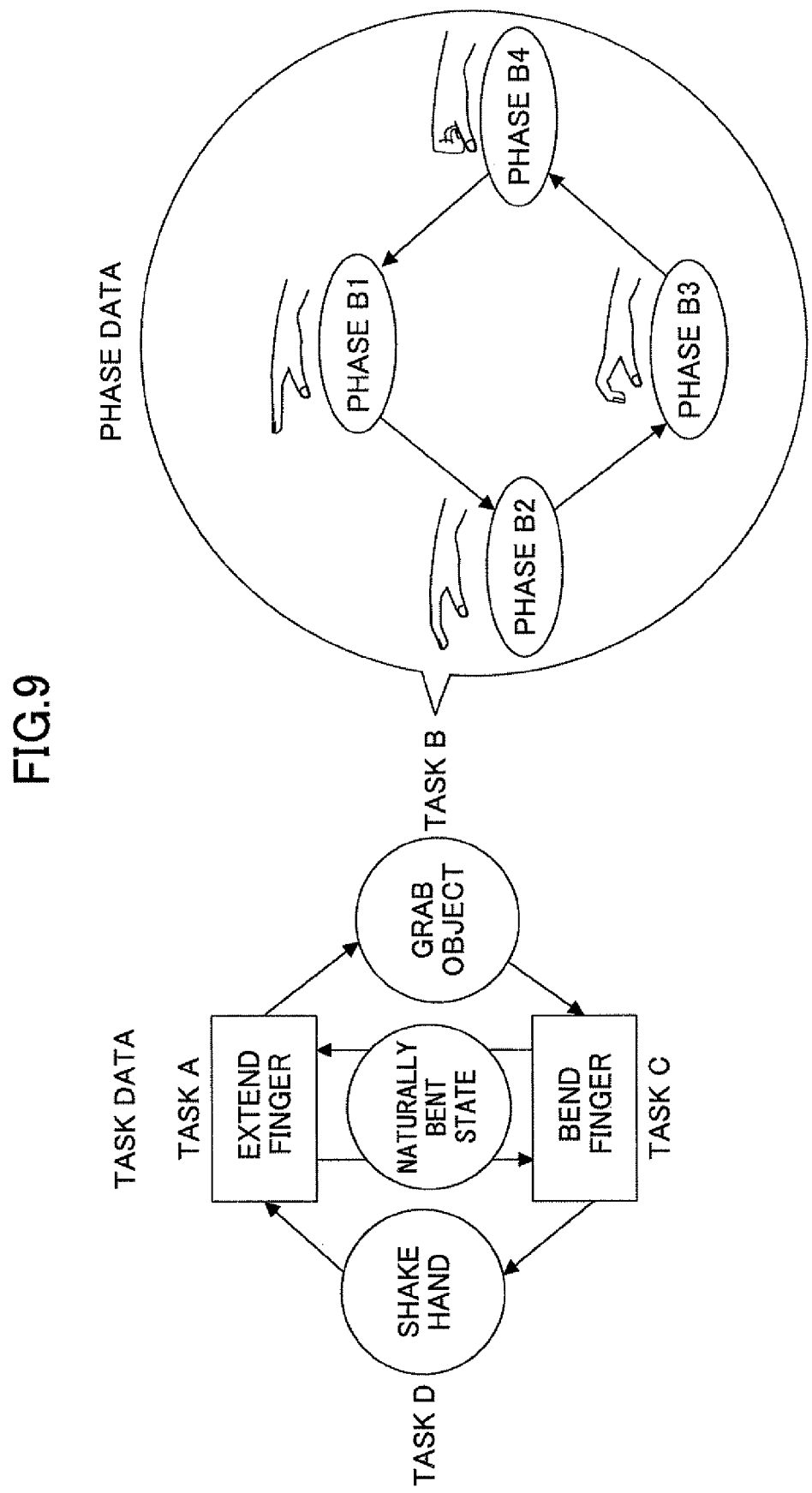
FIG. 9 is a schematic diagram illustrating basic movements of a finger including extending of a finger (task A), grabbing of an object (task B), bending of a finger (task C), and shaking of a hand (task D)

FIG. 9 is a schematic diagram illustrating basic movements of a finger including extending of a finger (task A), grabbing of an object (task B), bending of a finger (task C), and shaking of a hand (task D). Although this embodiment describes a case where the movement assisting glove 20 is worn by the wearer (as illustrated in FIGS. 1-3), movements of each finger are described for the sake of convenience.

As illustrated in FIG. 9, each task is constituted by phases. For example, the task B (grabbing an object) includes a phase B1 in which the fingers are aligned, a phase B2 in which the first joint of each finger is bent, a phase B3 in which the first and second joints of each finger are bent, and a phase B4 in which the first, second, and third joints of each finger are bent.

The series of phases B1-B4 may be referred to as a phase sequence. The appropriate driving force for assisting the movement of each finger joint of the wearer differs depending on the phase. By applying different power assist rates PAR1-PAR4 to each phase, optimum movement assistance can be provided for each phase.

In analyzing the movement of each finger joint of the wearer, it is understood that the rotation angle, the angular speed, the movement speed, the acceleration rate, and the like of the finger joint for each phase are fixed. For example, a typical finger movement pattern of the wearer is fixed such that the wearer feels most comfortable where the movement assisting glove 20 is moved in accordance with the movement pattern. Accordingly, the rotation angle, the angular speed, and the like of each finger joint of the wearer for all of the phases of all tasks are obtained from past experience, so that the obtained rotation angle, the angular speed and the like are used as reference parameters (e.g., criteria of the rotation angle and angular speed) and stored in the database 300.

Figure 10B:
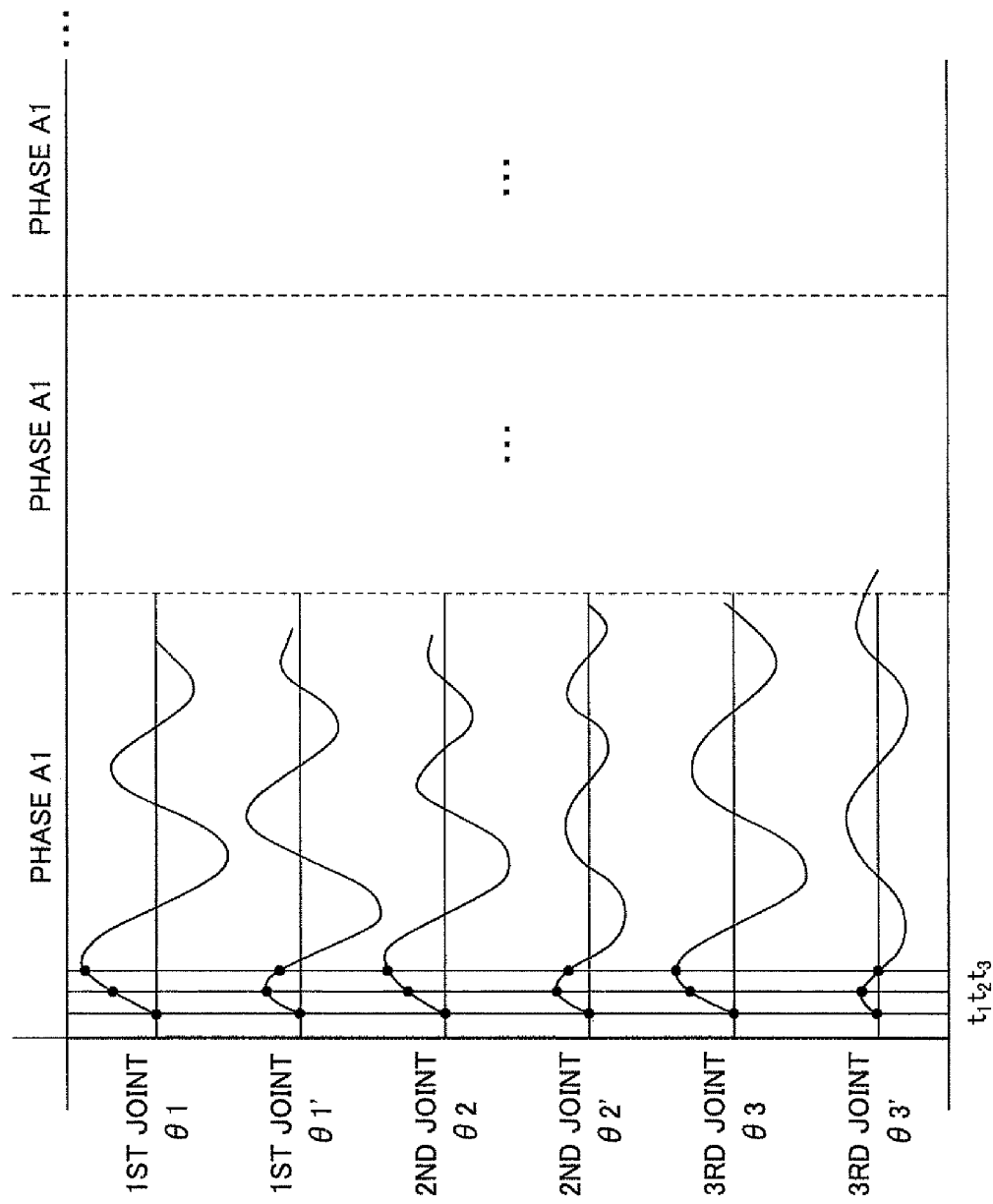
FIG. 10B is a schematic diagram for describing a process of estimating the task intended to be performed by the wearer and the phases included in the task by comparing physical quantities with respect to reference parameters.

FIG. 10A is a schematic diagram illustrating the tasks and phases stored in the database 300. FIG. 10B is a schematic diagram for describing a process of estimating the task intended to be performed by the wearer and the phases included in the task by comparing physical quantities with respect to reference parameters. The tasks and phases of FIGS. 10A and 10B are those illustrated in FIG. 9. Each of the illustrated task A, task B, task C ... includes a series of phases (e.g., phase A2, phase A3 ..., phase B1, phase B2, phase B3 ...).

When the wearer begins moving a finger joint, the measured physical quantity obtained from a detection signal from a physical quantity sensor (angle sensor 96, stress sensor 130) is compared with the reference parameter stored in the database 300. The comparison is described with reference to the graph illustrated in FIG. 10B. Although only the rotation angle $\theta 1$ and the angular speed $\theta 1'$ of the first joint of a finger, the rotation angle $\theta 2$ and the angular speed $\theta 2'$ of a finger, the rotation angle $\theta 3$ and the angular speed $\theta 3'$ are illustrated in the graph, other physical quantities are also to be compared.

The measured values of physical quantities during short time intervals are compared with reference parameters. The comparison process is performed on a series of phases of all of the tasks (A, B, C, ... ). In other words, all of the phases (A1, A2, A3, ..., B1, B2, B3, ..., C1, C2, C3 ... ) illustrated in FIG. 10A are extracted in a manner similar to a matrix and compared to measured physical quantities.

As illustrated in FIG. 10B, a phase having reference parameters matching all of the measure quantities can be identified by performing the comparison in correspondence with the time periods t1, t2, t3, .... In order to eliminate error of the matching, the identifying of phase may be performed after confirming that there is a match in plural time periods. For example, in FIG. 10B, it can be understood that the current movement is phase A1 when the measured quantities in plural time periods match the reference parameters of phase A1. It is, however, to be noted that the phase including reference parameters matching the measured quantities is not always necessarily the first phase of a task (e.g., not always A1, B1, C1).

Next, the steps performed in the control process executed by the control part 100B of the second embodiment are described with reference to the flowcharts of FIGS. 11A and 11B. The control part 100B reads a control program stored in the memory 102 and executes the control process of FIGS. 11A and 11B.

Figure 11B:
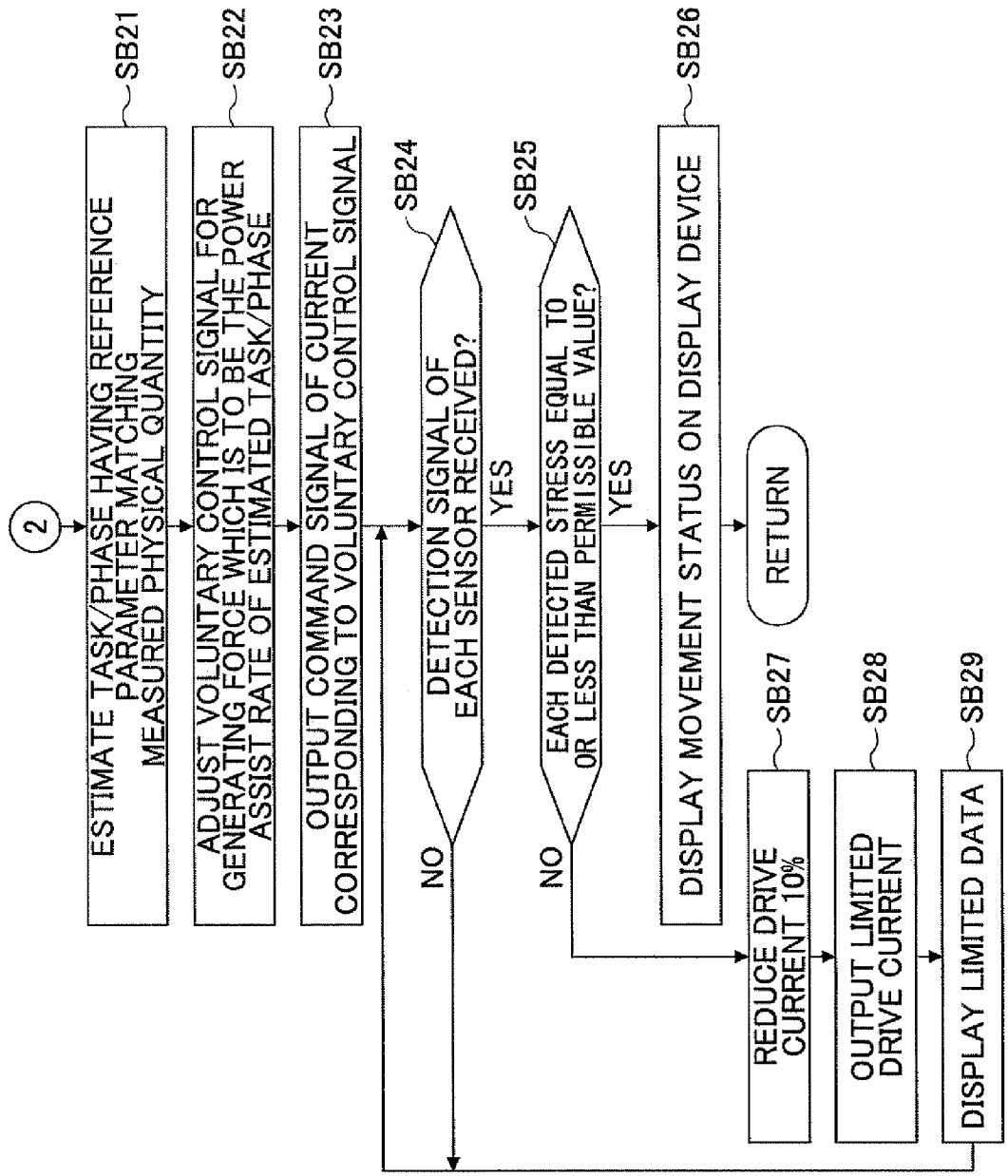
FIG. 11B is a flowchart for describing a second part of the steps performed in a control process executed by a control part 100B according to the second embodiment of the present invention.

It is to be noted that steps SB11, SB12, SB14-17, SB24-SB29 of FIGS. 11A and 11B are substantially the same as steps SA11-SA16 and SA19-SA24 and are not further described. Accordingly, steps SB13 and SB18-SB23 are mainly described.

In step SB13 of FIG. 11A, it is determined whether wireless detection signals are received from the torque sensor 94, the angle sensor 96, and the stress sensor 130 having detected corresponding physical quantities (torque, rotation angle, stress) in accordance with movements of the finger joints. When the detection signals of the torque sensor 94, the angle sensor 96, and the stress sensor 130 are received in step S13, the process proceeds to step S14.

In step SB18, the physical quantities (measured values) detected by the torque sensor 94, the angle sensor 96, and the stress sensor 130 are sequentially compared with reference parameters of each phase stored in the database 300. As described with reference to FIGS. 10A and 10B, because all of the tasks and the phases corresponding to the tasks are aligned in a matrix, the measured values of the physical quantities are sequentially compared with the reference parameters of each phase in an order such as A1, A2, A3 . . . , B1, B2, B3 . . . , C1, C2, C3 . . . . The reference parameters stored in the database 300 are set to avoid overlapping among all of the tasks and phases (hereinafter also simply referred to as "task/phase"). Thus, by performing comparisons with respect to the reference parameters of all of the tasks and phases, the tasks and phases including reference parameters matching the values of the measured physical quantities can be extracted.

Then, in step SB19, it is determined whether the physical quantities (measured values) of the torque sensor 94, the angle sensor 94, and the stress sensor 130 match the reference parameters of each phase stored in the database 300. In a case where there is no match, the process returns to step SB18 for repeating the processes performed in step SB18 and SB19. In a case where there is a match between the physical quantities (measured values) of the torque sensor 94, the angle sensor 94, and the stress sensor 130 and the reference parameters of each phase stored in the database 300, the process proceeds to step SB20. In step SB20, it is determined whether the number of times in which the physical quantities (measured values) of the torque sensor 94, the angle sensor 94, and the stress sensor 130 match the reference parameters of each phase stored in the database 300 has reached a predetermined number of times.

In a case where the number of times of the match has not reached the predetermined number of times in step SB20, the process returns to step SB18 for repeating the processes performed in steps SB18-SB20. In a case where the number of times of the match has reached the predetermined number of times in step SB20, the process proceeds to step SB21 of FIG. 11B. In step SB21, the tasks and phases corresponding to the reference parameters that match the values of the measured physical quantities are selected and the selected tasks and phases are estimated as the movement of the wearer.

Then, in step SB22, a power assistance rate assigned to the phase corresponding to the movement to be assisted is selected by referring to the database 300. Further, in step SB22, a voluntary control signal is adjusted to cause the electric motor 44 to generate motive power in accordance with the selected power assistance rate (voluntary assisting part).

Then, in step S23, an electric current (total current) corresponding to the voluntary control signal after the adjustment is generated and is output to the electric motor 44. Then, the same processes performed in step SA19-SA24 are performed in steps SB24-SB29.

With the control process of the second embodiment, the movement of the user and joints 20 can be estimated based on the physical quantities obtained from the torque sensor 94, the angle sensor 96, and the stress sensor 130, and a voluntary control signal can be generated in accordance with a power assist rate optimized with respect to each phase of the estimated movement. Because the electric motor 44 can apply motive power in correspondence with the voluntary control signal, the finger joints can be moved in the same manner as the movement of the fingers of an ordinary person. Accordingly, the wearer can smoothly move the fingers in a state where the movement assisting glove (as illustrated in FIGS. 1-3) is worn by the wearer.

Embodiment 3

Figure 12:
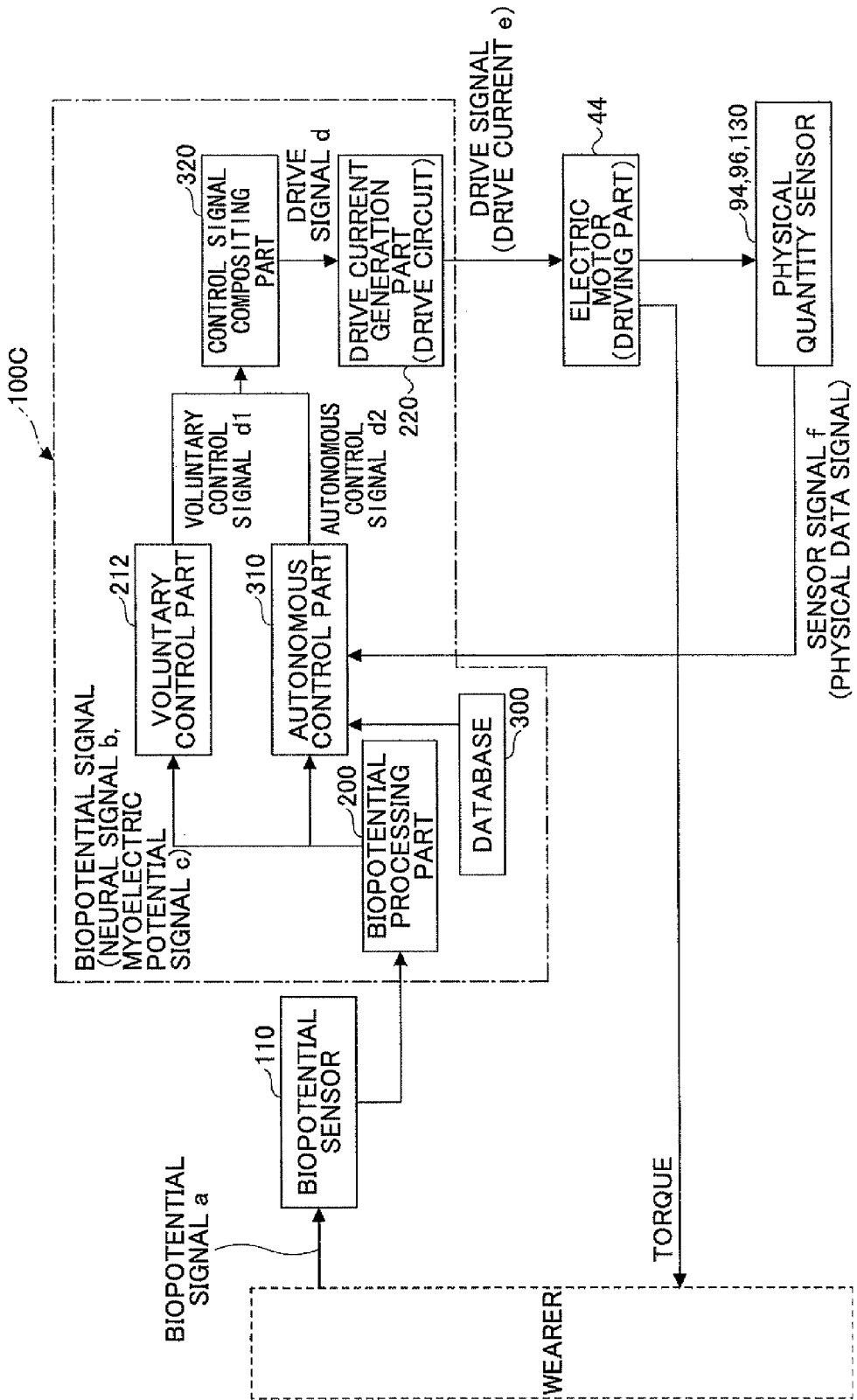
FIG. 12 is a schematic diagram for describing a signal process of a control part 100C according to the third embodiment of the present invention.

FIG. 12 is a schematic diagram for describing a signal process of a control part 1000 according to the third embodiment of the present invention. In the third embodiment, like components/elements are denoted with like reference numerals as those illustrated in FIGS. 5 and 8 of the first and second embodiments and are not further described.

The control part 100C of the third embodiment illustrated in FIG. 12 includes the biopotential process part 200, the voluntary control part 212, the database 300, an autonomous control part 310, a control signal compositing part 320, and the drive current generation part 220. Because the configuration of the movement assisting glove 20 of the third embodiment is the same as that of the first embodiment, the movement assisting glove 20 of the third embodiment is not further described. The control part 100C is an example of the control part 100 of FIG. 3.

The autonomous control part 310 estimates the task and phases of the wearer by receiving a detection signal f (physical data signal) from the torque sensor 94, the angle sensor 96, and the stress sensor 130 and comparing the detected values (physical quantities) of the torque sensor 94, the angle sensor 96, and the stress sensor 130 with the reference parameters stored in the database 300. Then, the autonomous control part 310 generates an autonomous control signal d2 for causing the electric motor 44 to generate a driving signal corresponding to the estimated task and phases. Further, the control signal compositing part 320 generates a control signal d by compositing the voluntary control signal d1 from the voluntary control part 212 and the autonomous control signal d2 from the autonomous control part 310.

More specifically, as illustrated in FIGS. 9, 10A, and 10B, when the movement assisting glove 20 (as illustrated in FIGS. 1-3) is worn by a wearer and the detection signals (physical quantities) of torque, rotation angle, and stress are received from the torque sensor 94, the angle sensor 96, and the pressure sensor 130, the autonomous control part 310 estimates the task and phases of the wearer by comparing the detection signals from the torque sensor 94, the angle sensor 96, and the stress sensor 130 with the reference parameters stored in the database 300 and generates an autonomous control signal d2 for causing the electric motor 44 to generate a driving signal corresponding to the estimated task and phases.

The control signal compositing part 320 makes composite the voluntary control signal d1 from the voluntary control part 212 and the autonomous control signal d2 from the autonomous control part 310. In autonomous control, a constant motive force is applied to, for example, each phase. Accordingly, the control signal d generated by the compositing in the control signal compositing part 320 causes the electric motor 44 to generate a motive force obtained by adding the motive force which changes from the start to the end of a movement in accordance with the voluntary control and the motive force which is constant with respect to each phase in accordance with the autonomous control.

Next, the steps performed in the control process executed by the control part 100C of the third embodiment are described with reference to the flowcharts of FIGS. 13A and 13B. The control part 100C reads a control program stored in the memory 102 and executes the control process of FIGS. 13A and 13B.

It is to be noted that steps SB11, SB12, SB14-17, SB24-SB29 of FIGS. 11A and 11B are substantially the same as steps SA11-SA16 and SA19-SA24 and are not further described. Accordingly, steps SB13 and SB18-SB23 are mainly described.

In step SC14 of FIG. 13A, a voluntary control signal d1 is generated by using the biopotential signal a detected by the biopotential sensors 61-65 for causing the electric motor 44 to generate a driving force in accordance with the intention of the user (voluntary control part). Similar to the above-described first and second embodiments, the voluntary control signal d1 is for generating a pulse current corresponding to a neural signal and a drive current corresponding to a myopotential signal.

In step SC18, the tasks and phases corresponding to the reference parameters that match the values of the measured are selected and the selected tasks and phases are estimated as the movement of the finger joints of the wearer. In addition, a hybrid ratio (voluntary control signal/autonomous control signal) corresponding to the estimated tasks and phases is defined. The hybrid ratio is set beforehand in correspondence with each task and phase so that the movement of the wearer can be assisted without causing discomfort to the wearer. When the phases are estimated in accordance with the comparison between the measured physical quantities by the torque sensor 94, the angle sensor 96, the stress sensor 130 and the reference parameters stored in the database 300, the control part 1000 automatically defines the hybrid ratio as described above.

Then, in step SC19, an autonomous control signal is generated for causing the electric motor 44 to generate a driving force corresponding to the estimated phases (autonomous control part).

Figure 13B:
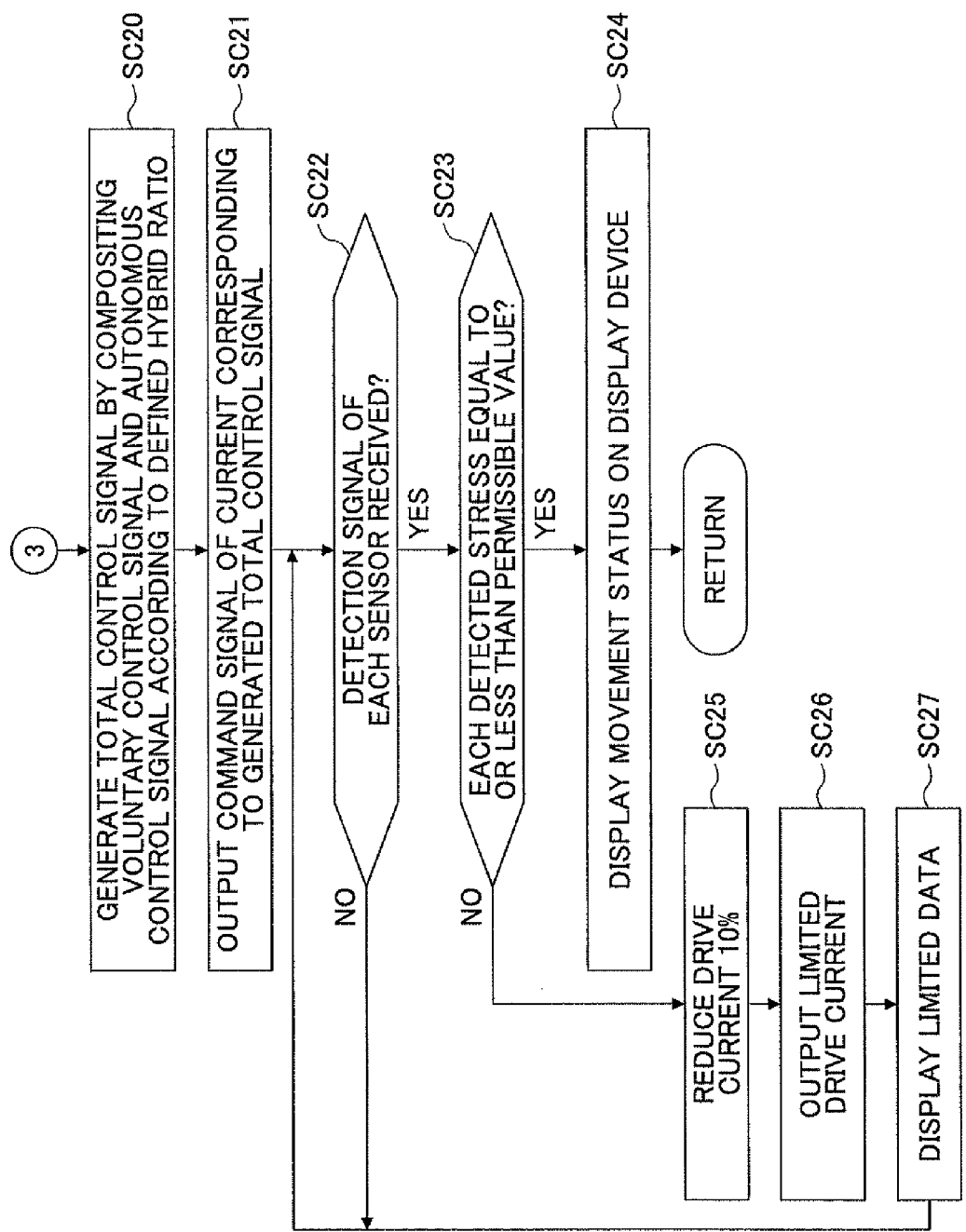
FIG. 13B is a flowchart for describing a second part of the steps performed in a control process executed by a control part 1000 according to the third embodiment of the present invention.

In step SC20 of FIG. 13B, the voluntary control signal d1 and the autonomous control signal d2 are made composite in accordance with the defined hybrid ratio, to thereby generate a total control signal d (control signal compositing part).

Further, in step SC21, a command signal corresponding to the drive current e is generated in accordance with the total control signal d. The total control signal d is generated to satisfy a predetermined hybrid ratio obtained from the proportion between the voluntary control signal and the autonomous control signal. Accordingly, the electric motor 44 of the movement assisting glove 20 can generate a driving force corresponding to the voluntary control signal and the autonomous control signal by being supplied with the drive current e corresponding to the total control signal. Thus, the finger joints can be moved in the same manner as the movement of the fingers of an ordinary person. Accordingly, the wearer can smoothly move each finger in a state where the movement assisting glove 20 (as illustrated in FIGS. 1-3) is worn by the wearer.

Embodiment 4

Figure 14:
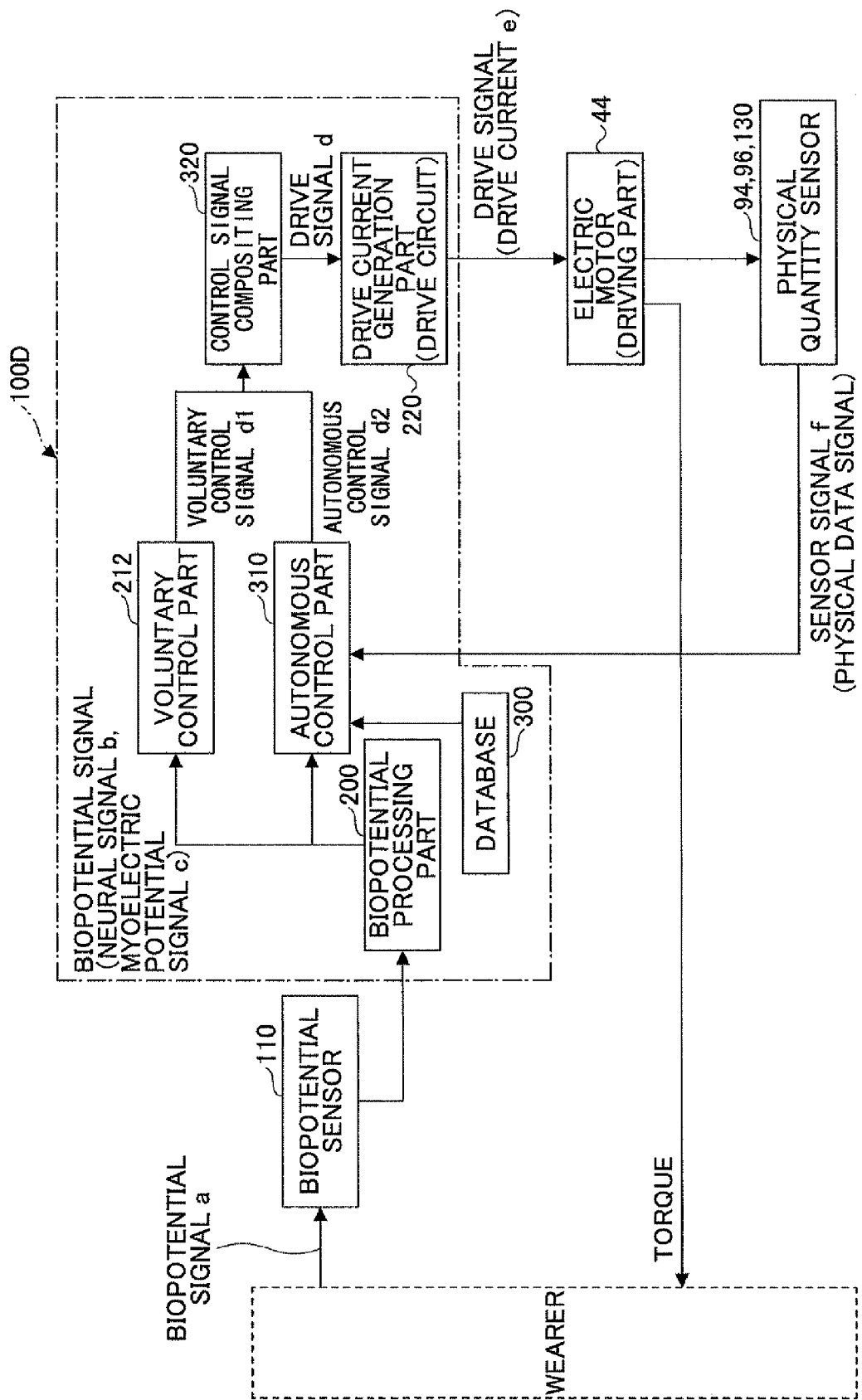
FIG. 14 is a schematic diagram for describing a signal process of a control part 100D according to the fourth embodiment of the present invention.

FIG. 14 is a schematic diagram for describing a signal process of a control part 100D according to the fourth embodiment of the present invention. In the fourth embodiment, like components/elements are denoted with like reference numerals as those illustrated in FIGS. 5, 8, and 12 of the first-third embodiments and are not further described.

The control part 100D of the fourth embodiment illustrated in FIG. 14 includes the biopotential process part 200, the voluntary control part 212, the database 300, the autonomous control part 310, the control signal compositing part 320, and the drive current generation part 220. Because the configuration of the movement assisting glove 20 of the fourth embodiment is the same as that of the first embodiment, the movement assisting glove 20 of the fourth embodiment is not further described. The control part 100D is an example of the control part 100 of FIG. 3.

The voluntary control part 212 and the autonomous control part 310 of the control part 100D have a function of estimating the tasks and phases of finger joint movements intended by the wearer by comparing detected values (physical quantities) from the torque sensor 94, the angle sensor 96, and the stress sensor 130 and the reference parameters stored in the database 300 and generating a voluntary control signal d1 and the autonomous control signal d2 that satisfy the hybrid ratio and a power assist rate corresponding to the estimated phases.

Accordingly, the voluntary control part 212 generates a control signal for controlling the driving of the electric motor 44 of the movement assisting glove 20 based on neural signals and myopotential signals. Further, the voluntary control part 212 estimates the tasks and phases based on the physical quantities from the torque sensor 94, the angle sensor 96, and the stress sensor 130 along with the database 300 and generates a control signal for causing the electric motor 44 to generate a driving force that satisfies a power assist rate corresponding to the estimated phases.

Next, the steps performed in the control process executed by the control part 100D of the fourth embodiment are described with reference to the flowcharts of FIGS. 15A and 15B. The control part 100D reads a control program stored in the memory 102 and executes the control process of FIGS. 15A and 15B.

Figure 15A:
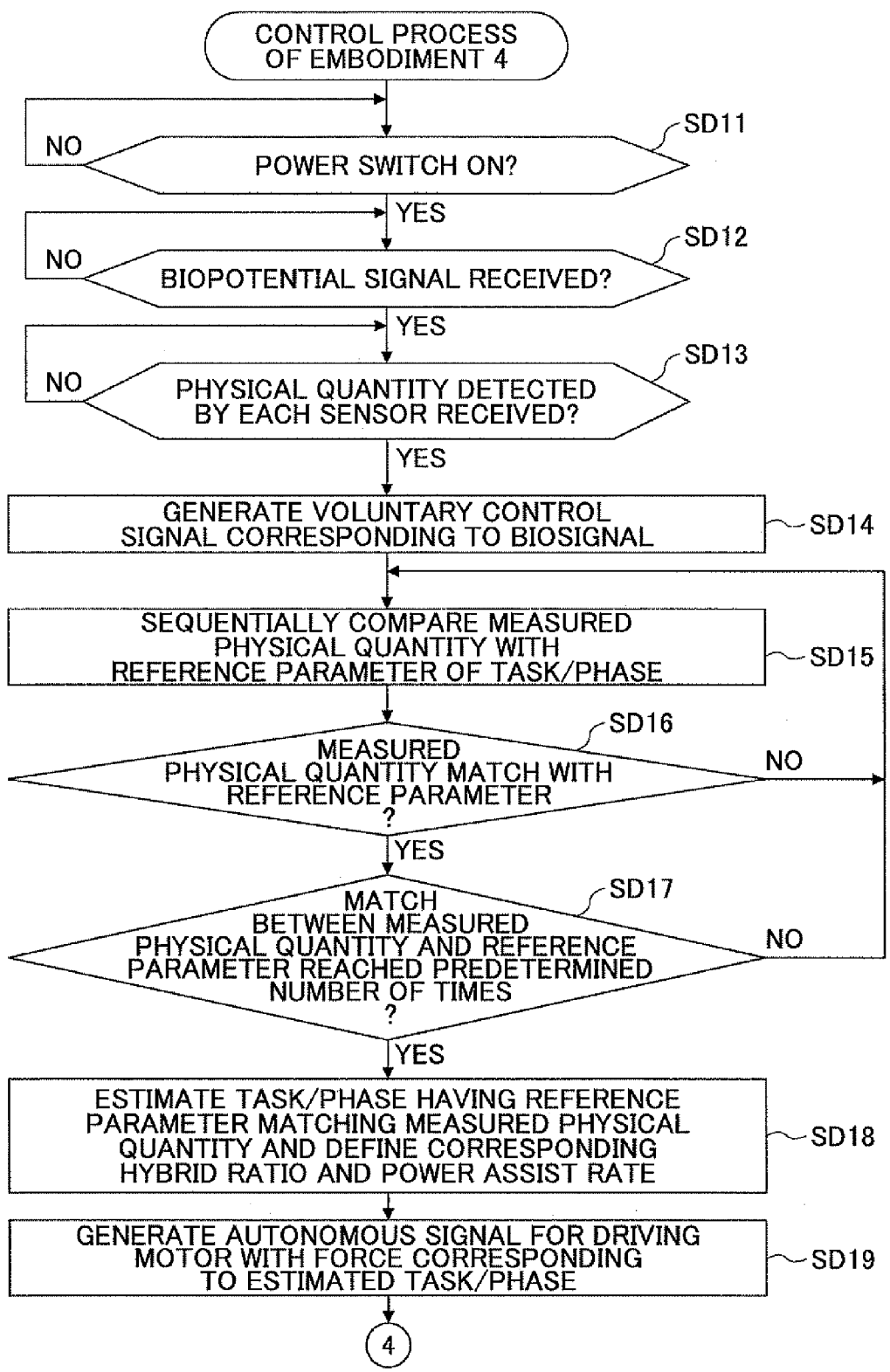
FIG. 15A is a flowchart for describing a first part of the steps performed in a control process executed by a control part 100D according to the fourth embodiment of the present invention.
Figure 15B:
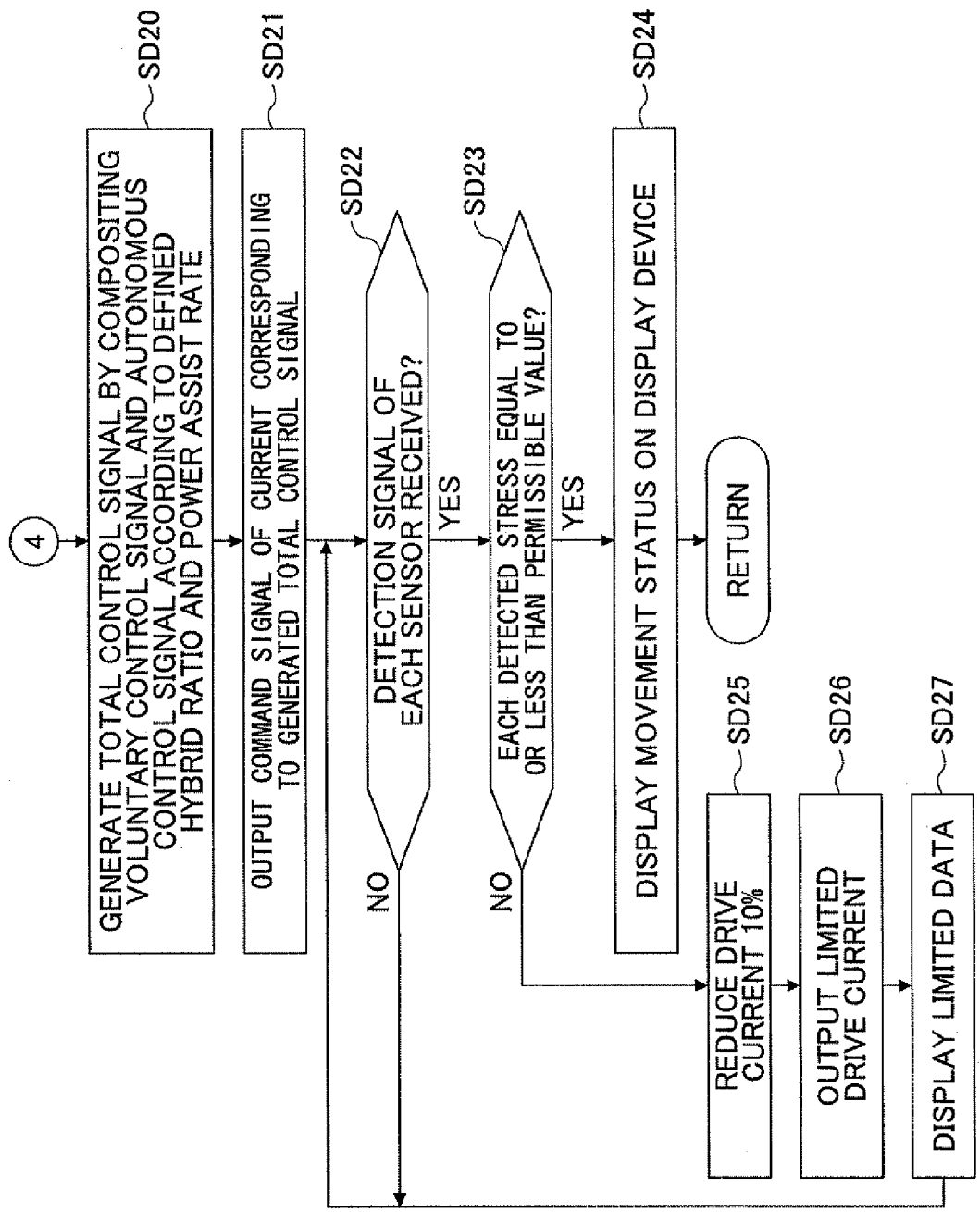
FIG. 15B is a flowchart for describing a second part of the steps performed in a control process executed by a control part 100D according to the fourth embodiment of the present invention.

It is to be noted that steps SD11-SD17, SD21-SD27 of FIGS. 15A and 15B are substantially the same as steps SC11-SC17 and SC21-SC27 of FIGS. 13A and 13B and are not further described. Accordingly, steps SD18-SD20 are mainly described.

In step SD18 of FIG. 15A, the tasks and phases corresponding to the reference parameters that match the values of the measured are selected and the selected tasks and phases are estimated as the movement of the finger joints of the wearer. In addition, a hybrid ratio (voluntary control signal/autonomous control signal) corresponding to the estimated tasks and phases is defined. Furthermore, a power assist rate, which is assigned to a phase corresponding to the movement to be assisted, is defined by referring to the database 300.

Then, in step SD19, an autonomous control signal is generated for driving the electric motor 44 to generate a motive force corresponding to the estimated phase.

Figure 20:
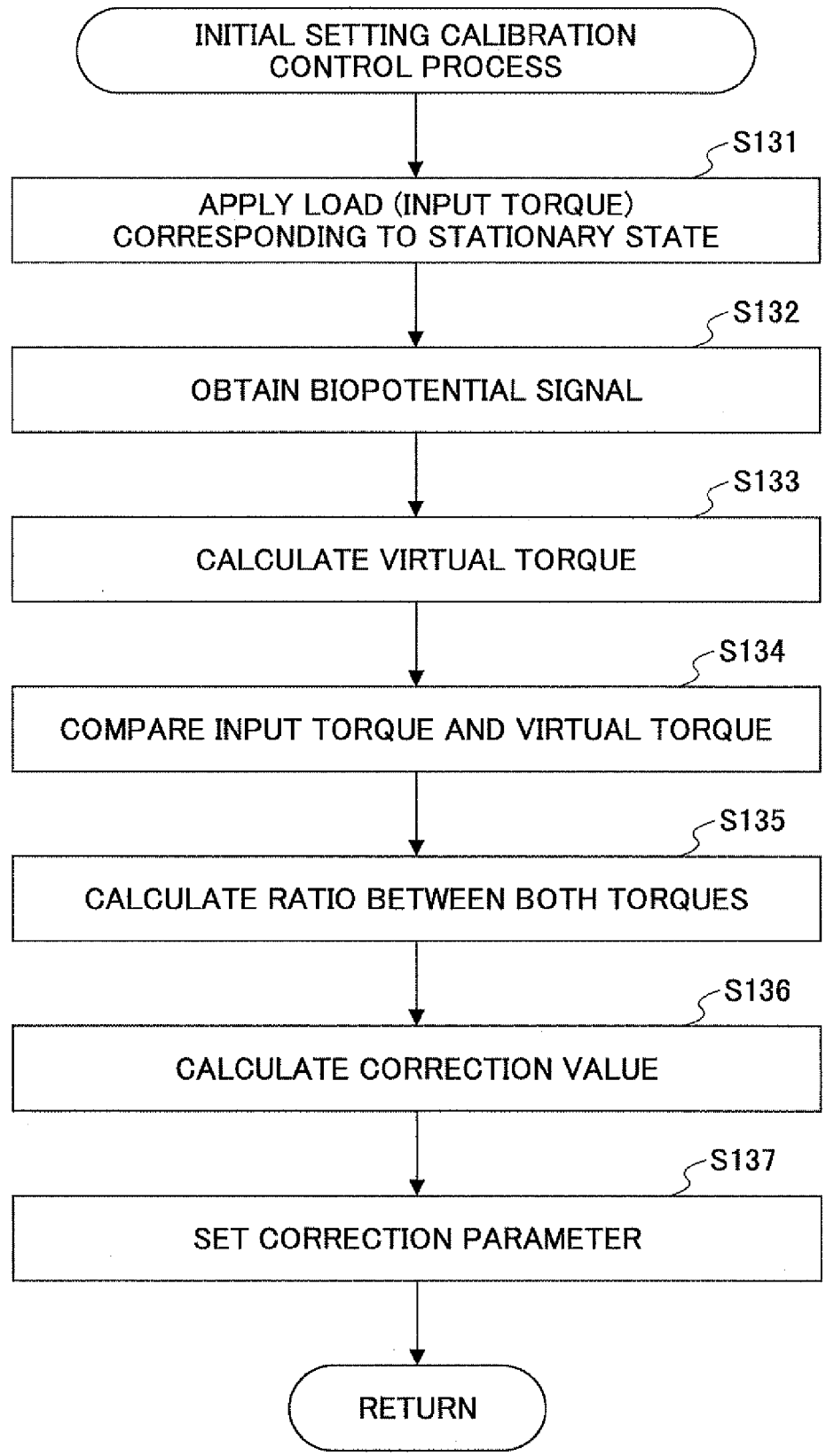
FIG. 20 is a flowchart illustrating processes performed in controlling calibration performed for the first time where initial settings are performed.

Then, in step SD20 of FIG. 20, the voluntary control signal d1 and the autonomous control signal d2 are made composite in accordance with defined hybrid ratio and the power assist rate, to thereby generate a total control signal d. Thereby, in step SD21, a command signal corresponding to the drive current e is generated in accordance with the total control signal d obtained by compositing the voluntary control signal d1 and the autonomous control signal d2 in accordance with the defined hybrid ratio and the power assist rate.

Accordingly, the electric motor 44 of the movement assisting glove 20 (as illustrated in FIGS. 1-3) can generate a driving force corresponding to the voluntary control signal and the autonomous control signal by being supplied with the drive current e corresponding to the total control signal in accordance with the defined hybrid ratio and the power assist rate. Thus, the finger joints can be moved in the same manner as the movement of the fingers of an ordinary person. Accordingly, the wearer can smoothly move each finger in a state where the movement assisting glove 20 (as illustrated in FIGS. 1-3) is worn by the wearer.

Embodiment 5

Figure 16:
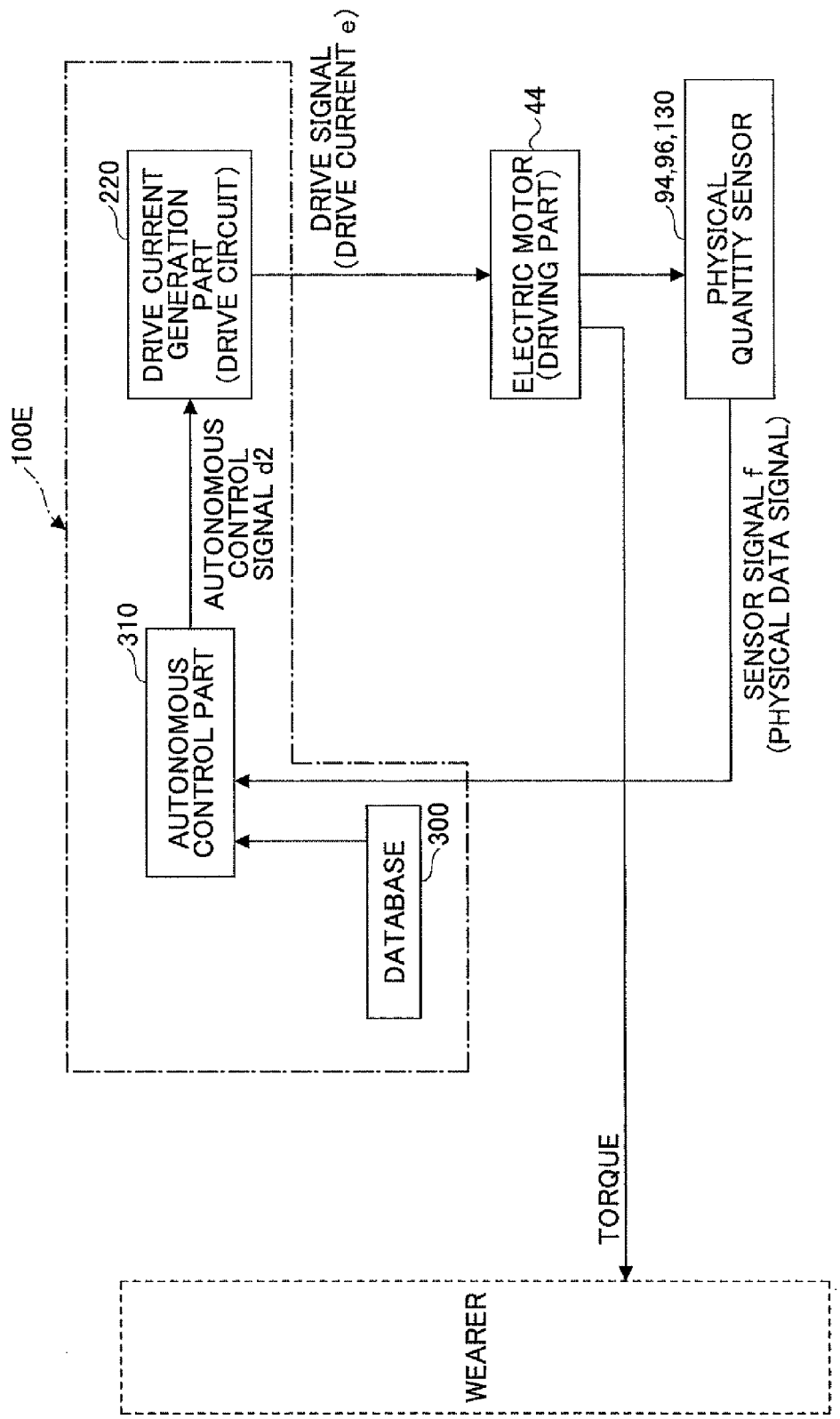
FIG. 16 is a schematic diagram for describing a signal process of a control part 100E according to the fifth embodiment of the present invention.

FIG. 16 is a schematic diagram for describing a signal process of a control part 100E according to the fifth embodiment of the present invention. In the fifth embodiment, like components/elements are denoted with like reference numerals as those illustrated in FIGS. 5, 8, 12, and 14 of the first-fourth embodiments and are not further described.

The fifth embodiment is a control system applicable to a case where a biosignal "a" cannot be obtained from a wrist of the wearer. The control system controls the driving force of the electric motor 44 of the movement assisting glove 20 (as illustrated in FIGS. 1-3) without using the biopotential sensors 61-65. Because the configuration of the movement assisting glove 20 of the fifth embodiment is the same as that of the first embodiment, the movement assisting glove 20 of the fifth embodiment is not further described. The control part 100E of FIG. 16 is an example of the control part 100 of FIG. 3.

The control part 100E of the fifth embodiment includes the database 300, the autonomous control part 310, and the drive current generation part 220. Because a biopotential signal "a" cannot be obtained from the wearer, the control part 100E does not include the voluntary control part 212. Instead, an autonomous control signal d2 generated by the autonomous control part 310 is supplied to the drive current generation part 220.

The autonomous control part 310 estimates the tasks and phases of finger joint movements intended by the wearer by comparing detected values (physical quantities) from the torque sensor 94, the angle sensor 96, and the stress sensor 130 and the reference parameters stored in the database 300, and generates an autonomous control signal d2 that satisfies the hybrid ratio and a power assist rate corresponding to the estimated phases. Accordingly, the driving current generation part 220 generates a current corresponding to the autonomous control signal d2 and supplies the current to the electric motor 44.

Next, the steps performed in the control process executed by the control part 100E of the fifth embodiment are described with reference to the flowcharts of FIGS. 17A and 17B. The control part 100E reads a control program stored in the memory 102 and executes the control process of FIGS. 17A and 17B.

Figure 17A:
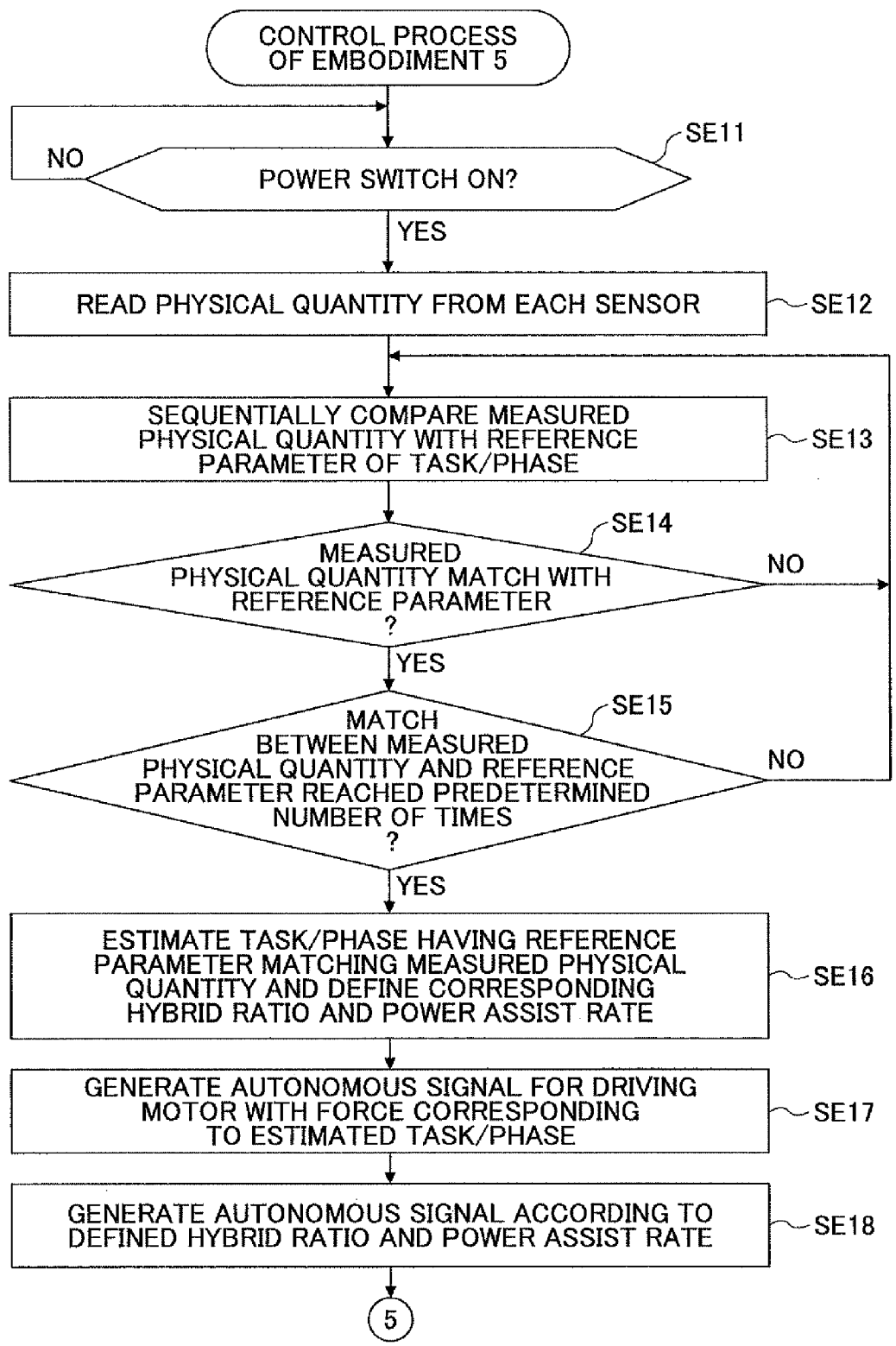
FIG. 17A is a flowchart for describing a first part of the steps performed in a control process executed by a control part 100E according to the fifth embodiment of the present invention.
Figure 17B:
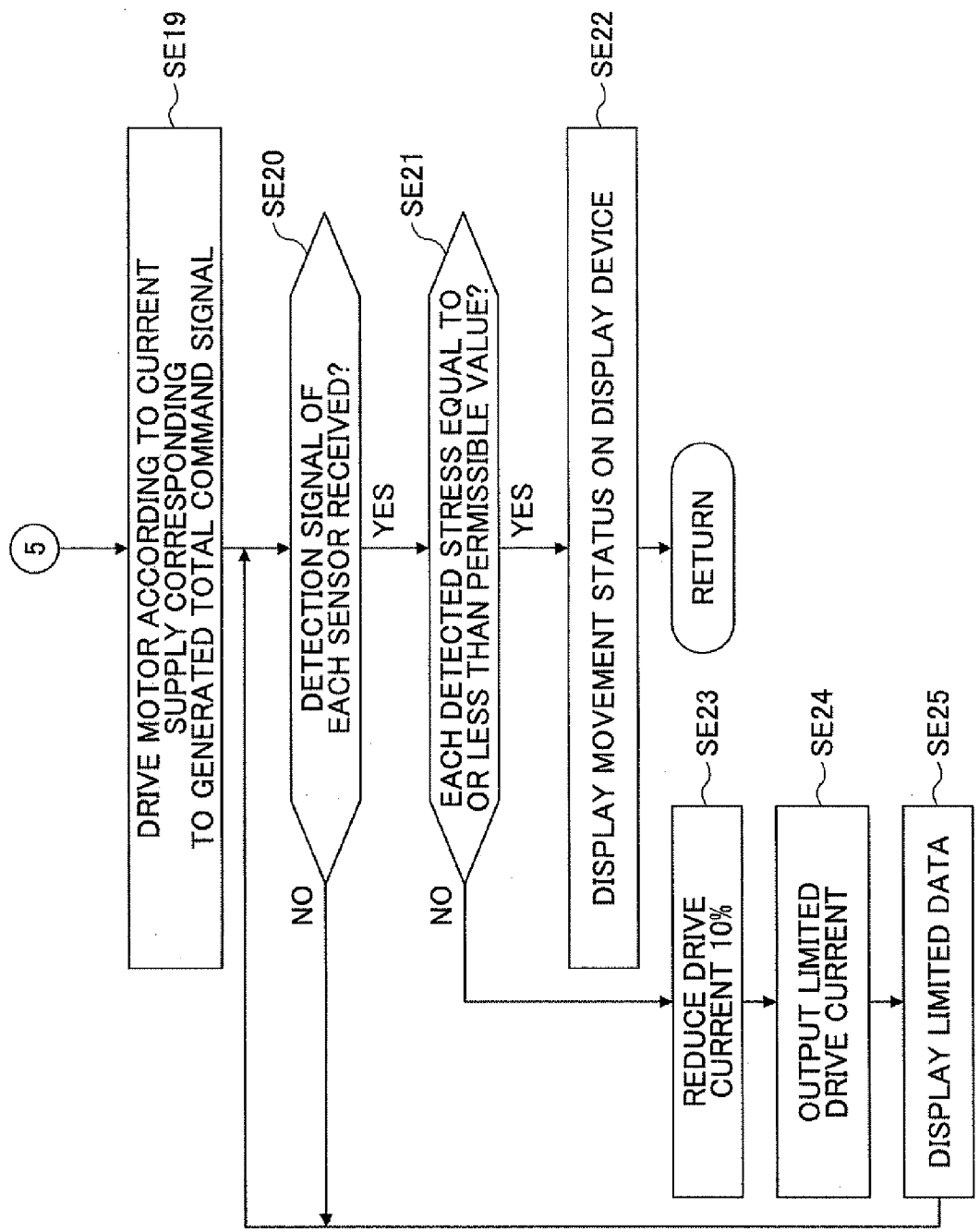
FIG. 17B is a flowchart for describing a second part of the steps performed in a control process executed by a control part 100E according to the fifth embodiment of the present invention.

It is to be noted that steps SE11-SE25 of FIGS. 17A and 17B are substantially the same as all of the steps of FIGS. 15A and 15B except for steps SD12 and SD14 and are not further described. In this embodiment, step SE18 is described.

In step SE18, the autonomous control signal d2 is generated in accordance with the defined hybrid ratio and the power assist rate. Accordingly, the electric motor 44 can generate a motive force in accordance with the defined hybrid ratio and power assist rate.

Accordingly, in a case where a biopotential signal "a" cannot be obtained from a wrist of the wearer, the control part 100E of the fifth embodiment can smoothly move the finger joints because a driving force can be obtained from the electric motor 44 of the movement assisting glove 20 in correspondence with an autonomous signal generated by the autonomous control part 310. Accordingly, the wearer can smoothly move each finger in a state where the movement assisting glove 20 (as illustrated in FIGS. 1-3) is worn by the wearer.

Embodiment 6

Figure 18:
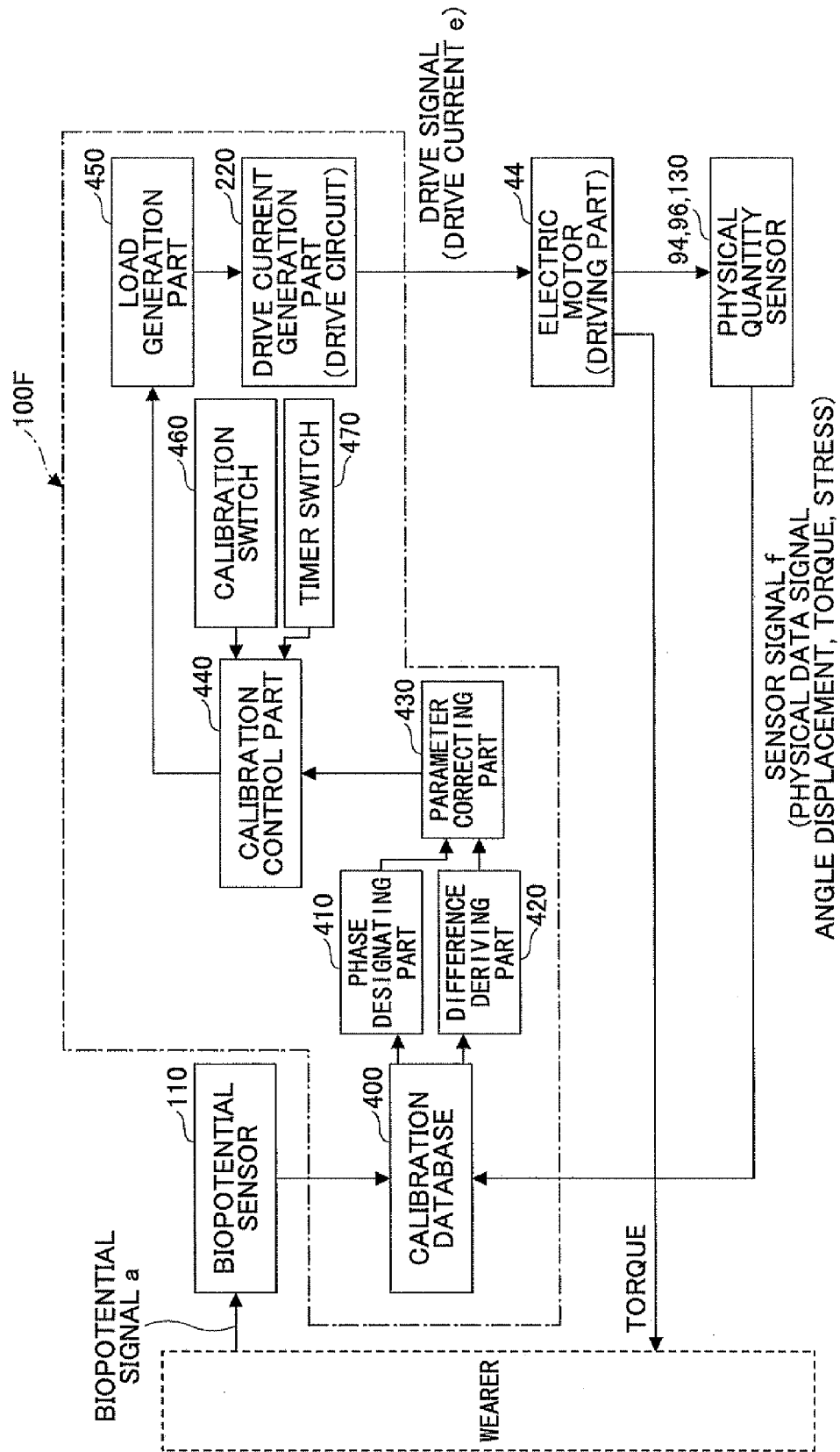
FIG. 18 is a schematic diagram for describing a signal process of a control part 100F according to the sixth embodiment of the present invention.

FIG. 18 is a schematic diagram for describing a signal process of a control part 100F according to the sixth embodiment of the present invention. In the sixth embodiment, like components/elements are denoted with like reference numerals as those illustrated in FIGS. 5, 8, 12, 14, and 16 of the first-fifth embodiments and are not further described.

In addition to the above-described drive current generation part 220, the control part 100F also includes a calibration database 400, a phase identifying part 410, a difference deriving part 420, a parameter correcting part 430, a calibration control part 440, and a load generation part 450. Because the configuration of the movement assisting glove 20 of the sixth embodiment is the same as that of the first embodiment, the movement assisting glove 20 of the sixth embodiment is not further described. The control part 100F of FIG. 18 is an example of the control part 100 of FIG. 3.

The calibration database 400 is a data storage part used for correcting a parameter of a control signal in correspondence with a myopotential (biopotential) signal detected (sensed) with respect to a myodynamia (muscular force) generated by the wearer.

In other words, the calibration database 400 includes a first storage space for storing beforehand a first corresponding relationship between a myodynamia and a myopotential signal (biopotential signal) that are generated from the wearer wearing the movement assisting glove 20 on a hand and a second storage space for storing beforehand a second corresponding relationship of a myodynamia and a myopotential signal (biopotential signal) that are generated in correspondence with joint angles that change when the wearer performs a basic movement of a finger joint.

The joint angle detected by each of the physical quantity sensors and the myopotential signal detected by the biopotential sensors 61-65 are input to the calibration database 400.

Then, after the movement assisting glove 20 is attached to the joints of the wearer, the calibration control part 440 corrects an auxiliary motive force generated by the electric motor 44 in correspondence with a biopotential signal when the wearer performs a basic movement of a finger joint and the second corresponding relationship, so that the auxiliary motive force satisfies the first corresponding relationship.

In other words, when the wearer wears the movement assisting glove 20 and switches on the movement assisting glove 20, the calibration control part 440 performs a calibration control process and causes the load generating part 450 to apply a load (input torque) to each finger joint of the wearer step-by-step by causing the electric motor 44 to apply a driving force via the drive current generation part 220, to thereby cause the wearer to generate a myodynamia (muscular force) in each finger joint in a manner countering (antagonizing) the driving force.

Then, each finger joint having the driving force applied from the electric motor 44 generates a myodynamia (muscular force) by performing a predetermined calibration movement (e.g., task A: extending of finger). Then, the angle sensor 96 detects joint angles and the myopotential sensors 61-65 detect myopotential signals of the wrist along with the performing of the calibration movement.

Then, the phase identifying part 410 identifies a phase(s) corresponding to the pattern of the calibration movement of the wearer by comparing the joint angles detected by the angle sensor 96 and the joint angles stored in the calibration database 400.

Further, when the calibration control process is started, the difference deriving part 420 obtains the above-described second corresponding relationship by comparing the load of the electric motor 44 (input torque) applied from the load generation part 450 and the myodynamia (estimated torque) corresponding to a detected myopotential signal (measured value) of the upper arm from the biopotential sensors 61-65 and obtaining the difference between the input torque and the estimated torque.

Further, the parameter correcting part 430 corrects a parameter K in order to satisfy the above-described first corresponding relationship based on the difference between the load (input torque) and the myodynamia (estimated torque) obtained by the difference deriving part 420 with respect to the phase identified by the phase identifying part 410. In a case where there is no difference between the input torque of the electric motor 44 applied from the load generation part 450 and the myodynamia corresponding to the myopotential signal (measured value) detected from the biopotential sensors 61-65, the parameter K is not corrected.

On the other hand, in a case where there is a difference between the input torque of the electric motor 44 applied from the load generation part 450 and the myodynamia corresponding to the myopotential signal (measured value) detected from the biopotential sensors 61-65, the parameter K is corrected so that the input torque and the myodynamia match. In such case, the corrected parameter K' is set so that the input torque and the estimated torques become equal.

Then, the calibration control part 440 sets the parameter corrected by the parameter correcting part 430 as the parameter of the wearer and performs calibration on the next phase.

Accordingly, by using the parameters set by the calibration, the electric motor 44 can be controlled so that an assisting force corresponding to a biopotential signal detected from the biopotential sensors 61-65 can be generated. Accordingly, the power assist rate can be controlled to maintain a predetermined value regardless of, for example, a daily condition of the wearer (e.g., resistance value of skin, status of biopotential) and regardless of whether the positions of the biopotential sensors 61 are deviated.

Further, the joint angles detected by the angle sensor 96 and the myopotential signals detected by the biopotential sensors 61-65 are supplied to the control part 100F. Further, the driving force of the electric motor 44 to be applied in each phase in correspondence with the joint angles and the myopotential signals are calculated by using the corrected parameter K' set by the calibration control part 440. Further, control signals obtained from the calculation results are supplied to the drive current generation part 220.

Further, the calibration control part 440 may perform the calibration control process whenever the power of a remote controller is switched on. Alternatively, by providing a calibration switch 460 dedicated for calibration, the user himself/herself may operate the calibration control process. Further, by providing a timer switch 470, the calibration control process can be automatically performed at a predetermined time (e.g., every morning at 8 o'clock or on Mondays at 8 o'clock).

It is preferable for the calibration control process to be frequently performed for correcting motive force when the wearer practices moving the movement assisting glove 20. In a case where 1 week or more has passed since practice is started, the calibration control process may be discretionally performed at a given time. Accordingly, whether to use the power switch, the calibration switch 460, or the timer switch 470 may be determined depending on the number of times of use (number of times of practice). Alternatively, the calibration switch 460 or the timer switch 470 may be discretionally operated.

Next, the steps performed in the control process executed by the control part 100F of the sixth embodiment are described with reference to the flowchart of FIG. 19.

Figure 19:
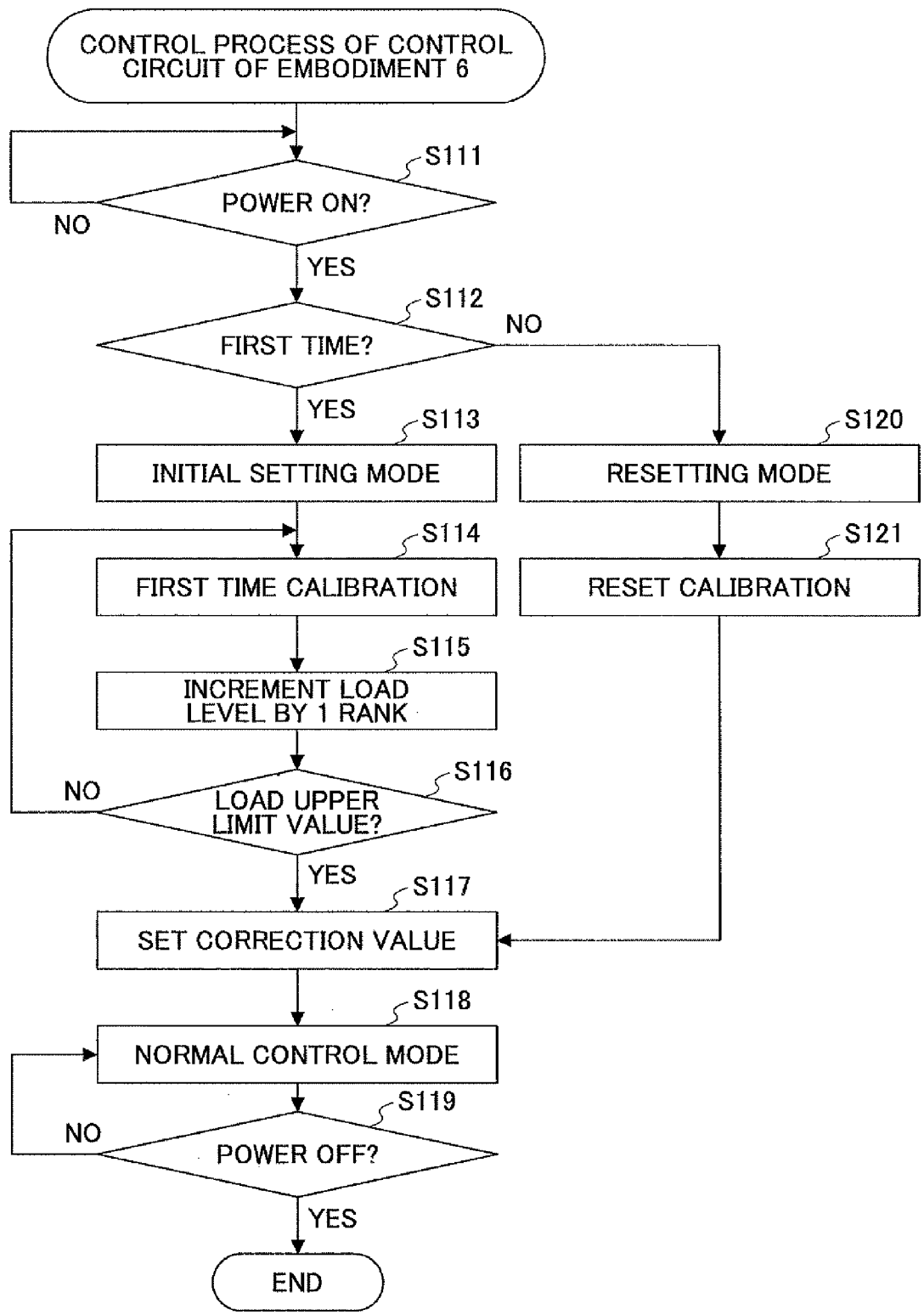
FIG. 19 is a flowchart for describing steps performed in a control process executed by a control part 100F according to the sixth embodiment of the present invention.

As illustrated in FIG. 19, the control part 100F proceeds to performing step S112 when the power is switched on after the movement assisting glove 20 (as illustrated in FIGS. 1-3) in step S111. In step S112, it is determined whether the power is switched on for the first time. In a case where it is the first time in step S112, the process proceeds to an initial setting mode in step S113 and further proceeds to the execution of an initial setting calibration process (calibration part).

In other words, in step S114, a correction value is obtained based on a received biopotential signal detected from the biopotential sensors 61-65 in response to a driving force applied as a load from the electric motor 44 of the movement assisting glove 20. In step S115, the load is increased by incrementing the voltage applied to the electric motor 44 by 1 rank. Then, in step S116, it is determined whether the load has reached a predetermined upper limit value. In a case where the load has not reached the upper limit value in step S116, the process returns to step S114 to repeat the processes performed in steps S114-S116.

In a case where the load has reached the upper limit value in step S116, the process proceeds to step S117 for setting a parameter K' obtained by the calibration.

Then, in step S117, a correction value (parameter K') is set in correspondence with a myodynamia of the wearer obtained when calibration is performed in a state where the wearer wearing the movement assisting glove 20 is in a non-moving state (correction value setting part). That is, in step S115, the parameter K is obtained so that the value of the surface myopotential value becomes 1 when 1 Nm of force is exerted in a case where the finger joint is in a non-moving (stationary) extended state. In the first calibration, the driving force (torque τm) of the electric motor 44 is applied as a load step-by-step to each finger joint of the wearer whereas a myodynamia that counters (antagonizes) the driving force is generated in each finger joint of the wearer.

Accordingly, a biopotential signal generated in response to the driving force applied from the driving motor 44 is detected by the biopotential sensors 61-65. Then, a parameter for calculation is generated based on the detected signal. Then, the parameter is stored as a correction value unique to the wearer inside the calibration database 400.

Accordingly, based on a corresponding relationship between the motive force and the biopotential signal generated when the wearer performs a predetermined basic movement (calibration movement) immediately after the movement assisting glove 20 is worn by the wearer, the driving force of the electric motor 44 is corrected in correspondence with a biosignal satisfying the corresponding relationship between the motive force and the biopotential signal of the wearer.

Then, the process proceeds to step S118 for shifting to a control mode that executes a normal control mode. Then, in step S119, the normal control mode is continued until the power is switched off.

Further, in a case where the power is switched on 2 times or more in step S112, the process proceeds to step S120. Then, in step S121, the wearer performs a correction value setting calibration (calibration part) based on a single motion (a one time movement). Further, in step S121, a correction value (parameter K') corresponding to a myodynamia of the wearer obtained in accordance with a predetermined calibration movement is set (correction value setting part). Then, the processes of steps S117-S119 are performed.

Although calibration is performed based on a single motion in a case where the power is switched on 2 times or more in the above-described embodiments, the correction value setting calibration may be performed in the same non-moving state as the first time in the case where the power is switched on 2 times or more.

Next, control processes corresponding to each correction value setting mode is described with reference to FIGS. 20-22.

FIG. 20 is a flowchart illustrating processes performed in controlling calibration performed for the first time where initial settings are performed. In a case of performing calibration for the first time, correction values are set by generating a myodynamia for maintaining the joints in a stationary state in response to the load applied from the motor.

As illustrated in FIG. 20, in step S131, the control part 100F causes the electric motor 44 to apply a driving force (input torque) as a load by supplying a predetermined driving current to the electric motor 44 where the finger joints are maintained in a stationary state. Accordingly, the wearer generates myodynamia countering the driving force of the electric motor 44 while maintaining, for example, the finger joints in an extended state.

Then, in step S132, myopotential signals (biopotential signals) of the wearer's wrist which are detected from the biopotential sensors 61-65 are obtained. Then, in step S133, a virtual torque is estimated by performing calculation based on the measured myopotential signals.

Then, in step S134, the input torque being applied as a load is compared with the virtual torque. Then, in step S135, the ratio between the input torque and the virtual torque are calculated. Then, in step S136, the correction value (correction parameter) of the control signal to be supplied to the drive current generation part 220 is calculated by reading out the parameters of load stored in the calibration database 400 in correspondence with each phase and multiplying the read out parameters with the ratio between the input torque and the virtual torque. Then, in step S137, the correction parameter is set as a parameter of the autonomous control (correction value setting part).

Accordingly, the wearer having the movement assisting glove 20 attached to the joints can automatically perform calibration of biosignals in correspondence with everyday conditions of the wearer while maintaining a stationary state. Therefore, time and effort required for calibration can be significantly reduced.

Further, the calibration can be performed even for a wearer having weakened muscles with applying excessive workload to the wearer. The correction value can be set in correspondence with the condition of the wearer. Thus, a driving force can be accurately applied in cooperatively with the movement of the wearer based on myopotential signals of the wearer.

Accordingly, an assisting force complying with the intentions of the wearer can be applied from the electric motor 44 when performing the calibration. Thus, too much or too little assisting force can be prevented from being applied. As a result, reliability of the movement assisting glove 20 can be increased by consistently assisting the movement of the wearer.

Even in a situation where it is difficult for the wearer to use the movement assisting glove 20 (e.g., a situation where the user is a beginner), the wearer can comfortably perform calibration.

Next, a control process corresponding to a calibration resetting mode 1 (see step S120 of FIG. 19) is described with reference to FIG. 21.

Figure 21:
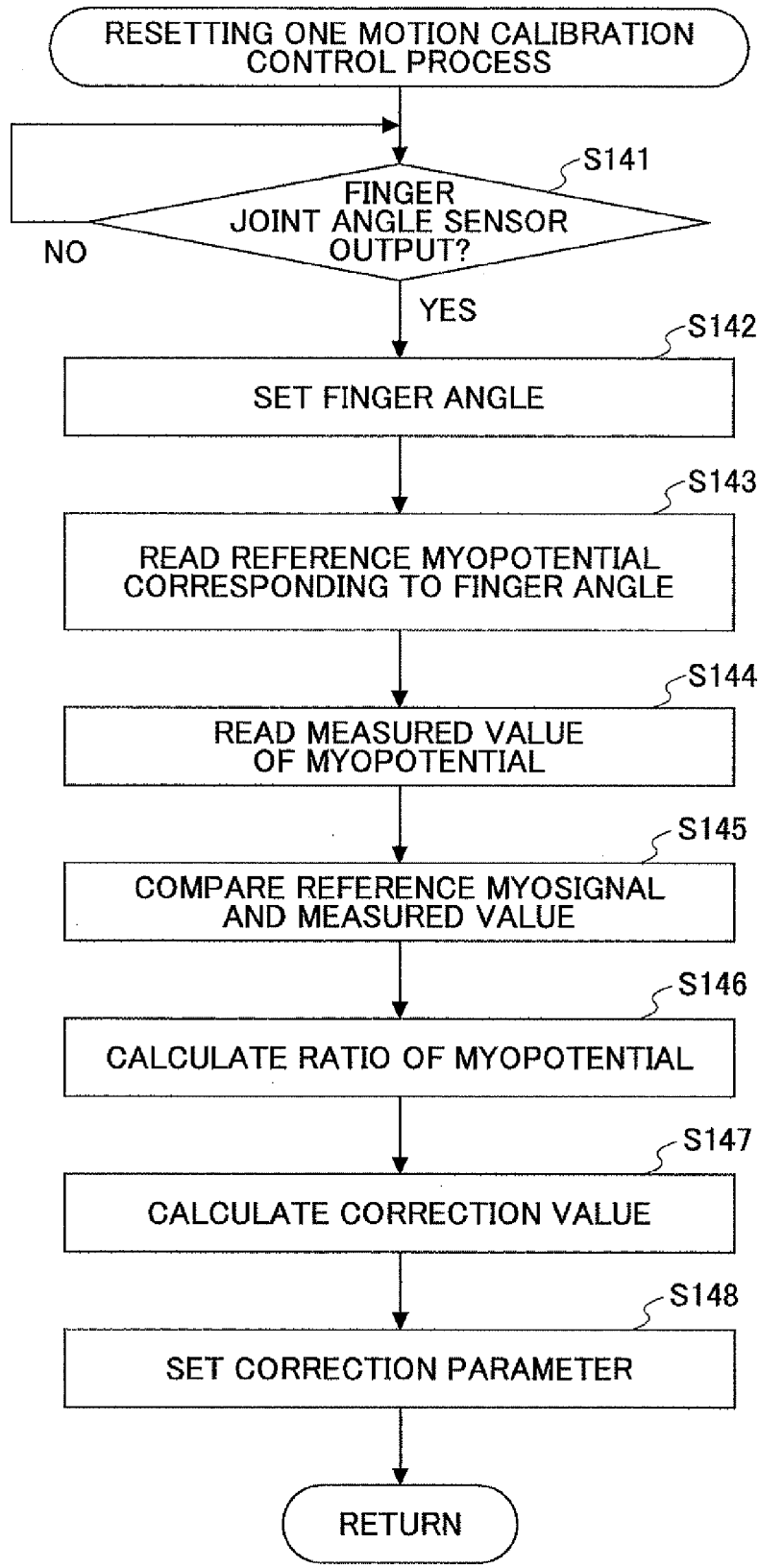
FIG. 21 is a flowchart illustrating processes performed in controlling resetting calibration based on a single motion (one time movement)

FIG. 21 is a flowchart illustrating processes performed in controlling resetting calibration based on a single motion (one time movement). In a case of performing calibration based on a single motion, the wearer moves a finger from an extended state to a bent state for a single time. Further, myopotentials corresponding to calibration movements are stored beforehand in the memory 102.

As illustrated in FIG. 21, the control part 100F determines whether a detection signal from the angle sensor 96 of a joint is output in step S141. In a case where the angle sensor 96 detects a change of angle of the finger joint in correspondence with the movement of the finger joint of the wearer, the process proceeds to step S142. In step S142, the movement angle of each finger joint is set based on the detection signal from the angle sensor 96.

Then, in step S143, reference myopotentials corresponding to movement angles of the finger joints are read out from the memory 102. Then, in step S144, measured values of myopotentials of the wrist of the wearer are read out from the biopotential sensors 61-65. Then, in step S145, the reference myopotentials and the measured values of myopotentials are compared.

Then, in step S146, the ratio between the reference myopotentials and the measured values of myopotentials are calculated. Then, in step S147, the correction value (correction parameter) of the control signal to be supplied to the drive current generation part 220 is calculated by reading out parameters stored in correspondence with movement angles of finger joints in the calibration database 400 and multiplying the read out parameters with the ratio between the reference myopotentials and the measured values of myopotentials. Then, in step S148, the correction parameter is set as a parameter of the voluntary control (correction value setting part).

Accordingly, by obtaining correction values for correcting the relationship between reference myopotentials and detected byopotential signals (myopotential signals) in correspondence with joint angles that change in accordance with a predetermined movement, suitable correction values can be set for performing control in correspondence with various joint angles. Further, in a case where calibration is to be performed for the second time or more, the parameter K' can be corrected without using the load from the motor but by only performing a single motion of moving the finger from an extended state to a bent state. Accordingly, the physical workload of the wearer can be significantly reduced. In addition, the preparation time required for calibration after the movement assisting glove 20 is worn can be reduced. Therefore, in a case where calibration is performed for the second time or more, movement of joints can be promptly started. Further, because calibration can be performed during movement, calibration can be frequently performed when a joint is bent during a routine movement without being noticed by the wearer. Accordingly, a suitable control can be performed constantly.

Next, a control process corresponding to a calibration resetting mode 2 is described with reference to FIG. 22. In the resetting mode 2, the wearer moves the finger joints in an extending direction or a bending direction (e.g., bending a finger from an extended state to a bent state).

Figure 22:
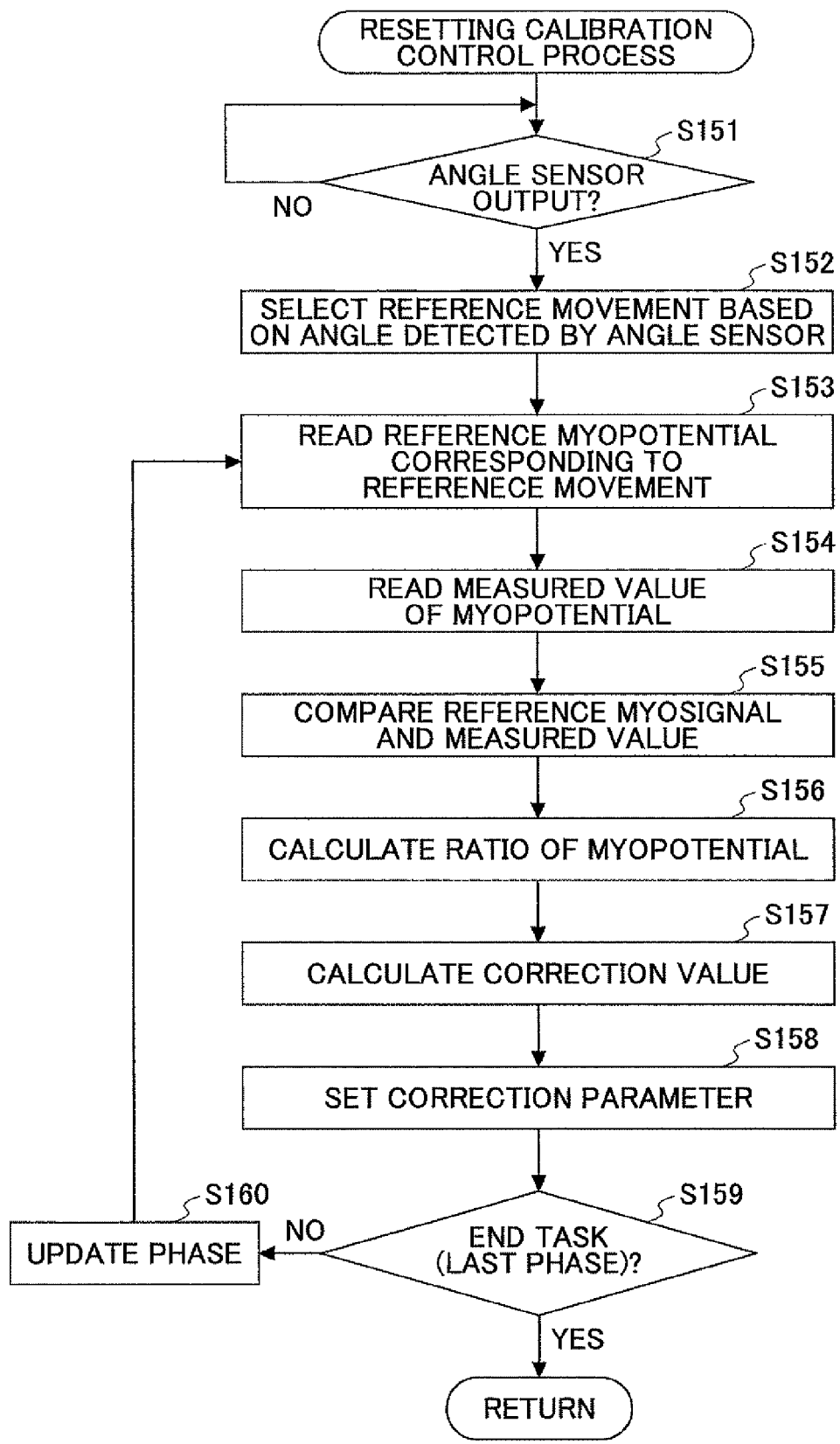
FIG. 22 is a flowchart illustrating processes performed in controlling resetting calibration based on resetting mode 2.

As illustrated in FIG. 22, the control part 100F determines whether a detection signal is output from the angle sensor 96. In a case where movement of the finger joint is detected by the detection signal output from the angle sensor 96, the process proceeds to step S152. In step S152, a basic movement of the wearer is set by selecting a task stored in the calibration database 400 based on the detection signal from the angle sensor 96.

Then, in step S153, reference myopotentials corresponding to the movement of the finger joints are read out from the memory 102. Then, in step S154, measured values of myopotentials of the wrist of the wearer are read out from the biopotential sensors 61-65. Then, in step S155, the reference myopotentials and the measured values of myopotentials are compared.

Then, in step S156, the ratio between the reference myopotentials and the measured values of myopotentials are calculated. Then, in step S157, the correction value (correction parameter) of the control signal to be supplied to the drive current generation part 220 is calculated by reading out parameters stored in correspondence with movement angles of finger joints in the calibration database 400 and multiplying the read out parameters with the ratio between the reference myopotentials and the measured values of myopotentials. Then, in step S158, the correction parameter is set as a parameter of the voluntary control (correction value setting part).

Then, in step S159, it is determined whether the tasks of the calibration process are finished (completed). In a case where there is an unfinished phase(s) of the calibration process, the process proceeds to step S160. In step S160, the next phase is updated and the processes in steps S153 and after are performed again.

In step S159, calibration for this time is terminated when the tasks of the calibration process are finished.

Accordingly, in a case where calibration is to be performed for the second time or more, the parameter K' can be corrected without using the load from the motor. Accordingly, the physical workload of the wearer can be significantly reduced. In addition, the preparation time required for calibration after the movement assisting glove 20 is worn can be reduced.

Accordingly, calibration of surface myopotential can be performed by combining movements of finger joints of the wearer. Further, calibration that matches each individual can be performed. Thus, even in a case where the wearer is a physically disable person, calibration can be performed based on a movement that can be performed by the wearer. Further, other movements (tasks) may be set as the reference movement.

In the sixth embodiment, although the calibration control processes are performed with the control circuit of the first embodiment, the calibration control processes may be performed with the control circuits of the second-fifth embodiments. Nevertheless, because the calibration control processes performed with the control circuits of the second-fifth embodiments are substantially the same as those illustrated in FIGS. 19-22, the calibration control processes performed with the control circuits of the second-fifth embodiments are not described.

Next, the wearable movement assisting apparatus 10 according to a modified example is described.

Modified Example 1

Figure 23:
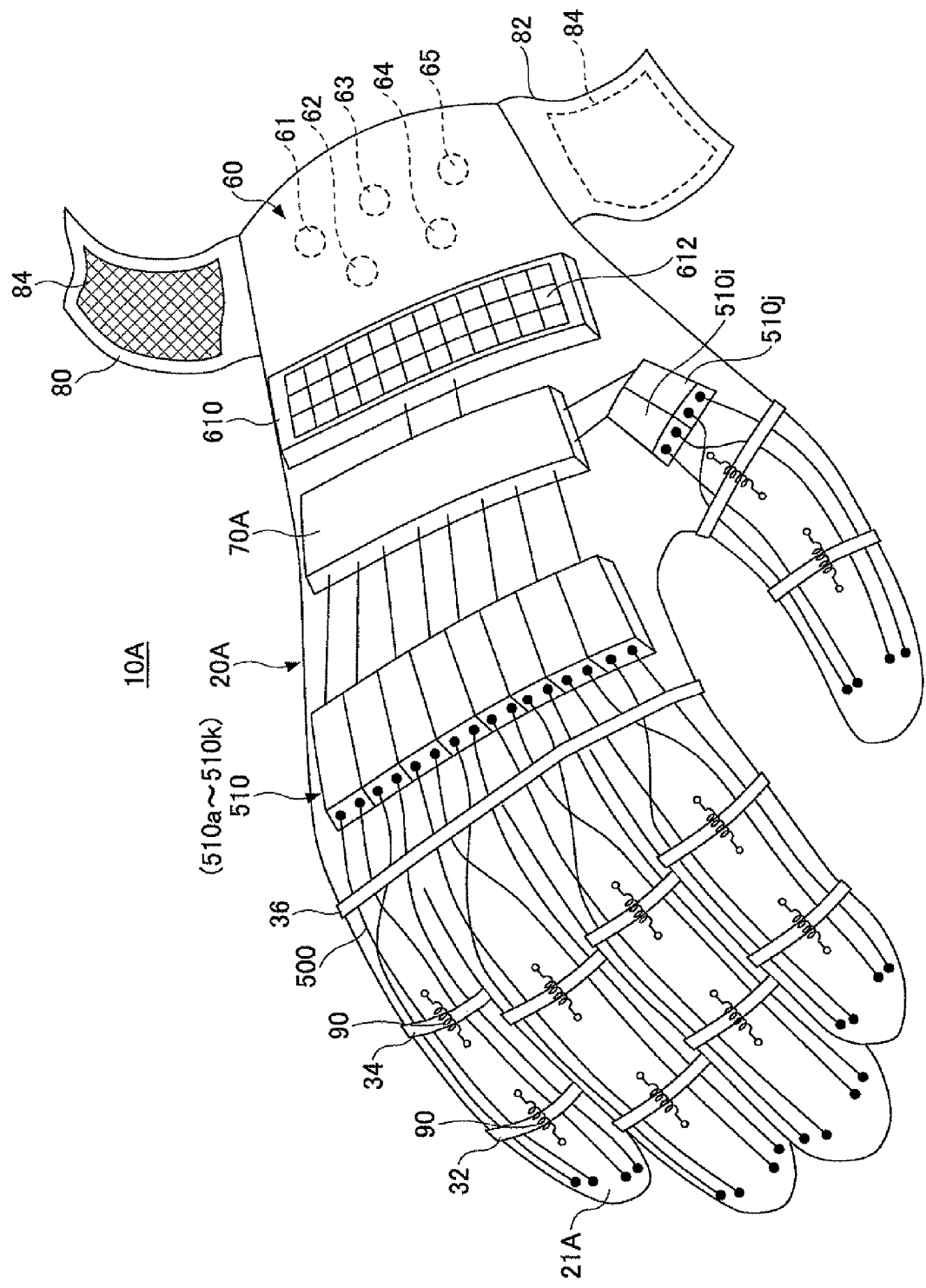
FIG. 23 is a schematic diagram illustrating a wearable type movement assisting apparatus 10 according to a first modified example.

FIG. 23 is a schematic diagram illustrating the wearable type movement assisting apparatus 10 according to a first modified example. In FIG. 23, like components/elements are denoted with like reference numerals as those illustrated in FIG. 1 and are not further described. As illustrated in FIG. 23, the wearable type movement assisting apparatus 10A of the first modified example includes a movement assisting glove 20A, plural linear members 500, a driving part 500, the biosignal detection part 60, a control unit 70A, and a rechargeable battery 610. The rechargeable battery 610 has a solar battery 612 provided on a surface thereof. The rechargeable battery 610 is constantly charged by having the solar battery 612 receive indoor illumination light or sunlight and generate electricity.

Similar to the movement assisting glove 20 of the first embodiment, the movement assisting glove 20A is formed in a three-dimensional shape. The movement assisting glove 20A is matched to the size of the hand of the wearer so that the hand can cohesively fit the movement assisting glove 20A.

Figure 24A:
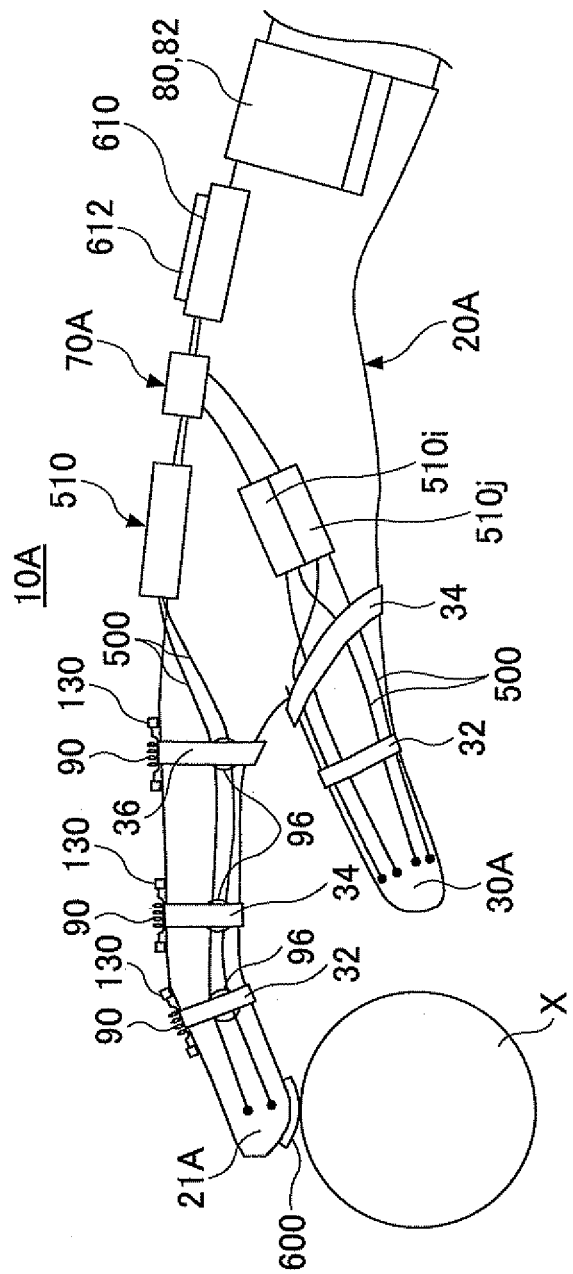
FIG. 24A is a side view of a wearable type movement assisting apparatus 10 according to the first modified example.

Further, the movement assisting glove 20A includes finger insertion parts 21A into which each finger of the wearer is inserted. As illustrated in FIG. 24A, an object detection sensor 600 for detecting an object X is provided on a lower side of the tip of the finger insertion part 21A.

The object detection sensor 600 includes, for example, a thin membrane switch having a resilient property. When the object detection sensor 600 contacts the object X, the object detection sensor 600 outputs a detection signal to the control unit 70A. In a case where the detection signal is input to the control unit 70A, the control unit 70A performs calculations for generating a driving force enabling each of the finger insertion parts 21A to perform a grabbing movement.

Further, in addition to the providing the object detection sensor 600 on the tip of each finger insertion part 21A of the movement assisting glove 20A, a push-type micro-switch is provided in, for example, a non-grabbing portion (which does not contact the object X) of a wrist or the side of the hand. For example, when the micro-switch is switched on by contacting a table or a chair, controls can be started for moving the linear members and causing the finger insertion parts to perform a grabbing movement.

The components of the object detection sensor 600 are not limited to the membrane switch and the micro-switch. For example, a reflection type optical sensor or a proximity sensor (e.g., an induction type proximity sensor, a capacitance type proximity sensor, a magnetic type proximity sensor) may be used for detecting the object X or a table (on which the object X is placed) without contact.

Plural linear members 500 are provided on both sides of each finger insertion part 21A and on the backhand side of the movement assisting glove 20A along a direction in which each finger insertion part 21A extends. Each of the plural linear members 500 has one end coupled to each finger insertion part 21A of the movement assisting glove 20A. In this modified example, four linear members 500 are provided to a single finger insertion part 21A for ensuring an auxiliary motive power from the movement of the linear members 500. The number of the linear member 500 can be increased or reduced in correspondence with the defect of hand of the wearer.

The finger insertion parts 21A and the movement assisting glove 20A are integrally formed as a united body. Each finger insertion part 21A is formed in a cap-like shape for covering an entire finger. Further, the plural linear members 500 are fastened to an outer side of each finger insertion part 21A by fastening rings 32, 34, 36 that wrap around finger joints of the wearer. Accordingly, the driving part 510 can efficiently transmit a driving force to each finger insertion part 21A of the movement assisting glove 20A via each linear member 500.

Further, the plural linear members 500 are sewn to an outer side of the movement assisting glove 20A. Therefore, the plural linear members 500 are able to move in the expanding direction or the contracting direction. Further, each finger insertion part 21A of the movement assisting glove 20A can move in correspondence with the expansion or the contraction direction as a united body with the linear member 500. The linear member 500 of the first modified example includes a hollow-shaped tube (cylinder body) formed of resin. The cylinder body includes a hollow path extending in a longitudinal direction thereof. A fluid is to be filled inside the hollow path. Although the plural linear members 500 are formed with a material that transmits a driving force, the material of the plural linear members 500 is formed significantly lighter compared to, for example, a metal material. Thereby, the workload of the wearer can be reduced.

Figure 24B:
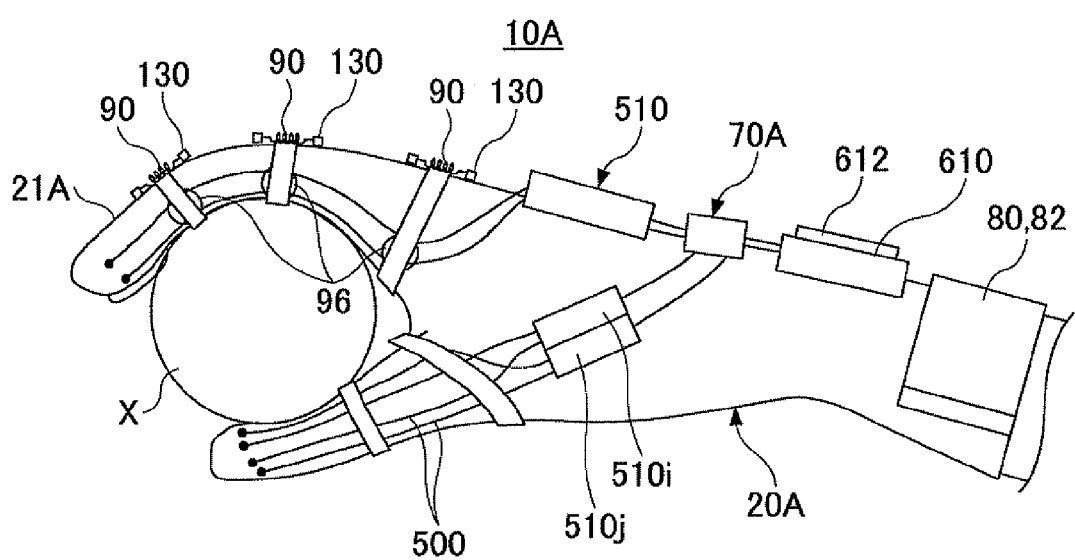
FIG. 24B is a schematic diagram illustrating a movement state where an object is grabbed by using a wearable type movement assisting apparatus 10 according to the first modified example.

As illustrated in FIGS. 24A and 24B, the urging member 90 is provided at an outer side of a finger joint portion of each finger insertion part 21A. Accordingly, the urging member 90 applies an urging force (urging the finger insertion portion 21A to extend) to the surface covering the finger joint portion of the finger insertion portion 21A. The urging force serves as an assisting force that assists the extending movement (movement from a grabbing state of FIG. 24B to a releasing state of FIG. 24A) of the corresponding finger joint.

Figure 25A:
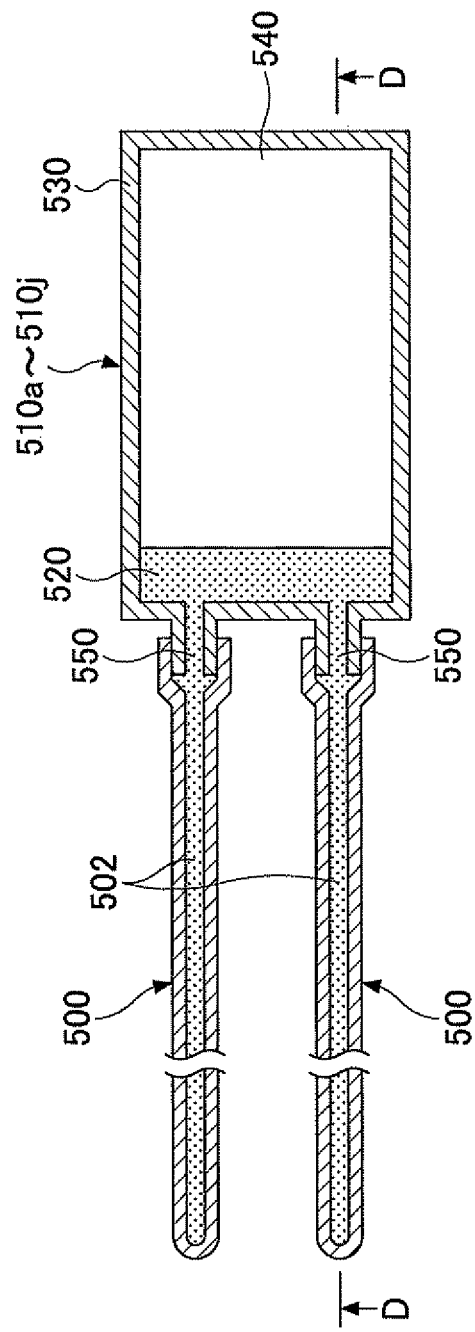
FIG. 25A is a cross-sectional view illustrating an inner structure of an actuator 510.
Figure 25B:
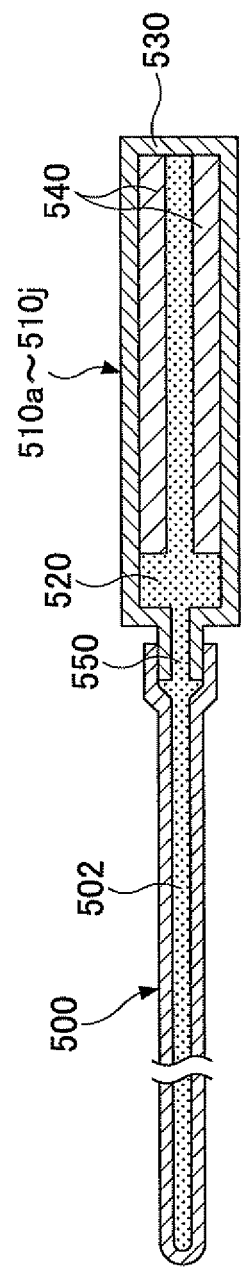
FIG. 25B is a vertical sectional view taken along line D-D of FIG. 25A.

As illustrated in FIGS. 25A and 25B, the driving part 510 includes actuators 510a-510j for compressing or decompressing a fluid 520 (illustrated with matte pattern) filled inside the hollow path 502 of the linear member 500. The actuators 510a-510j has a pair of Peltier devices 540 installed inside a flat-shaped housing 530. The Peltier device 540 is a temperature adjustment part that adjusts the temperature of the fluid 520 by heating (generating heat) or cooling (absorbing heat) in the electric current flowing direction.

Further, the fluid 520 may be a gel having a property in which the volume of the fluid 520 becomes smaller at a high temperature and the volume of the fluid 520 becomes smaller at a low temperature. For example, the gel may be formed of a polymer referred to as "poly benzyl methacrylate" (having a property of increasing its volume 10 times when a liquid enters a three-dimensional mesh configuration of the polymer) and an ion liquid of imidazolium type.

The fluid 520, which is provided in a space of the pair of Peltier devices 540, is heated or cooled simultaneously from upper and lower directions. Therefore, the fluid 520 can fill the inside of the housing 530 so that volume of the fluid 520 can be increased of reduced in a short time. When the fluid 520 filled inside the flat-shaped space is heated or cooled by the pair of Peltier devices 540, the actuator 510a-510j applies pressure (decompresses or compresses) with respect to the fluid 520 inside the hollow path 540 of the linear member 500 connected to an exit 550.

The inner diameter of the hollow path 502 is significantly small compared to the space inside the housing 530. Therefore, the amount in which the volume of the fluid 520 changes in correspondence with the heating or cooling of the inside of the housing 530 is amplified with respect to the fluid 520 in the hollow path 502. Thereby, the fluid 520 can be compressed or decompressed. Further, the linear member 500 is a resin-made narrow tube having the hollow path 502 provided therein. As illustrated in FIG. 3A, a bellows part is provided at inner and outer sides of the resin-made narrow tube. The bellows part 56 includes fine-sized concave parts and convex parts. Accordingly, each linear member 500 can expand and contract in a longitudinal direction in correspondence with the increase/decrease of pressure applied to the fluid 520 filled in the hollow path 502.

Each linear member 500 is fastened to an outer side of the movement assisting glove 20A by fastening rings 32, 34, 36. In a case where the backhand side of the movement assisting glove 20A contracts in the longitudinal direction by being decompress whereas the palm side of the movement assisting glove 20A expands in the longitudinal direction by being compressed, the linear member 500 applies a driving force to the finger insertion part 21A such that the finger insertion part 21A is extended. In a case where the backhand side of the movement assisting glove 20A expands in the longitudinal direction by being compressed whereas the palm side of the movement assisting glove 20A contracts in the longitudinal direction by being decompressed, the linear member 500 applies a driving force to the finger insertion part 21A such that the finger insertion part 21A is bent.

A heat-resistant resin material is used as the linear member 500 for maintaining a state where the fluid 520 (which changes from a low temperature to a high temperature) is filled and sealed inside the hollow path 502. Further, the electric power from the charged rechargeable battery 610 is supplied to each Peltier device 540 of the actuators 510a-510j. The solar battery 612 of the rechargeable battery 610 is constantly charged for handling the power consumption by the Peltier devices 540.

In the first modified example, two linear members 500 are provided on one side of each finger insertion part 21A. In addition, the actuators 510a-510j are provided in parallel with respect to each finger insertion part 21A. In other words, four linear members 500 are provided 500 two on each side of the finger insertion part 21A, so that the linear members 500 on the palm side and the linear members 500 on the backhand side are connected to different driving parts. Accordingly, the linear members 500 can, for example, drive the corresponding finger insertion part 21A to an extended state by compressing the linear members 500 on the palm side and decompressing the linear members 500 on the backhand side. On the other hand, the linear members 500 can, for example, drive the corresponding finger insertion part 21A to a grabbing state by decompressing the linear members 500 on the palm side and compressing the linear members 500 on the backhand side.

The control unit 70A performs calculation based on biosignals detected from the biopotential sensors 61-65 of the biosignal detection part 60 and outputs drive control signals to the actuator 510a-510j. Because the control processes that can be performed by the control unit 70A are substantially the same as the control processes performed by the above-described control parts 100, 100A-100F of the first-sixth embodiments, the control processes performed by the control part 70A are not described.

Similar to the first embodiment, the movement assisting glove 20A of the first modified example can transmit a driving force of the driving part 50 to cause the finger joints of the wearer to move by expanding or contracting the linear members 500 in the movement direction of the joints of the finger insertion parts 21A in accordance with drive control signals from the control unit 70A. Thereby, weight of the wearable type movement assisting apparatus 10A and the load of the wearer can be reduced.

Further, the temperature adjustment part for adjusting the temperature of the fluid 520 is not limited to the Peltier devices. For example, the fluid 520 may alternatively be heated by placing a heating wire inside the hollow path 502 and energizing the heating wire. This configuration allows the fluid 520 inside the hollow path 502 to be heated entirely. Therefore, temperature can be swiftly changed and responsiveness with respect to the driving part 510 can be improved. The fluid 520 can be swiftly be cooled by releasing heat from the surface of the hollow path 502 owing to the linear shape of the hollow path 502.

Further, a gel having fiber conductors mixed therein can be used as the fluid 520. With this type of gel, the fiber conductors are moved and aligned inside the gel by Coulomb force when voltage is applied to the gel, to thereby form a conducting path. The conducting path generates heat by having electric current flowing in the conducting path. Accordingly, the volume of the gel itself changes along with the change of temperature inside the gel. In the case where the gel mixed with fiber conductors is used, electrodes for applying voltage are provided in a position of the Peltier devices 540 instead of the pair of Peltier devices 540. Accordingly, the driving part 510 can apply a driving force by applying an electric field to the gel interposed between the electrodes.

Modified Example 2

Figure 26:
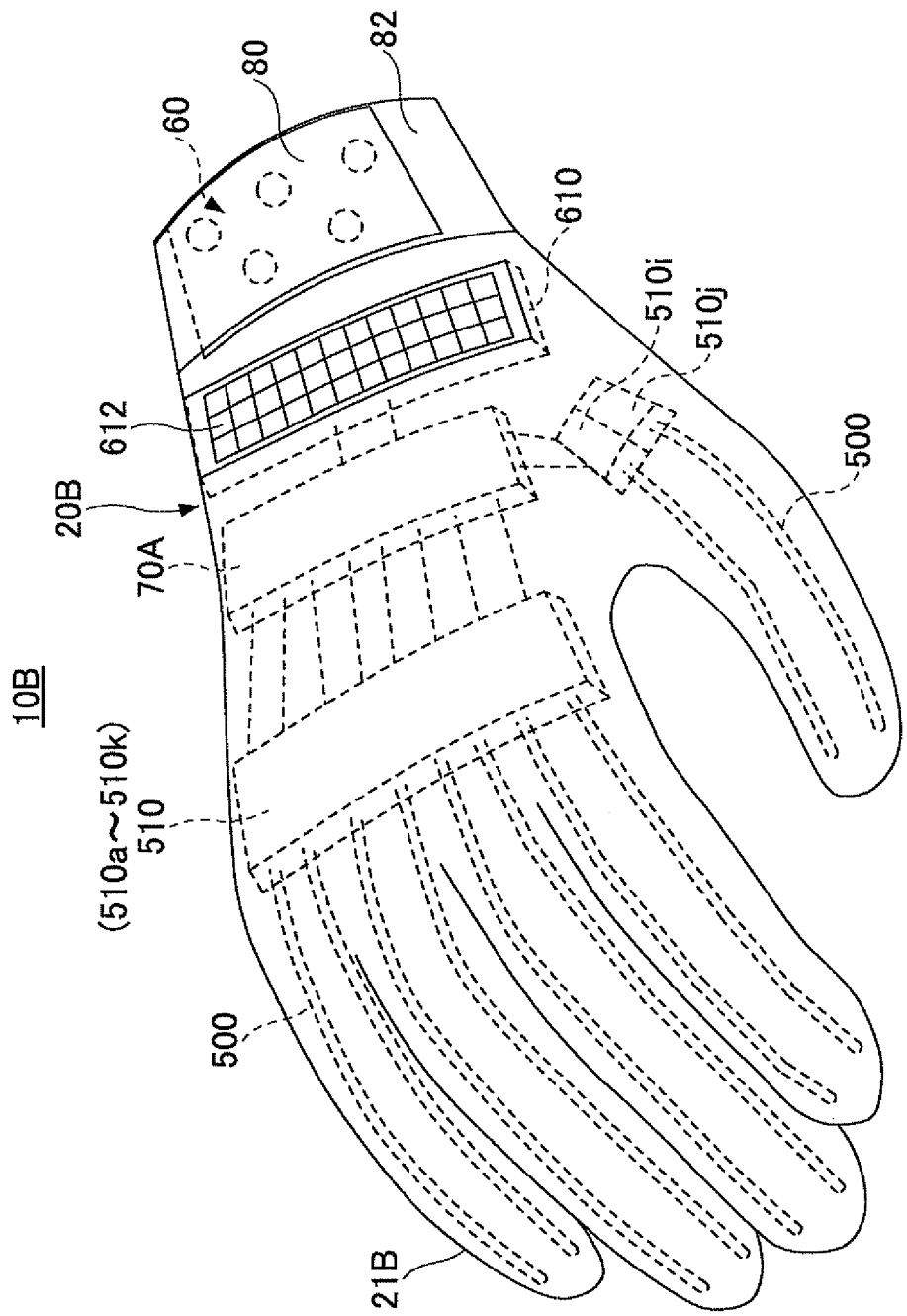
FIG. 26 is a schematic diagram illustrating a wearable type movement assisting apparatus 10B according to a second modified example.

FIG. 26 is a schematic diagram illustrating a wearable type movement assisting apparatus 10B according to a second modified example. In FIG. 26, like components/elements are denoted with like reference numerals as those illustrated in FIG. 23 and are not further described. As illustrated in FIG. 26, the wearable type movement assisting apparatus 10B has a movement assisting glove 20B, the plural linear members 500 of the first modified example, the driving part 510, the biosignal detection part 60, and the control unit 70A installed in-between the outer movement assisting glove and the inner movement assisting glove. Thereby, the driving part 510 can efficiently transmit driving force to each finger insertion part 21B of the movement assisting glove 20B via the linear members 500.

Because the rechargeable battery 610 has the solar battery 612 provided on the surface thereof, the solar battery 612 is exposed on the outer side of the movement assisting glove 20B.

Figure 27A:
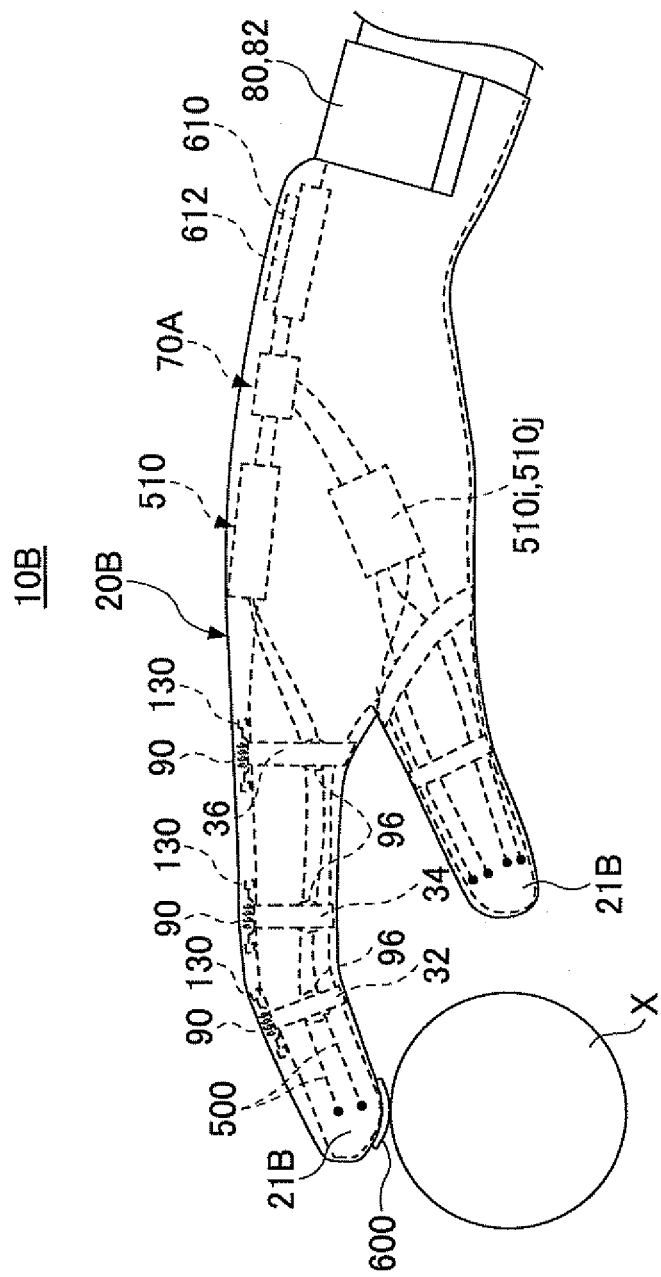
FIG. 27A is a side view of a wearable type movement assisting apparatus 10B according to the second modified example.
Figure 27B:
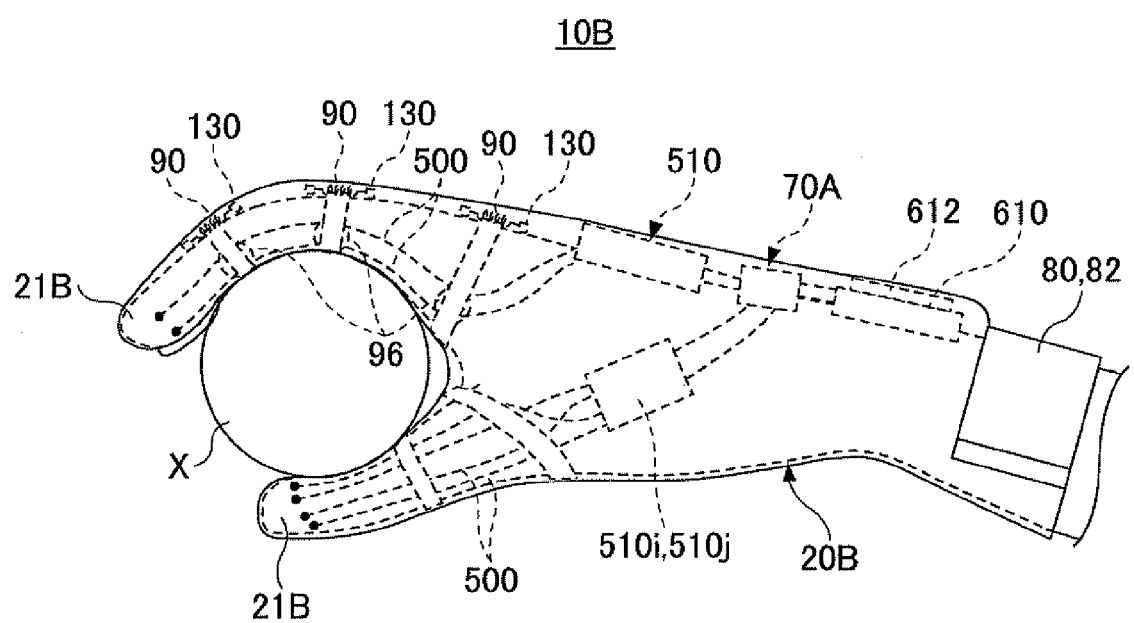
FIG. 27B is a schematic diagram illustrating a movement state where an object is grabbed by using a wearable type movement assisting apparatus 10B according to the second modified example.

As illustrated in FIGS. 27A and 27B, the movement assisting glove 20B can be designed as an ordinary glove because the plural linear members 500, the driving part 510, the biosignal detection part 60, and the control unit 70A cannot be seen from the outside. Accordingly, the wearer can go outdoors wearing the movement assisting glove 20B and move his/her finger joints without having to worry about drawing attention from others.

Further, with the movement assisting glove 20B, the plural linear members 500, the driving part 510, the biosignal detection part 60, and the control unit 70A may be provided in the inner side of the outer movement assisting glove. Further, among the plural linear members 500, the driving part 510, the biosignal detection part 60, and the control unit 70A, at least the parts that contact the inserted fingers may be partially sewn together with a cover material made of cloth, leather, or synthetic leather.

Similar to the first embodiment, the movement assisting glove 20B of the second modified example can transmit a driving force of the driving part 510 to cause the finger joints of the wearer to move by expanding or contracting the linear members 500 in the movement direction of the joints of the finger insertion parts 21B in accordance with drive control signals from the control unit 70A. Thereby, weight of the wearable type movement assisting apparatus 10B and the load of the wearer can be reduced.

Modified Example 3

Figure 28:
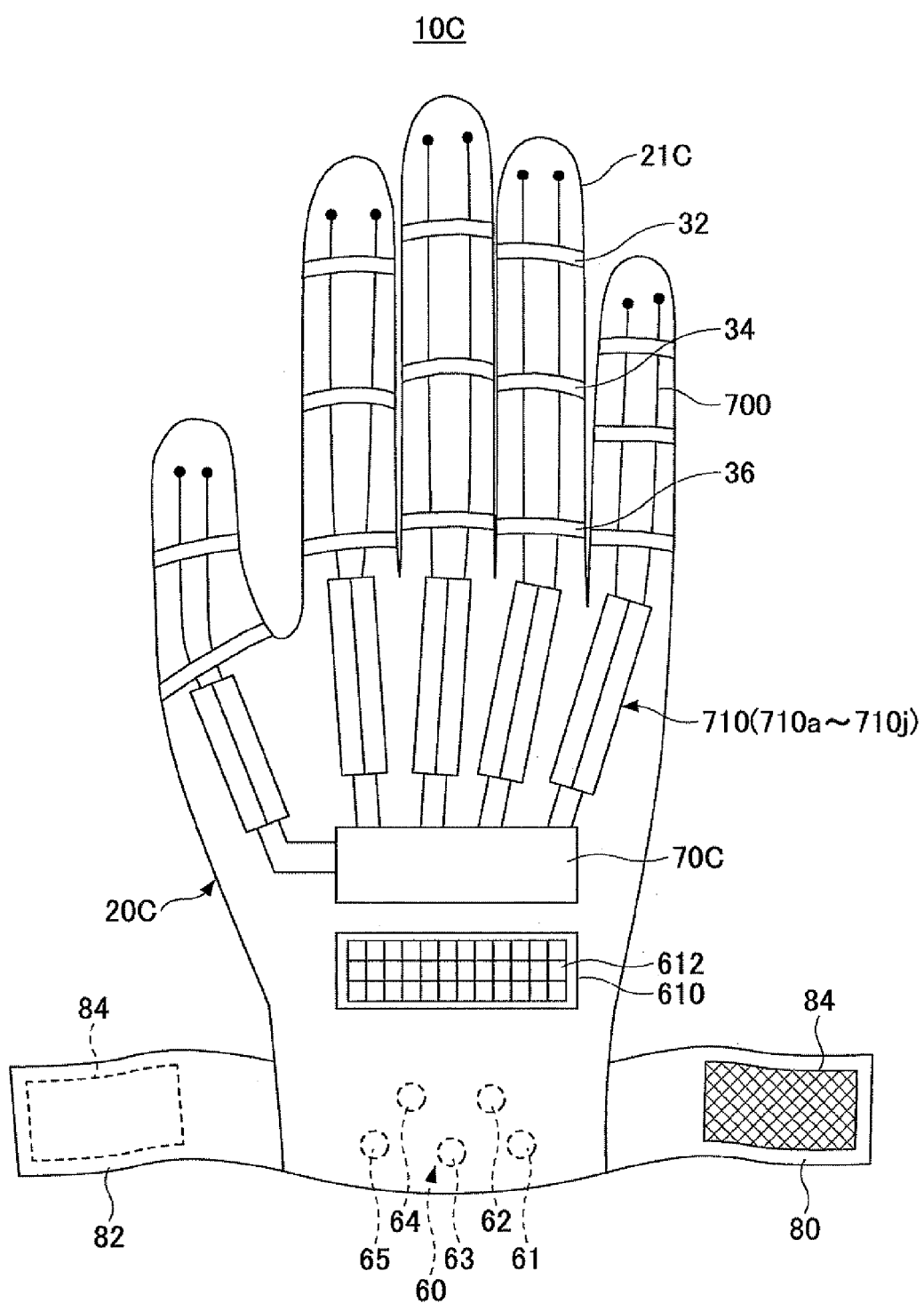
FIG. 28 is a schematic diagram illustrating a wearable type movement assisting apparatus 100 according to a third modified example.

FIG. 28 is a schematic diagram illustrating a wearable type movement assisting apparatus 10C according to a third modified example. In FIG. 28, like components/elements are denoted with like reference numerals as those illustrated in FIG. 23 and are not further described. As illustrated in FIG. 28, the wearable type movement assisting apparatus 10C includes a movement assisting glove 20C, plural linear members 700, the driving part 710, the biosignal detection part 60, a control unit 70C, and the rechargeable battery 610.

The plural linear members 700 are formed of, for example, wires (e.g., piano wires). The driving part 710 includes linear motors 710a-710j. Although the plural linear members 700 are formed with a material that transmits a driving force, the material of the plural linear members 700 is formed significantly lighter compared to, for example, a rod-like metal material. Thereby, the workload of the wearer can be reduced.

One end of the linear member 700 is coupled to a needle (magnet) of the linear motor 710a-710j whereas the other end of the linear member 700 is coupled to a corresponding finger insertion part 21C of the movement assisting glove 20C. It is to be noted that the movement assisting glove 20C includes a linear scale that measures the amount of movement of the needle of the linear motor 710a-710j. The linear scale may be attached, for example, in a position enabling the amount of movement of the needle of the linear motor 710a-710j to be measured or in position along the linear member 700 coupled to the needle of the linear motor 710a-710j.

Further, the plural linear members 700 are sewn to the outer side of the movement assisting glove 20C. Therefore, the plural linear members 700 can move in the expanding direction or the contracting direction. Further, each finger insertion part 21C of the movement assisting glove 20C can move in correspondence with the expansion or or the contraction as a united body with the linear member 700. Accordingly, the driving part 710 can efficiently transmit driving force of the linear motors 710a-710j to each finger insertion part 21C of the movement assisting glove 20C via the linear members 700.

Figure 29A:
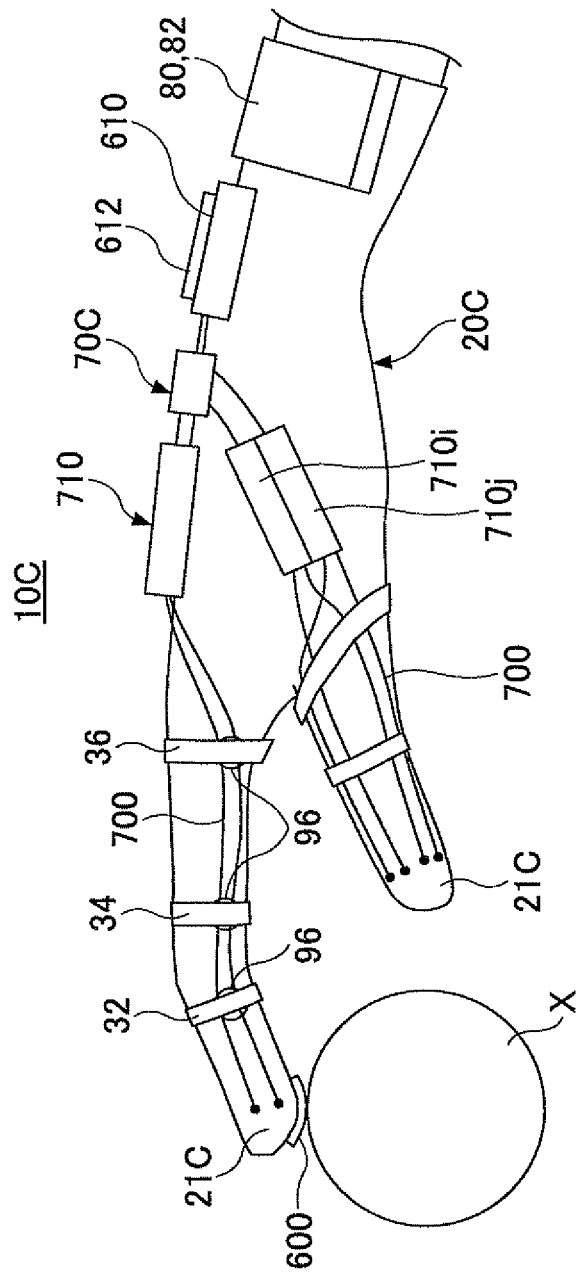
FIG. 29A is a side view of a wearable type movement assisting apparatus 10C according to the third modified example.
Figure 29B:
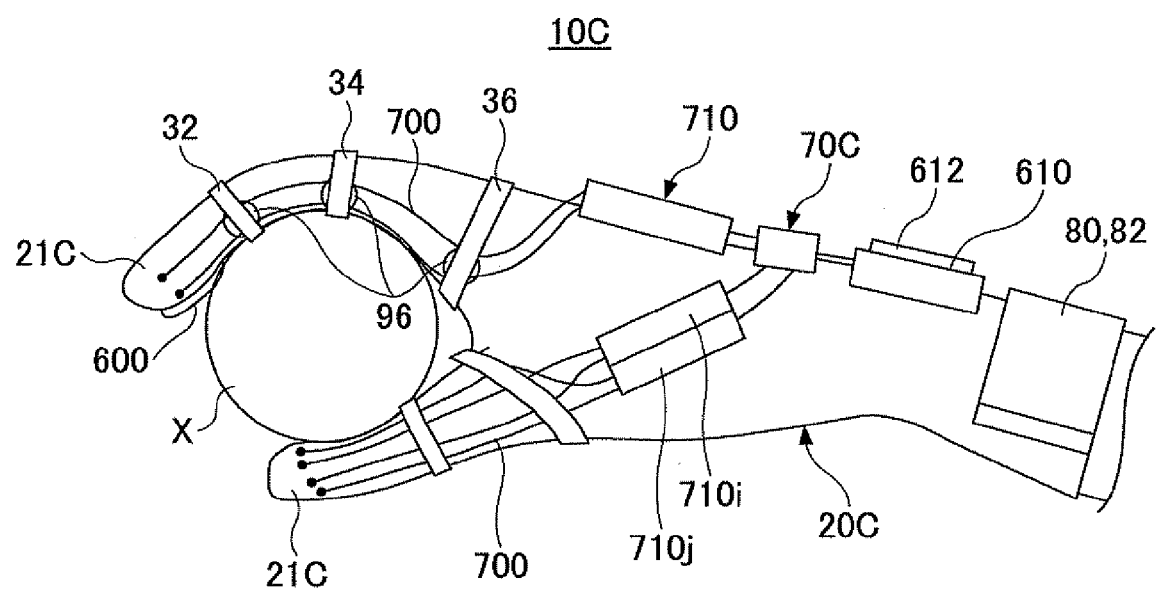
FIG. 29B is a schematic diagram illustrating a movement state where an object is grabbed by using a wearable type movement assisting apparatus 10C according to the third modified example.

The linear motors 710a-710j are magnetized by energizing plural coils (stators) and also generate a thrust force to the needles of the linear motors 710a-710j in accordance with control signals from the control unit 70C. As illustrated in FIGS. 29A and 29B, plural linear members provided along the finger insertion parts 21C of the movement assisting glove 20C are directly driven in the expanding direction or the contracting direction by the thrust force of the linear motors 710a-710j.

Similar to the above-described embodiments, the control unit 70C of the third modified example outputs drive control signals to the linear motor 710a-710j by performing calculation based on biosignals detected from the biopotential sensors 61-65 of the biosignal detection part 60. Because the control processes that can be performed by the control unit 70C are substantially the same as the control processes performed by the above-described control parts 100, 100A-100F of the first-sixth embodiments, the control processes performed by the control part 70C are not described.

Similar to the first embodiment, the movement assisting glove 20C of the third modified example can transmit a driving force of the driving part 510 to cause the finger joints of the wearer to move by expanding or contracting the linear members 700 in the movement direction of the joints of the finger insertion parts 21C in accordance with drive control signals from the control unit 70C. Thereby, weight of the wearable type movement assisting apparatus 100 and the load of the wearer can be reduced.

Modified Example 4

Figure 30:
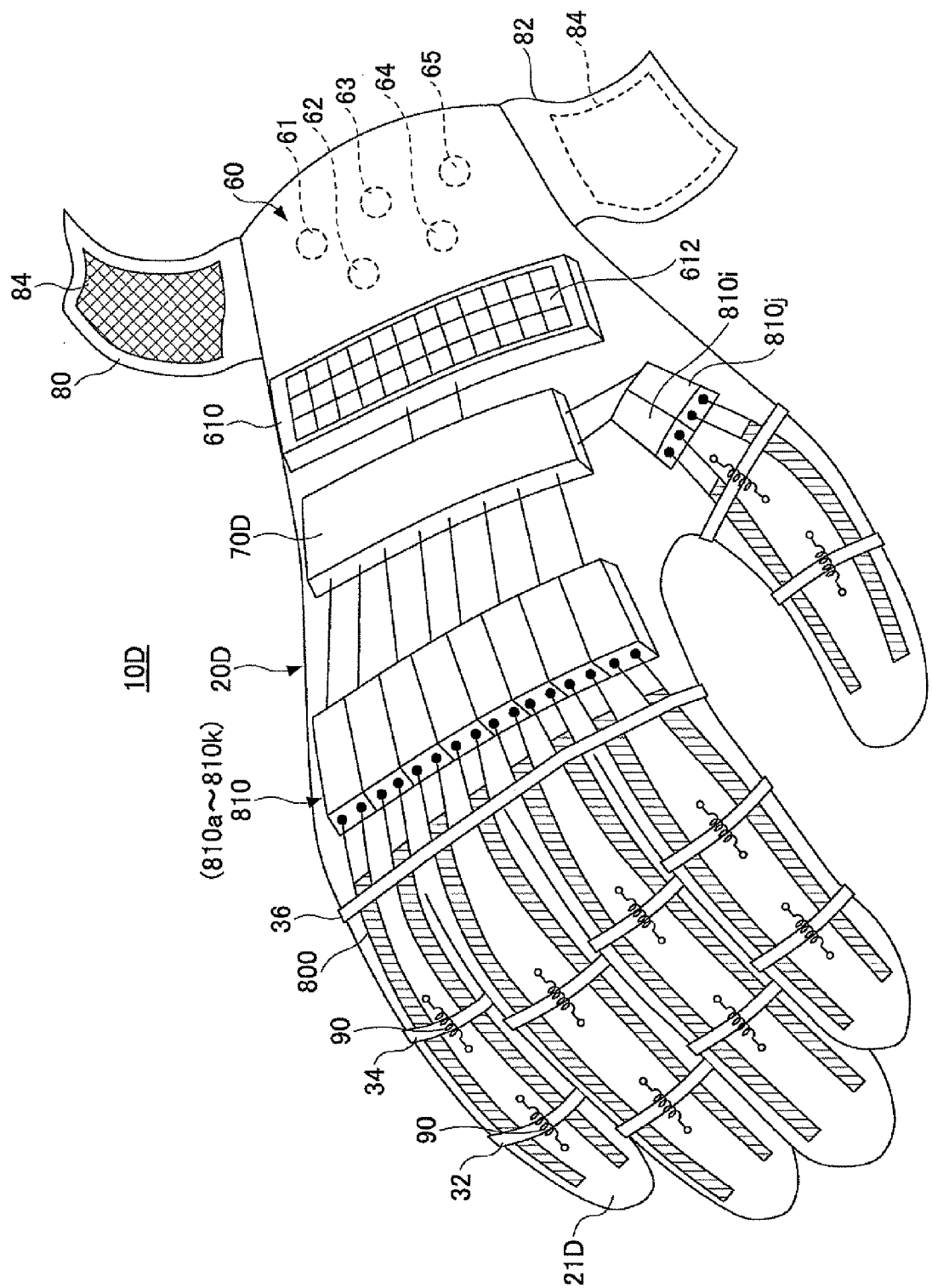
FIG. 30 is a schematic diagram illustrating a wearable type movement assisting apparatus 10D according to a fourth modified example.

FIG. 30 is a schematic diagram illustrating a wearable type movement assisting apparatus 10D according to a fourth modified example. As illustrated in FIG. 30, the wearable type movement assisting apparatus 10D includes a movement assisting glove 20D, plural linear members 800, an applied voltage switching circuit 810, the biosignal detection part 60, a control unit 70D, and the rechargeable battery 610.

Each linear member 800 is fastened to a corresponding finger insertion part 21D by fastening rings 32, 34, 36. Accordingly, driving force generated from the linear members can be directly transmitted to the finger insertion parts 21D, so that the finger insertion parts 21D are driven to a straight state (a state where each finger is extended) or a bent state (a state where each finger is bent).

The plural linear members 800 are formed from a synthetic resin substrate having a resilient property for generating a driving force by volume change in correspondence with the amount of applied voltage or polarity of the applied voltage. That is, each linear member 800 generates a driving force that causes a corresponding finger insertion part 21D to move from the straight state to the bent state or move from the bent state to the straight state in correspondence with voltage applied to an electrode layer thereof from the applied voltage switching circuit 810.

Because the linear member 800 itself serves as a driving part that generates a driving force, no actuator (e.g., motor) is needed. Accordingly, compared to having a separate actuator, weight of the wearable type movement assisting apparatus 10C can be significantly reduced. Thus, the load of the wearer can be reduced.

Although the fourth modified example in FIG. 4 has 2 linear members 800 provided on a back side (backhand side) of the corresponding finger insertion part 21D, 3 or more linear members 800 may be provided.

Figure 31A:
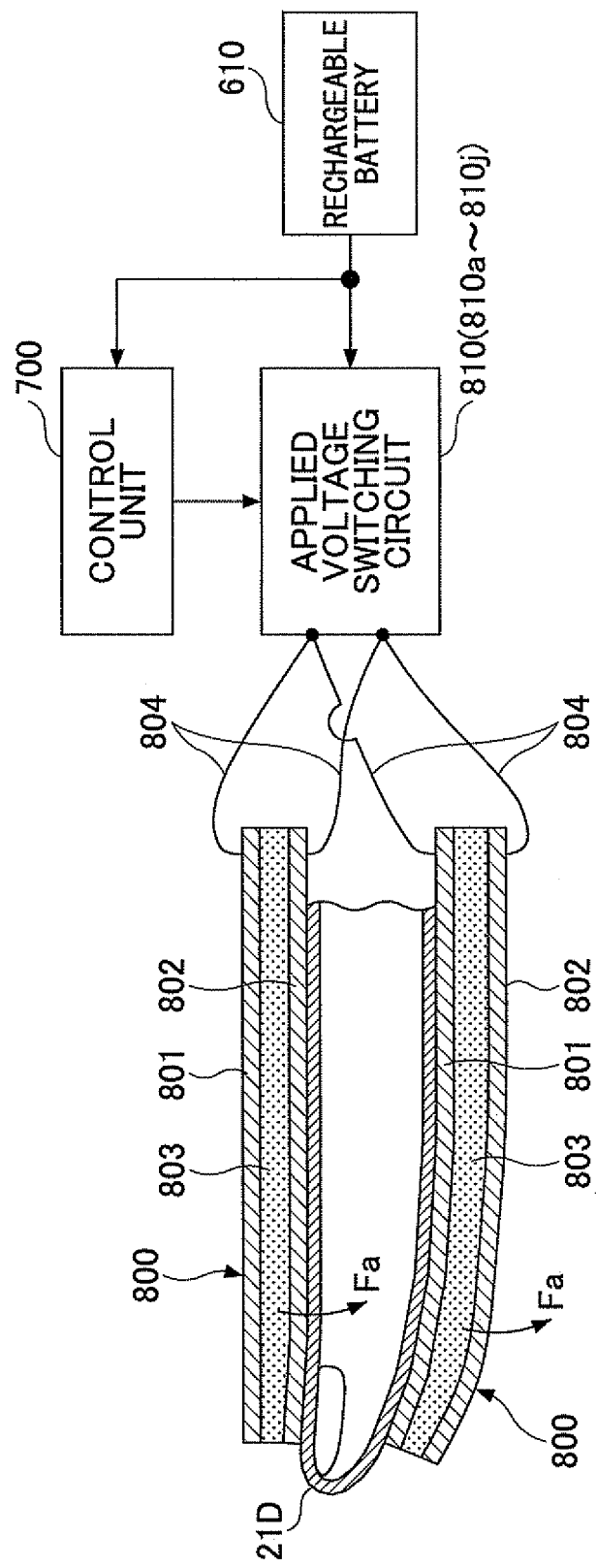
FIG. 31A is a schematic diagram illustrating a part of a cross section of a part of an finger insertion part of a wearable type movement assisting apparatus 10D according to the fourth modified example.
Figure 31B:
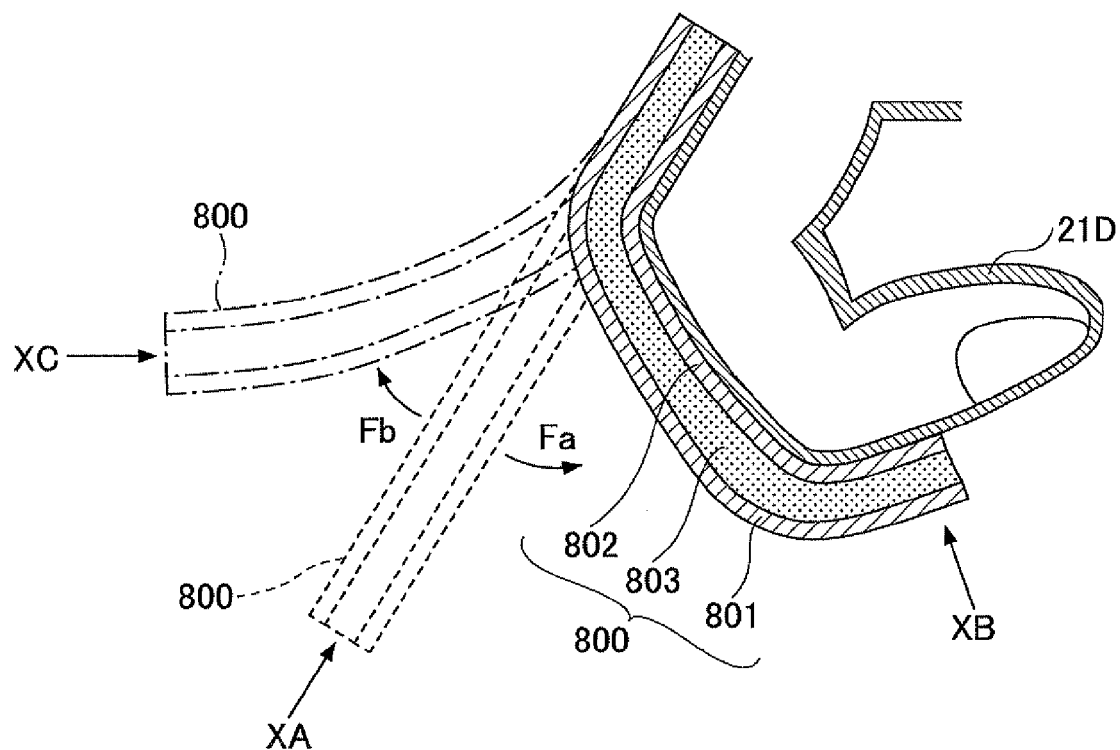
FIG. 31B is a schematic diagram illustrating a bent state of a finger insertion part of a wearable type movement assisting apparatus 10D according to the fourth modified example.

FIG. 31A is a schematic diagram illustrating a part of a cross section of the finger insertion part 210 of the wearable type movement assisting apparatus 10D according to the fourth modified example. FIG. 31B is a schematic diagram illustrating a bent state of the finger insertion part 21D of the wearable type movement assisting apparatus 100 according to the fourth modified example.

As illustrated in FIG. 31A, the linear members 800 are attached to the front side (palm side) and the back side (backhand side) of corresponding finger insertion parts 210 of the movement assisting glove 20D in a manner extending along the extending direction of finger insertion part 21D.

Electrode layers 801, 802 of the linear members 800 are connected to corresponding output terminals of the applied voltage switching circuit 810 (810a-810j) via respective voltage control wires 804. The rechargeable battery 610 is connected to the applied voltage switching circuit 810 (810a-810j) for serving as a voltage supply source. The applied voltage switching circuit 810 (810a-810j) controls the polarity and size of the voltage applied to the electrode layers 801, 802 of the linear members 800 in accordance with control signals from the control unit 70D.

The linear member 800 has a pair of the electrode layers 801, 802 that are arranged in parallel and layered in a manner having a driving layer 803 interposed therebetween. The driving layer 803 is formed of, for example, an ion exchange resin that switches the direction of generating a driving force in accordance with the polarity (positive/negative) of the applied voltage. An ion conduction actuator having the electrode layers 801, 802 provided on upper and lower surfaces of the ion exchange resin is in a stationary state (undriven state) extending in a straight line when no voltage is applied. In addition, positive ions on the positive side (anode side) migrate to the negative side (cathode side) in the polymer electrolyte inside the ion exchange resin by switching the polarity of the pair of electrode layers 801, 802. Thereby, the ion exchange resin deforms in a manner warping toward the negative side (cathode side) in correspondence with the swelling that differs depending on the polarity of the ion exchange resin. The driving layer 803 generates a driving force that causes the finger insertion part 21D to move in accordance with the difference of swelling on the front and back sides of the driving layer 803.

Accordingly, by switching the polarity of the pair of electrodes 801, 802 with the applied voltage switching circuit 810, the deformation direction of the driving layer 803 can be switched. Thereby, the amount of change can be controlled in accordance with the size of the applied voltage.

Next, an operation of generating a driving force of the linear member 800 is described.

For example, by switching the polarity of the applied voltage with the applied voltage switching circuit 810 so that the electrode layer 801 on the upper side is negative (cathode) and the electrode layer 802 on the lower side is positive (anode), the swelling of the upper side of the driving layer 803 becomes larger than the swelling of the lower side of the driving layer 803. Therefore, a driving force Fa attempting to bend the finger insertion part 21D in a downward direction is generated.

As illustrated in FIG. 31B, the finger insertion part 21D is driven in a bending direction from a straight state XA (illustrated with broken lines) to a bent state XB (state where finger joints are bent). Further, by switching off (zero) the voltage supplied to the electrode layers 801, 802 of the linear member 800, the finger insertion part 210 is driven in an extending direction such that the finger insertion part 21D recovers from the bent state XB (illustrated with solid lines) to the straight state XA at a slow speed.

Further, by switching the polarity of the applied voltage with the applied voltage switching circuit 810 so that the electrode layer 801 on the upper side is positive (anode) and the electrode layer 802 on the lower side is negative (cathode), a driving force Fb attempting to bend the finger insertion part 210 in an upward direction is generated. Accordingly, by switching the polarity of the voltage applied to the electrode layers 801, 802 of the linear member 800, the finger insertion part 21D can swiftly recover from the bent state XB (illustrated with solid lines) to the straight state XA. The speed of this recovering movement is effective for rehabilitation training. Further, a large torque can be applied to the fingers from the bent state toward the extending direction.

Similar to the first embodiment, the movement assisting glove 20D of the fourth modified example can generate a force Fa, Fb that drives the finger insertion part toward the extending direction or the bending direction by switching the polarity of the voltage applied to the electrode layers 801, 802 of the linear members 800. Thereby, weight of the wearable type movement assisting apparatus 10D and the load of the wearer can be reduced.

The driving layer 803 is not limited to an ion exchange resin. For example, a polymer material (e.g., a piezoelectric polymer, a conductive polymer, an electrostrictive polymer) that causes deformation or displacement due to volume expansion by being applied with voltage may also be used for the driving layer 803.

INDUSTRIAL APPLICABILITY

Although the above-described embodiments of the present invention describe a case of assisting the movement of the finger joints of a wearer by having the movement assisting glove 20 worn by the wearer, the above-described embodiments can also applied to rehabilitation training (function recovery training) of the movement of the finger joints by using the movement assisting glove 20. Therefore, the movement assisting glove 20 can also be used as a glove for rehabilitation.

Similar to the movement assisting glove 20 of the first embodiment, the above-described first-fourth modified examples may also expose the fingertips of the wearer by cutting the fingertip parts of the movement assisting gloves 20A-20D.

Further, the present invention is not limited to these embodiments, but variations and modifications may be made without departing from the scope of the present invention.

The present application is based on Japanese Priority Application No. 2009-094695 filed on Apr. 9, 2009 with the Japanese Patent Office, the entire contents of which are hereby incorporated by reference.

The invention claimed is:

1. A wearable type movement assisting apparatus comprising:
   a movement assisting glove including a finger insertion part, wherein the finger insertion part is configured such that a finger of a wearer is inserted therein;
   a driving part arranged on a backhand side of the movement assisting glove and configured to drive the finger insertion part with a driving force;
   at least one linear member arranged along the finger insertion part and configured to transmit the driving force of the driving part to the finger insertion part;
   a biosignal detection part configured to cohesively attach to a skin of the wearer and configured to detect a biosignal that causes the finger of the wearer to move; and
   a control part configured to output a drive control signal to the driving part based on a detection signal output from the biosignal detection part;
   wherein the driving part is configured to move the linear member in an extending direction or a bending direction of the finger insertion part based on the drive control signal from the control part,
   wherein the linear member includes a cylinder body having a resilient property and a wire inserted through a hollow part of the cylinder body,
   wherein the cylinder body includes a bellows part having concave parts and convex parts alternately arranged in series to expand and contract in correspondence with the extending and bending movement of finger joints,
   wherein one end of the wire is coupled to the driving part arranged on the backhand side of the movement assisting glove, and
   wherein another end of the wire is coupled to the finger insertion part.

2. The wearable type movement assisting apparatus as claimed in claim 1, wherein the linear member is fixed along a side part or a backhand side of the finger insertion part and configured to transmit the driving force to the finger insertion part.

3. The wearable type movement assisting apparatus as claimed in claim 1, wherein multiple linear members are arranged along the finger insertion part, wherein the driving force is transmitted in a movement direction of a joint of the finger by expansion or contraction of the multiple linear members.

4. The wearable type movement assisting apparatus as claimed in claim 1, wherein the linear member is provided on an outer side of the movement assisting glove.

5. The wearable type movement assisting apparatus as claimed in claim 1, wherein the linear member is provided in an inner side of the movement assisting glove, wherein an inner cover member is provided in a finger contacting part at the inner side of the movement assisting glove.

6. The wearable type movement assisting apparatus as claimed in claim 1, wherein the movement assisting glove includes an outer side assisting glove and an inner side assisting glove, wherein the linear member is provided between the outer side assisting glove and the inner side assisting glove.

7. The wearable type movement assisting apparatus as claimed in claim 1, further comprising an urging member that urges the finger insertion part in a manner causing a finger joint of the wearer to return from a bent state to a straight state or causing the finger joint of the wearer to return from the straight state to the bent state.

8. The wearable type movement assisting apparatus as claimed in claim 1, wherein the movement assisting glove includes a detection part,
   wherein the detection part is for detecting a gripping object and is located in the finger insertion part.

9. The wearable type movement assisting apparatus as claimed in claim 1, wherein the movement assisting glove has an opening in the finger insertion part that exposes a part of a fingertip of the wearer.

10. The wearable type movement assisting apparatus as claimed in claim 1, wherein the movement assisting glove has a finger angle detection sensor in the finger insertion part that detects a bending angle of a finger joint of the wearer.

11. The wearable type movement assisting apparatus as claimed in claim 1, wherein the control part includes
    a biosignal process part that obtains a signal for causing the finger of the wearer to move based on the biosignal detected from the biosignal detection part,
    a voluntary control part that generates a voluntary control signal for causing the driving part to generate the driving force in correspondence with an intention of the wearer by using the signal obtained by the biosignal process part,
    a drive current generation part that generates a current corresponding to the biosignal based on the voluntary control signal and supply the current to the driving part.

12. The wearable type movement assisting apparatus as claimed in claim 1, wherein the control part further includes
    a database that stores reference parameters of a series of phases that constitute a task of the finger of the wearer,
    an autonomous control part that estimates a task and a phase of the finger of the wearer by comparing the biosignal with the reference parameters and generates an autonomous control signal for causing the driving part to generate the driving force corresponding to the phase, and
    a drive current generation part that generates a current corresponding to the autonomous drive signal and supplies to the driving part.

13. The wearable type movement assisting apparatus as claimed in claim 10, wherein the control part includes
    a voluntary control part that generates a voluntary control signal for causing the driving part to generate the driving force in correspondence with an intention of the wearer by using the biosignal detected from the biosignal detection part,
    a database that stores reference parameters of a series of phases that constitute a task of the finger of the wearer,
    an autonomous control part that estimates a task and a phase of the finger of the wearer by comparing a finger bending angle detected by the finger joint angle sensor and the reference parameters and generates an autonomous control signal for causing the driving part to generate the driving force corresponding to the phase,
    a control signal compositing part that generates a total control signal by compositing the voluntary control signal and the autonomous control signal, and
    a drive current generation part that generates a total current corresponding to the total control signal and supplies the total current to the driving part.

14. The wearable type movement assisting apparatus as claimed in claim 13, wherein the database stores a hybrid ratio defined to establish a predetermined corresponding relationship with respect to the reference parameters of the series of phases, wherein the control signal compositing part composites the voluntary control signal and the autonomous control signal in accordance with the hybrid ratio in correspondence with the task and the phase estimated by the autonomous control part.

15. The wearable type movement assisting apparatus as claimed in claim 13, wherein the biosignal detection part is configured to detect another biosignal responsive to a predetermined driving force applied from the driving part to the wearer, wherein the control part includes a calibration part that detects the another biosignal and sets a correction value based on the another biosignal.

16. The wearable type movement assisting apparatus as claimed in claim 15, wherein the calibration part includes a load generation part that causes the driving part to apply the predetermined driving force to the wearer in a state where the movement assisting glove is worn by the wearer, and a correction value setting part that detects the another biosignal, generates a parameter of a calculation process performed by the drive current generation part, and sets a correction value unique to the wearer.

17. The wearable type movement assisting apparatus as claimed in claim 16, wherein the calibration part includes a calibration database that stores data of a corresponding relationship between the another biosignal and the finger bending angle detected by the finger joint angle sensor, wherein the correction value setting part is configured to correct the parameter based on the data stored in the calibration database.

* * * * *